(12) United States Patent
Smyth et al.

(10) Patent No.: US 8,088,741 B2
(45) Date of Patent: *Jan. 3, 2012

(54) COMPOUNDS FOR ENZYME INHIBITION

(75) Inventors: Mark S. Smyth, San Mateo, CA (US); Guy J. Laidig, Menlo Park, CA (US); Ronald T. Borchardt, Lawrence, KS (US); Barry A. Bunin, San Mateo, CA (US); Craig M. Crews, New Haven, CT (US); John H. Musser, San Carlos, CA (US); Kevin D. Shenk, Palo Alto, CA (US); Peggy A. Radel, Berkeley, CA (US)

(73) Assignee: Onyx Therapeutics, Inc., South San Francisco, CA (US)

( * ) Notice: Subject to any disclaimer, the term of this patent is extended or adjusted under 35 U.S.C. 154(b) by 842 days.

This patent is subject to a terminal disclaimer.

(21) Appl. No.: 11/596,028

(22) PCT Filed: May 9, 2005

(86) PCT No.: PCT/US2005/016335
§ 371 (c)(1),
(2), (4) Date: Nov. 19, 2007

(87) PCT Pub. No.: WO2005/111008
PCT Pub. Date: Nov. 24, 2005

(65) Prior Publication Data
US 2008/0090785 A1    Apr. 17, 2008

Related U.S. Application Data

(60) Provisional application No. 60/569,885, filed on May 10, 2004, provisional application No. 60/610,040, filed on Sep. 14, 2004, provisional application No. 60/634,366, filed on Dec. 7, 2004.

(51) Int. Cl.
A61K 38/06 (2006.01)
C12Q 1/34 (2006.01)
(52) U.S. Cl. .......................... 514/21.9; 435/18
(58) Field of Classification Search .................... None
See application file for complete search history.

(56) References Cited

U.S. PATENT DOCUMENTS

| | | | |
|---|---|---|---|
| 4,733,665 A | 3/1988 | Palmaz | |
| 5,071,957 A | 12/1991 | Konishi et al. | |
| 5,134,127 A | 7/1992 | Stella et al. | |
| 5,135,919 A | 8/1992 | Folkman et al. | |
| 5,340,736 A | 8/1994 | Goldberg | |
| 5,376,645 A | 12/1994 | Stella et al. | |
| 5,441,944 A | 8/1995 | Weisz et al. | |
| 5,874,418 A | 2/1999 | Stella et al. | |
| 6,046,177 A | 4/2000 | Stella et al. | |
| 6,099,851 A | 8/2000 | Weisman et al. | |
| 6,133,248 A | 10/2000 | Stella | |
| 6,204,257 B1 | 3/2001 | Stella et al. | |
| 6,235,717 B1 | 5/2001 | Leban et al. | |
| 6,410,512 B1 | 6/2002 | Mundy et al. | |
| 6,462,019 B1 | 10/2002 | Mundy et al. | |
| 6,492,333 B1 | 12/2002 | Mundy | |
| 6,613,541 B1 | 9/2003 | Vaddi et al. | |
| 6,617,309 B2 | 9/2003 | Tung et al. | |
| 6,656,904 B2 | 12/2003 | Mundy et al. | |
| 6,831,099 B1 | 12/2004 | Crews et al. | |
| 6,838,252 B2 | 1/2005 | Mundy et al. | |
| 6,838,436 B1 | 1/2005 | Mundy et al. | |
| 6,884,769 B1 | 4/2005 | Mundy et al. | |
| 6,902,721 B1 | 6/2005 | Mundy et al. | |
| 7,232,818 B2 | 6/2007 | Smyth et al. | |
| 7,388,017 B2 | 6/2008 | Tung et al. | |
| 7,417,042 B2 | 8/2008 | Smyth et al. | |
| 7,491,704 B2 | 2/2009 | Smyth et al. | |
| 7,687,456 B2 * | 3/2010 | Zhou et al. ......................... | 514/2 |
| 7,691,852 B2 * | 4/2010 | Shenk et al. ............... | 514/231.5 |
| 2003/0224469 A1 | 12/2003 | Buchholz et al. | |
| 2003/0236223 A1 | 12/2003 | Wagner et al. | |
| 2004/0266664 A1 | 12/2004 | Crews et al. | |
| 2005/0101781 A1 | 5/2005 | Agoulnik et al. | |
| 2005/0245435 A1 | 11/2005 | Smyth et al. | |
| 2005/0256324 A1 | 11/2005 | Laidig et al. | |
| 2006/0030533 A1 | 2/2006 | Smyth et al. | |
| 2006/0128611 A1 | 6/2006 | Lewis | |

(Continued)

FOREIGN PATENT DOCUMENTS

EP    0 411 660 A    2/1991

(Continued)

OTHER PUBLICATIONS

Kim, 1999, Bioorganic and Medicinal Chemistry Letters, 9, 3335-3340.*
Overkleeft, 2000, Tetrahedron Letters, 41, 6005-6009.*
Adams et al., "Proteasome Inhibitors: A Novel Class of Potent and Effective Antitumor Agents", *Cancer Research*, vol. 59, pp. 2615-2622, 1999.
Benedetti et al., "Versatile and Stereoselective Synthesis of Diamino Diol Dipeptide Isosteres, Core Units of Pseudopeptide HIV Protease Inhibitors", *J. Org. Chem.*, vol. 62 pp. 9348-9353, 1997.
Bougauchi et al., "Catalytic Asymmetric Epoxidation of α,β-Unsaturated Ketones Promoted by Lanthanoid Complexes", *J. Am. Chem. Soc.*, vol. 119, pp. 2329-2330, 1997.

(Continued)

*Primary Examiner* — Cecilia J Tsang
*Assistant Examiner* — Satyanarayana Gudibande
(74) *Attorney, Agent, or Firm* — Fish & Richardson P.C.

(57) ABSTRACT

Peptide-based compounds including heteroatom-containing, three-membered rings efficiently and selectively inhibit specific activities of N-terminal nucleophile (Ntn) hydrolases. The activities of those Ntn having multiple activities can be differentially inhibited by the compounds described. For example, the chymotrypsinlike activity of the 20S proteasome may be selectively inhibited with the inventive compounds. The peptide-based compounds include an epoxide or aziridine, and functionalization at the N-terminus. Among other therapeutic utilities, the peptide-based compounds are expected to display anti-inflammatory properties and inhibition of cell proliferation.

20 Claims, No Drawings

U.S. PATENT DOCUMENTS

| | | | |
|---|---|---|---|
| 2006/0241056 | A1 | 10/2006 | Orlowski et al. |
| 2007/0105786 | A1 | 5/2007 | Zhou et al. |
| 2008/0090785 | A1 | 4/2008 | Smythe et al. |
| 2009/0156473 | A1 | 6/2009 | Schubert |
| 2010/0144648 | A1 | 6/2010 | Shenk et al. |

FOREIGN PATENT DOCUMENTS

| | | |
|---|---|---|
| EP | 1 136 498 | 9/2001 |
| WO | WO 91/13904 | 9/1991 |
| WO | WO 94/15956 | 7/1994 |
| WO | WO 95/24914 | 9/1995 |
| WO | WO 96/13266 | 5/1996 |
| WO | WO 96/32105 | 10/1996 |
| WO | WO 98/10779 | 3/1998 |
| WO | WO-00/02548 A2 | 1/2000 |
| WO | WO-00/61167 A2 | 10/2000 |
| WO | WO-01/28579 A2 | 4/2001 |
| WO | WO-03/059898 A2 | 7/2003 |
| WO | WO 2005/105827 | 11/2005 |
| WO | WO-2005/105827 A2 | 11/2005 |
| WO | WO-2005/111008 A2 | 11/2005 |
| WO | WO 2006/017842 | 2/2006 |
| WO | WO 2006/045066 | 4/2006 |
| WO | WO 2006/099261 | 9/2006 |
| WO | WO 2007/056464 | 5/2007 |
| WO | WO 2007/067976 | 6/2007 |
| WO | WO 2007/149512 | 12/2007 |
| WO | WO 2008/140782 | 11/2008 |
| WO | WO 2009/045497 | 4/2009 |

OTHER PUBLICATIONS

Brown et al., "Selective Reductions. 37. Asymmetric Reduction of Prochiral Ketones with β-(3-Pinanyl)-9-borabicyclo[3.3.1]nonane", *J. Org. Chem.*, vol. 50, pp. 1384-1394, 1985.

Ciechanover, "The Ubiquitin-Proteasome Proteolytic Pathway", *Cell*, vol. 79, pp. 13-21, 1994.

Cohen, "AIDS Mood Upbeat—For a Change", *Science*, vol. 267, pp. 959-960, 1995.

Corey et al., "A General, Catalytic, and Enantioselective Synthesis of α-Amino Acids", *J. Am. Chem. Soc.*, vol. 114, pp. 1906-1908, 1992.

Corey et al., "Highly Enantioselective Borane Reduction of Ketones Catalyzed by Chiral Oxazaborolidines. Mechanism and Synthetic Implications", *J. Am. Chem. Soc.*, vol. 109, pp. 5551-5553, 1987.

Datta et al., "A Stereoselective Route to Hydroxyethylamine Dipeptide Isosteres", *J. Am. Chem. Soc.*, vol. 65, pp. 7609-7611, 2000.

Dess et al., "A Useful 12-I-5 Triacetoxyperiodinane (the Dess-Martin Periodinane) for the Selective Oxidation of Primary or Secondary Alcohols and a Variety of Related 12-I-5 Species", *J. Am. Chem. Soc.*, vol. 113, pp. 7277-7287, 1991.

Dess et al., "Readily Accessible 12-I-5 Oxidant for the Conversion of Primary and Secondary Alcohols to Aldehydes and Ketones", *J. Org. Chem.*, vol. 48, pp. 4155-4156, 1983.

Dobler, M. R., "Total synthesis of (+)-epopromycin B and its analogues-studies on the inhibition of cellulose biosynthesis," Tetrahedron Letters, 42(2):215-218 (2001).

Elofsson et al., "Towards subunit-specific proteasome inhibitors: synthesis and evaluation of peptide α',β'-epoxyketones", *Chemistry & Biology*, vol. 6, pp. 811-822, 1999.

Garrett et al., "Selective inhibitors of the osteoblast proteasome stimulate bone formation in vivo and in vitro", *J Clinical Investigation*, vol. 111, pp. 1771-1782, 2003.

Hanson et al., "Synthesis of New Dipeptide Analogues Containing Novel Ketovinyl and Hydroxyethylidene Isosteres via Grignard Addition to Chiral α-Amino Aldehydes", *J. Org. Chem.*, vol. 50, pp. 5399-5401, 1985.

Harding et al., "Novel Dipeptide Aldehydes Are Proteasome Inhibitors and Block the MHC-1 Antigen-Processing Pathway", *J. Immunology*, vol. 155, pp. 1767-1775, 1995.

Hardy, "The secret life of the hair follicle", *Trends in Genetics*, vol. 8, pp. 55-61, 1992.

Hoffman et al., "Highly Stereoselective Syntheses of *syn*- and *anti*-1,2-Amino Alcohols", *J. Org. Chem.*, vol. 67, pp. 1045-1056, 2002.

Iqbal et al., "Potent α-ketocarbonyl and boronic ester derived inhibitors of proteasome", *Bioorganic & Medicinal Chemistry Letters*, vol. 6, pp. 287-290, 1996.

Jacobsen et al., "Asymmetric Dihydroxylation via Ligand-Accelerated Catalysis", *J. Am. Chem. Soc.*, vol. 110, pp. 1968-1970, 1988.

Jones et al., "Total Synthesis of the Immunosuppressant (−)-FK-506", *J. Am. Chem. Soc.*, vol. 111, pp. 1157-1159, 1989.

Kim et al., "Proteasome inhibition by the natural products epoxomicin and dihydroeponemycin: insights into specificity and potency", *Bioorganic & Medicinal Chemistry Letters*, vol. 9, pp. 3335-3340, 1999.

Kumatori et al., "Abnormally high expression of proteasomes in human leukemic cells", *Proc. Natl. Acad. Sci. USA*, vol. 87, pp. 7071-7075, 1990.

Liang et al., "Synthesis of Cryptophycin 52 Using the Sharpless Asymmetric Dihydroxylation: Diol to Epoxide Transformation Optimized for a Base-Sensitive Substrate", *J. Am. Chem. Soc.*, vol. 65, pp. 3143-3147, 2000.

Marx et al., "Reactivity-Selectivity in the Swern Oxidation of Alcohols Using Dimethyl Sulfoxide-Oxalyl Chloride", *J. Org. Chem.*, vol. 49, pp. 788-793, 1984.

Meng et al., "Eponemycin Exerts Its Antitumor Effect through the Inhibition of Proteasome Function", *Cancer Research*, vol. 59, pp. 2798-2801, 1999.

Meng et al., "Epoxomicin, a potent and selective proteasome inhibitor, exhibits in vivo antiinflamatory activity", *Proc. Natl. Acad. Sci. USA*, vol. 96, pp. 10403-10408, 1999.

Myung et al., "Lack of Proteasome Active Site Allostery as Revealed by Subunit-Specific Inhibitors," *Molecular Cell*, vol. 7, No. 2, pp. 411-420, 2001.

Myung et al., "The Ubiquitin-Proteasome Pathway and Proteasome Inhibitors," *Medicinal Research Reviews*, vol. 21, No. 4, pp. 245-273, 2001.

Nemoto et al., "Catalytic Asymmetric Epoxidation of Enones Using La-BINOL-Triphenylarsine Oxide Complex: Structural Determination of the Asymmetric Catalyst", *J. Am. Chem. Soc.*, vol. 123, pp. 2725-2732, 2001.

Oishi et al., "Diastereoselective synthesis of new psi '(E)-CH=CMel- and psi '(Z)-CH=CMel-type alkene dipeptide isosteres by organocopper reagents and application to conformationally restricted cyclic RGD peptidomimetics," *J. Org. Chem.*, 67:6162-6173 (2002).

Palombella et al., "The Ubiquitin-Proteasome Pathway Is Required for Processing the NF-κB1 Precursor Protein and the Activation of NF-κB", *Cell*, vol. 78, pp. 773-785, 1994.

Paugam et al., "Characterization and role of protozoan parasite proteasomes", *Trends Parasitol.*, vol. 19, pp. 55-59, 2003.

Qureshi et al., "The Proteasome as a Lipopolysaccharide-Binding Protein in Macrophages: Differential Effects of Proteasome Inhibition on Lipopolysaccharide-Induced Signaling Events", *J. Immunology*, vol. 171, pp. 1515-1525, 2003.

Shao et al., "A New Asymmetric Synthesis of α-Methylcysteines via Chiral Aziridines", *J. Org. Chem.*, vol. 60, pp. 790-791, 1995.

Sharpless et al., "High Stereo- and Regioselectivities in the Transition Metal Catalyzed Epoxidations of Olefinic Alcohols by *tert*-Butyl Hydroperoxide", *J. Am. Chem. Soc.*, vol. 95, pp. 6136-6137, 1973.

Sin et al., "Total synthesis of the potent proteasome inhibitor epoxomicin: a useful tool for understanding proteasome biology", *Bioorganic & Medicinal Chemistry Letters*, vol. 9, pp. 2283-2288, 1999.

Spaltenstein et al., "Design and Synthesis of Novel Protease Inhibitors. Tripeptide α',β'-Epoxyketones as Nanomolar Inactivators of the Proteasome", *Tetrahedron Letters*, vol. 37, pp. 1343-1346, 1996.

Stein et al., "Kinetic Characterization of the Chymotryptic Activity of the 20S Proteasome", *Biochemistry*, vol. 35, pp. 3899-3908, 1996.

Thanos et al., "NF-κB: A Lesson in Family Values", *Cell*, vol. 80, pp. 529-532, 1995.

Traenckner et al., "A proteasome inhibitor prevents activation of NF-κB and stabilizes a newly phosphorylated form of IκB-α that is still bound to NF-κB", *EMBO J.*, vol. 13, pp. 5433-5441, 1994.

Tu et al., "An Efficient Assymettric Epoxidation Method for *trans*-Olefins Mediated by a Fructose-Derived Ketone", *J. Am. Chem. Soc.*, vol. 118, pp. 9806-9807, 1996.
Wang et al., "A New Type of Ketone Catalyst for Asymmetric Epoxidation", *J. Org. Chem.*, vol. 62, pp. 8622-8623, 1997.
Wipf et al., "Methyl- and (Trifluoromethyl)alkene Peptide Isosteres: Synthesis and Evaluation of Their Potential as β-Turn Promoters and Peptide Mimetics", *J. Org. Chem.*, vol. 63, pp. 6088-6089, 1998.
Gura, T., "Systems for Identifying New Drugs Are Often Faulty," Science, 278:1041-1042 (1997).
Jain, R.K., "Delivery of Molecular Medicine to Solid Tumors," Science, 271:1079-1080 (1996).
European Search Report from EP 08 16 4241 dated Jan. 22, 2009.
Overkleeft et al., "Solid phase synthesis of peptide vinyl sulfone and peptide epoxyketone proteasome inhibitors," Tetrahedron Letters, 41(32):6005-6009 (2000).
[Retrieved from] http://www.medterms.com 1 page [retrieved Sep. 16, 2005].
Almond et al. "The proteasome: a novel target for cancer chemotherapy" Leukemia, 16(4), 433-443, Apr. 2002.
Argiriadi et al. "Binding of Alkylurea Inhibitors to Epoxide Hydrolase Implicates Active Site Tyrosines in Substrate Activation", J. of Biol. Chem., 275(20), 15265-15270, May 19, 2000.
Bao et al. "PR-39 and PR-11 peptides inhibit ischemia-reperfusion injury by blocking proteasome-mediated IκBα degradation" Am. J. Physiol. Heart Circ. Physiol. 281:H2612-H2618, 2001.
Berge et al. "Pharmaceutical Salts", J. Pharm. Sci. 66(1), 1-19. Jan. 1977.
Bernier et al. "A Methionine aminopeptidase-2 Inhibitor, PPI-2458, for the treatment of rheumatoid arthritis", PNAS 101(29), 10768-73, Jul. 20, 2004.
Bogyo et al. "Biochemistry", PNAS 94:6629-6634, 1997.
Brinkley, Michael "A Brief Survey of Methods for Preparing Protein Conjugates with Dyes, Haptens, and Cross-Linking Reagents", Bioconjug. Chem 3:2-13, 1992.
Collins, Tucker, "Endothelial nuclear factor-κB and the initiation of the atherosclerotic lesion", Lab. Invest. 68(5), 499-508, 1993.
Craiu et al. "Lactacystin and clasto-lactacystin β-lactone modify multiple proteasome β-subunits and inhibit intracellular protein degradation and major hisotcompatibility complex class I antigen presentation" J. of Biol. Chem. 272(20), 13437-13445, May 16, 1997.
Fenteany et al. "A β-lactone related to lactacystin induces neurite outgrowth in a neuroblastoma cell line and inhibits cell cycle progression in an osteosarcoma cell line", PNAS 91:3358-3362, Apr. 1994.
Fox et al. "Organic Chemistry", Publisher: Jones & Bartlett Pub, Published Jun. 15, 2004, Sec. 5-6, pp. 177-178, ISBN-10: 0763721972, ISBN-13: 9780763721978.
Gao et al "Inhibition of ubiquitin-proteasome pathway-mediated IκBα degradation by a naturally occurring antibacterial peptide" J. Clin. Invest. 106:439-448, 2000.
Gonzales et al. "Pain relief in chronic pancreatitis by pancreaticojejunostomy. An institutional experience" Arch. Med. Res. 28(3), 387-390, 1997.
Graz University of Technology, "Database of Fluorescent Dyes Properties and Applications" WWW.Fluorophonres.org, 33 pgs, Exhibit B to response filed with US Patent office on Sep. 16, 2008 for U.S. Appl. No. 11/254,541 (now abandoned).
Green et al. "Protective Groups in Organic Synthesis", 2nd ed., Wiley & Sons, Inc., New York (1991).
Griffith et al. "Molecular recognition of angiogenesis inhibitors fumagillin and ovalicin by methionine aminopeptidase", PNAS 95:15183-88, Dec. 1998.
Harris et al. "Effects of transforming growth factor β on bone nodule formation and expression of bone morphogenetic protein 2, osteocalcin, osteopontin, alkaline phosphatase, and type I collagen mRNA in long-term cultures of fetal rat calvarial osteoblasts", J. Bone Miner. Res. 9(6), 855-863, 1994.
Haugland, Rosaria "Coupling of Monoclonal Antibodies with Fluorophores", Methods Mol. Biol. 45, 205-221, 1995.
International Search Report and Written Opinion for corresponding PCT Application No. PCT/US2005/016335, mailed Jan. 2, 2006, 17 pgs.
International Preliminary Report on Patentability for corresponding PCT Application No. PCT/US2005/016335, issued Nov. 14, 2006, 11 pgs.
Iqbal et al. "Potent Inhibitors of Proteasome", J. Med Chem. 38:2276-2277, 1995.
Kessler et al. "Extended peptide-based inhibitors efficiently target the proteasome and reveal overlapping specificities of the catalytic β-subunits", Chem & Biol. 8(9), 913-929, Aug. 8, 2001.
Kojima et al., "Two-way cleavage of β-amyloid protein precursor by multicatalytic proteinase" Fed. Eur. Biochem. Soc. 304:57-60, Jun. 1992.
Koong et al. Hypoxia causes the activation of nuclear factor-kB through the phosphorylation of IκBα on tyrosine residues[1], Cancer Research, 54:1425-1430, Mar. 15, 1994.
Koong et al. Hypoxic activation of nuclear factor-κB is mediated by a Ras and Raf signaling pathway and does not involve MAP kinase (ERK1 or ERK2)[1], Cancer Research, 54:5273-5279, Oct. 15, 1994.
Krise et al. "A Novel Prodrug Approach for Tertiary Amines: Synthesis and Preliminary Evaluation of N-Phosphonooxymethyl Prodrugs", J. Med. Chem. 42:3094-3100, 1999.
Molecular biology and biotechnology a comprehensive desk reference: Edited by R A Meyers. pp. 658-664. VCH, Weinheim, Germany, 1995, DM89 ISBN 1-56081-925-1.
Molecular Probes, Inc. , "Introduction to Fluorescence techniques", invitrogen detection technologies, 11 pgs, Molecular Probes, Inc. (2007), Exhibit A to response filed with US Patent Office on Sep. 16, 2008 for U.S. Appl. No. 11/254,541 (now abandoned).
Pye et al. "Proteasome inhibition ablates activation of NF-κB in myocardial reperfusion and reduces reperfusion of injury", Am. J. Physiol. Heart Circ. Physiol 284:H919-H926, 2003.
Reidlinger et al. "Catalytic Properties of 26 S and 20 S Proteasomes and Radiolabling of MB 1, LMP7, and C7 Subunits Associated with Trypsin-like and Chymotrypsin-like Activities", J. of Biol Chem. 272(40), 24899-24905, May 27, 1997.
Safadi et al., "Phosphoryloxymet hyl Carbarnates and Carbonates-Novel Water-Soluble Prodrugs for Amines and Hindered Alcohols", Pharmaceutical Research 10(9), 1350-1355, Mar. 2, 1993.
Simsek et al. "Hepatitis B Virus Large and Middle Glycoproteins Are Degraded by a Proteasome Pathway in Glucosidase-Inhibited Cells but Not in Cells with Functional Glucosidase Enzyme", J. Virol. 79(20), 12914-12920, Oct. 2005.
Szalay et al. "Ongoing coxsackievirus myocarditis is associated with increased formation and activity of myocardial immunoproteaseomes", Am. J. Pathol. 168(5), 1542-1552, May 2006.
Terato et al. "Induction of arthritis with monoclonal antibodies to collagen[1]" J. Immunol, 148(7), 2103-2108, Apr. 1, 1992.
Xu et al. "Mutations in the tumor suppressors Smad2 and Smad4 inactivate transforming growth factor β signaling by targeting Smads to the ubiquitin-proteasome pathway", PNAS 97(9), 4820-4825, Apr. 25, 2000.
Yu et al. "The Ubiquitin-Proteasome System Facilitates the Transfer of Murine Coronavirus from Endosome to Cytoplasm during Virus Entry", J. Virol. 79(1), 644-648, Jan. 2005.
Caira, "Crystalline Polymorphism of Organic Compounds," *Topics in Current Chemistry*, 1998, 198:163-208.
Demo et al., "Antitumor Activity of PR-171, a Novel Irreversible Inhibitor of the Proteasome," *Cancer Research*, 2007, 67(13):6383-6391.
Golub et al., "Molecular Classification of Cancer: Class Discovery and Class Prediction by Genes Expression Monitoring," *Science*, 1999, 286:531-537.
Groll et al., "Crystal Structure of Epoxomicin:20S Proteasome Reveals a Molecular Basis for Selectivity of α',β'-Epoxyketone Proteasome Inhibitors," *J. Am. Chem. Soc.* 2000, 122:1237-1238.
Hardy, "The secret life of the hair follicle," *Trends in Genetics*, 1992, 8:55-61.
Hilfiker, Ed., *Polymorphism in the Pharmaceutical Industry*, 2006, pp. 12-15.
Lala et al., "Role of notric oxide in tymor progression: Lessons from experimental tumors," *Cancer and Metastasis Reviews*, 1998, 17:91-106.

Loftsson et al., "Pharmaceutical Applications of Cyclodextrins. 1. Drug Solubilization and Stabalization," *Journal of Pharmaceutical Sciences, American Pharmaceutical Association*, 85(10):1017-1025 (1996).

Morris, "Structural Aspects of Hydrates and Solvates in Polymorphism in Pharmaceutical Solids,"*Polymorphism in Pharmaceutical Solids*, 1999, Ed. H.G. Nbrittain, Marcel Dekker, New York, pp. 125-181.

Strickley, Robert G., "Solubilizing Excipients in Oral and Injectable Formulations," Pharmaceutical Research, 21(2):201-230 (2004).

Thompson., "Cyclodextrins-enabling excipients: their present and future use in pharmaceuticals," Critical Reviews in Therapeutic Drug Carrier Systems, 14(1):1-104 (1997).

Tong, Wei-Qin (Tony), "Applications of Complexation in the Formulation of Insoluble Compounds," R. Liu, Ed., pp. 111-139 (2000).

Vogel's textbook of practical organic chemistry, $5^{th}$ Ed. See p. 135, "2.20 Recrystallisation Techniques" and p. 141, $2^{nd}$ paragraph onwards.

Voskoglou-Nomikos, "Clinical Predictive Value of the in Vitro Cell Line, Human Xenograft, and Mouse Allograft Preclinical Cancer Models," Clin Cancer Res., 2003, 9(11):4227-4239.

Zhou et al., "Design and Synthesis of an Orally Bioavailable and Selectrive Peptide Epoxyketone Proteasome Inhibitor (PR-047)," *J. Med. Chem.*, 2009, 52 (9):3028-3038.

International Search Report and Written Opinion for corresponding PCT Application No. PCT/US2005/012740, mailed Jan. 9, 2006, 16 pgs.

International Preliminary Report on Patentability for corresponding PCT Application No. PCT/US2005/012740, issued Oct. 19, 2006, 11 pgs.

Authorized Officer M. Kollmannsberger, International Search Report and Written Opinion for PCT/US2007/014427, mailed Dec. 3, 2007, 12 pages.

Authorized Officer M. Kollmannsberger, International Preliminary Report on Patentability PCT/US2007/014427, issued Dec. 22, 2008, 8 pages.

European Search Report, EP 09 00 6228, completed Aug. 25, 2009, 7 pages.

Authorized Officer A. Schleifenbaum, International Search Report and Written Opinion of the International Searching Authority for PCT/US2008/005997, mailed Nov. 7, 2008, 8 pages.

Authorized Officer Philippe Becamel, International Preliminary Report on Patentability for PCT/US2008/005997, issued Nov. 10, 2009, 7 pages.

Authorized Officer Grant McNeice, International Search Report for PCT/US2009/061498, mailed Dec. 10, 2009, 5 pages.

Authorized Officer Sonya James, International Search Report and Written Opinion of the International Searching Authority for PCT/US2006/043503, mailed Feb. 19, 2007, 17 pages.

Authorized Officer Dorothée Mülhausen, International Search Report and Written Opinion of the International Searching Authority for PCT/US2006/043503, mailed Feb. 19, 2007, 17 pages.

Authorized Officer Marc Kloth, International Search Report and Written Opinion of the Internatinal Searching Authority for PCT/US2010/028126, mailed Jun. 9, 2010, 13 pages.

Partial International Search Report for PCT/US2008/011443, dated Dec. 9, 2008, 6 pages.

Authorized Officer M. Groenendijk, International Search Report and Written Opinion of the International Searching Authority for PCT/US2005/028246, mailed Jan. 19, 2006, 11 pages.

Authorized Officer Yoshiko Kuwahara, International Preliminary Report on Patentability for PCT/US2005/028246, issued Feb. 6, 2007, 8 pages.

Authorized Officer D. Grassi, International Search Report and Written Opinion of the International Searching Authority for PCT/US2005/017000, mailed Feb. 3, 2006, 12 pages.

Authorized Beate Giffo-Schmitt, International Preliminary Report on Patentability for PCT/US2005/017000, issued Nov. 21, 2006, 12 pages.

Authorized Officer M. Groenendijk, International Search Report and Written Opinion of the International Searching Authority for PCT/US2005/037966, mailed Jan. 24, 2006, 17 pages.

Authorized Officer Dorothée Mülhausen, International Preliminary Report on Patentability for PCT/US2005/037966, issued Apr. 24, 2007, 12 pages.

Authorized Officer M. Groenendijk, International Search Report and Written Opinion of the International Searching Authority for PCT/US2005/044451, mailed May 2, 2006, 12 pages.

Authorized Officer Philippe Becamel, International Preliminary Report on Patentability for PCT/US2005/044451, issued Jun. 13, 2007, 8 pages.

Authorized Officer Sonya James, International Search Report and Written Opinion of the International Searching Authority for PCT/US2008/011443, mailed Mar. 25, 2009, 16 pages.

Authorized Officer Athina Nickitas-Etienne, International Preliminary Report on Patentability for PCT/US2008/011443, issued Apr. 7, 2010, 12 pages.

* cited by examiner

SEQUENCE LISTING

```
<160> NUMBER OF SEQ ID NOS: 1

<210> SEQ ID NO 1
<211> LENGTH: 10
<212> TYPE: PRT
<213> ORGANISM: Rattus rattus
<220> FEATURE:
<221> NAME/KEY: VARIANT
<222> LOCATION: 1, 6
<223> OTHER INFORMATION: Xaa = Any Amino Acid

<400> SEQUENCE: 1

Xaa Gln Asn Pro Met Xaa Thr Gly Thr Ser
 1               5                  10
```

COMPOUNDS FOR ENZYME INHIBITION

CROSS-REFERENCE TO RELATED APPLICATIONS

This application is a national stage filing under 35 U.S.C. 371 of International Application PCT/US2005/016335 filed May 9, 2005, which claims the benefit of U.S. Provisional Application No. 60/569,885, filed May 10, 2004, U.S. Provisional Application No. 60/610,040, filed Sep. 14, 2004, and U.S. Provisional Application No. 60/634,366, filed Dec. 7, 2004. The entire teachings of the referenced applications are incorporated by reference herein in their entirety.

TECHNICAL FIELD

This invention relates to compounds and methods for enzyme inhibition. In particular, the invention relates to therapeutic methods based on enzyme inhibition.

BACKGROUND OF THE INVENTION

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis, cell division, and NF-κB activation.

The 20S proteasome is a 700 kDa cylindrical-shaped multicatalytic protease complex comprised of 28 subunits organized into four rings that plays important roles in cell growth regulation, major histocompatibility complex class I presentation, apoptosis, antigen processing, NF-κB activation, and transduction of pro-inflammatory signals. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteasome thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three γ-interferon-inducible β subunits (LMP7, LMP2 and MECL1), which replace their normal counterparts, X, Y and Z respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in β subunits and the exchange of γ interferon-inducing β subunits alter these activities to various degrees.

There are several examples of small molecules which have been used to inhibit proteasome activity; however, these compounds generally lack the specificity, stability, or potency necessary to explore and exploit the roles of the proteasome at the cellular and molecular level. Therefore, the synthesis of small molecule inhibitor(s) with increased site specificity, improved stability and solubility, and increased potency are needed to allow the exploration of the roles of the proteasome at the cellular and molecular level.

SUMMARY OF THE INVENTION

The invention relates to classes of molecules known as peptide α',β'-epoxides and peptide α',β'-aziridines. The parent molecules are understood to bind efficiently, irreversibly and selectively to N-terminal nucleophile (Ntn) hydrolases, and can specifically inhibit particular activities of enzymes having multiple catalytic activity.

Once thought merely to dispose of denatured and misfolded proteins, the proteasome is now recognized as constituting proteolytic machinery that regulates the levels of diverse intracellular proteins through their degradation in a signal-dependent manner. Hence, there is great interest in identifying reagents that can specifically perturb the activities of the proteasome and other Ntn hydrolases and thereby be used as probes to study the role of these enzymes in biological processes. Compounds that target the Ntn hydrolases are herein described, synthesized, and investigated. Peptide epoxides and peptide aziridines that can potently, selectively, and irreversibly inhibit particular proteasome activities are disclosed and claimed.

Unlike several other peptide-based inhibitors, the peptide epoxides and peptide aziridines described herein are not expected to substantially inhibit non-proteasomal proteases such as trypsin, chymotrypsin, cathepsin B, papain, and calpain at concentrations up to 50 μM. At higher concentrations, inhibition may be observed, but would be expected to be competitive and not irreversible, if the inhibitor merely competes with the substrate. The novel peptide epoxides and peptide aziridines are also expected to inhibit NF-κB activation and to stabilize p53 levels in cell culture. Moreover, these compounds would be expected to have anti-inflammatory activity. Thus, these compounds can be unique molecular probes, which have the versatility to explore Ntn enzyme function in normal biological and pathological processes.

In one aspect, the invention provides inhibitors comprising a heteroatom-containing three-membered ring. These inhibitors can inhibit catalytic activity of N-terminal nucleophile hydrolase enzymes (for example, the 20S proteasome, or the 26S proteasome) when said inhibitor is present at concentrations below about 50 μM. Regarding the 20S proteasome, particular hydrolase inhibitors inhibit chymotrypsin-like activity of the 20S proteasome when the inhibitor is present at concentrations below about 5 μM, and does not inhibit trypsin-like activity or PGPH activity of the 20S proteasome when present at concentrations below about 5 μM. The hydrolase inhibitor may be, for example, a peptide α',β'-epoxy ketone or α',β'-aziridine ketone, and the peptide may be a tetrapeptide. The peptide may include branched or unbranched side chains such as hydrogen, $C_{1-6}$alkyl, $C_{1-6}$hydroxyalkyl, $C_{1-6}$alkoxyalkyl, aryl, $C_{1-6}$aralkyl, $C_{1-6}$alkylamine, $C_{1-6}$carboxylic acid, $C_{1-6}$carboxyl ester, $C_{1-6}$alkylthiol, or $C_{1-6}$alkylthioether, for example isobutyl, 1-naphthyl, phenylmethyl, and 2-phenylethyl. The α'-carbon of the α',β'-epoxy ketone or α',β'-aziridine ketone may be a chiral carbon atom, such as an (R) or β configured carbon, as these are defined herein.

In another aspect, the invention provides pharmaceutical compositions, including a pharmaceutically acceptable carrier and a pharmaceutically effective amount of the hydrolase inhibitor, which ameliorates the effects of neurodegenerative disease (such as Alzheimer's disease), muscle-wasting diseases, cancer, chronic infectious diseases, fever, muscle disuse, denervation, nerve injury, fasting, and immune-related conditions, among others.

In another aspect, the invention provides anti-inflammatory compositions.

In another aspect, the invention provides methods for the following: inhibiting or reducing HIV infection in a subject; affecting the level of viral gene expression in a subject; altering the variety of antigenic peptides produced by the proteasome in an organism; determining whether a cellular, developmental, or physiological process or output in an organism is regulated by the proteolytic activity of a particular Ntn hydrolase; treating Alzheimer's disease in a subject; reducing the rate of muscle protein degradation in a cell; reducing the rate of intracellular protein degradation in a cell; reducing the rate of p53 protein degradation in a cell; inhibiting the growth of p53-related cancers in a subject; inhibiting antigen presentation in a cell; suppressing the immune system of a subject; inhibiting IκB-α degradation in an organism; reducing the content of NF-κB in a cell, muscle, organ or subject; affecting cyclin-dependent eukaryotic cell cycles; treating proliferative disease in a subject; affecting proteasome-dependent regulation of oncoproteins in a cell; treating cancer growth in a subject; treating p53-related apoptosis in a subject; and screening proteins processed by N-terminal nucleophile hydrolases in a cell. Each of these methods involves administering or contacting an effective amount of a composition comprising the hydrolase inhibitors disclosed herein, to a subject, a cell, a tissue, an organ, or an organism.

Other features and advantages of the invention will be apparent from the following detailed description, and from the claims.

DETAILED DESCRIPTION OF THE INVENTION

The invention involves compounds useful as enzyme inhibitors. These compounds are generally useful to inhibit enzymes having a nucleophilic group at the N-terminus. For example, activities of enzymes or enzyme subunits having N-terminal amino acids with nucleophiles in their side chains, such as threonine, serine, or cysteine can be successfully inhibited by the enzyme inhibitors described herein. Activities of enzymes or enzyme subunits having non-amino acid nucleophilic groups at their N-termini, such as, for example, protecting groups or carbohydrates, can also be successfully inhibited by the enzyme inhibitors described herein.

While not bound by any particular theory of operation, it is believed that such N-terminal nucleophiles of Ntn form covalent adducts with the epoxide functional group of the enzyme inhibitors described herein. For example, in the β5/Pre2 subunit of 20S proteasome, the N-terminal threonine is believed to irreversibly form a morpholino or piperazino adduct upon reaction with a peptide epoxide or aziridine such as those described below. Such adduct formation would involve ring-opening cleavage of the epoxide or aziridine.

In embodiments including such groups bonded to α' carbons, the stereochemistry of the α'-carbon (that carbon forming a part of the epoxide or aziridine ring) can be (R) or (S). The invention is based, in part, on the structure-function information disclosed herein, which suggests the following preferred stereochemical relationships. Note that a preferred compound may have a number of stereocenters having the indicated up-down (or β-α, where β as drawn herein is above the plane of the page) or (R)-(S) relationship (that is, it is not required that every stereocenter in the compound conform to the preferences stated). In some preferred embodiments, the stereochemistry of the α' carbon is (R), that is, the X atom is β, or above the plane of the molecule.

Regarding the stereochemistry, the Cahn-Ingold-Prelog rules for determining absolute stereochemistry are followed. These rules are described, for example, in *Organic Chemistry*, Fox and Whitesell; Jones and Bartlett Publishers, Boston, Mass. (1994); Section 5-6, pp 177-178, which section is hereby incorporated by reference. Peptides can have a repeating backbone structure with side chains extending from the backbone units. Generally, each backbone unit has a side chain associated with it, although in some cases, the side chain is a hydrogen atom. In other embodiments, not every backbone unit has an associated side chain. Peptides useful in peptide epoxides or peptide aziridines have two or more backbone units. In some embodiments useful for inhibiting chymotrypsin-like (CT-L) activity of the proteasome, between two and eight backbone units are present, and in some preferred embodiments for CT-L inhibition, between two and six backbone units are present.

The side chains extending from the backbone units can include natural aliphatic or aromatic amino acid side chains, such as hydrogen (glycine), methyl (alanine), isopropyl (valine), sec-butyl (isoleucine), isobutyl (leucine), phenylmethyl (phenylalanine), and the side chain constituting the amino acid proline. The side chains can also be other branched or unbranched aliphatic or aromatic groups such as ethyl, n-propyl, n-butyl, t-butyl, and aryl substituted derivatives such as 1-phenylethyl, 2-phenylethyl, (1-naphthyl)methyl, (2-naphthyl)methyl, 1-(1-naphthyl)ethyl, 1-(2-naphthyl)ethyl, 2-(1-naphthyl)ethyl, 2-(2-naphthyl)ethyl, and similar compounds. The aryl groups can be further substituted with branched or unbranched $C_{1-6}$alkyl groups, or substituted alkyl groups, acetyl and the like, or further aryl groups, or substituted aryl groups, such as benzoyl and the like. Heteroaryl groups can also be used as side chain substituents. Heteroaryl groups include nitrogen-, oxygen-, and sulfur-containing aryl groups such as thienyl, benzothienyl, naphthothienyl, thianthrenyl, furyl, pyranyl, isobenzofuranyl, chromenyl, pyrrolyl, imidazolyl, pyrazolyl, pyridyl, pyrazinyl, indolyl, purinyl, quinolyl, and the like.

In some embodiments, polar or charged residues can be introduced into the peptide epoxides or peptide aziridines. For example, naturally occurring amino acids such as hydroxy-containing (Thr, Tyr, Ser) or sulfur-containing (Met, Cys) can be introduced, as well as non-essential amino acids, for example, taurine, carnitine, citrulline, cystine, ornithine, norleucine and others. Non-naturally occurring side chain substituents with charged or polar moieties can also be included, such as, for example, $C_{1-6}$alkyl chains or $C_{6-12}$aryl groups with one or more hydroxy, short chain alkoxy, sulfide, thio, carboxyl, ester, phospho, amido or amino groups, or such substituents substituted with one or more halogen atoms.

In some preferred embodiments, there is at least one aryl group present in a side chain of the peptide moiety.

In some embodiments, the backbone units are amide units [—NH—CHR—C(=O)—], in which R is the side chain. Such a designation does not exclude the naturally occurring amino acid proline, or other non-naturally occurring cyclic secondary amino acids, which will be recognized by those of skill in the art.

In other embodiments, the backbone units are N-alkylated amide units (for example, N-methyl and the like), olefinic analogs (in which one or more amide bonds are replaced by olefinic bonds), tetrazole analogs (in which a tetrazole ring imposes a cis-configuration on the backbone), or combinations of such backbone linkages. In still other embodiments, the amino acid α-carbon is modified by α-alkyl substitution, for example, aminoisobutyric acid. In some further embodiments, side chains are locally modified, for example, by $\Delta^E$ or $\Delta^Z$ dehydro modification, in which a double bond is present between the α and β atoms of the side chain, or for example by $\Delta^E$ or $\Delta^Z$ cyclopropyl modification, in which a cyclopropyl group is present between the α and β atoms of the side chain. In still further embodiments employing amino acid groups, D-amino acids can be used. Further embodiments can include side chain-to-backbone cyclization, disulfide bond formation, lactam formation, azo linkage, and other modifications discussed in "Peptides and Mimics, Design of Conformationally Constrained" by Hruby and Boteju, in "Molecular Biology and Biotechnology: A Comprehensive Desk Reference", ed. Robert A. Meyers, VCH Publishers (1995), pp. 658-664, which is hereby incorporated by reference.

One aspect of the invention relates to compounds having a structure of formula (I) or a pharmaceutically acceptable salt thereof,

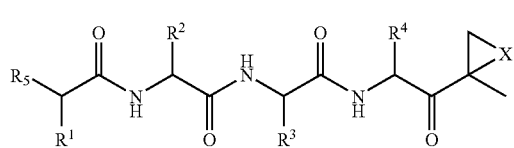

(I)

wherein
each A is independently selected from C=O, C=S, and SO$_2$, preferably C=O;
each B is independently selected from C=O, C=S, and SO$_2$, preferably C=O;
D is absent or is C$_{1-8}$alkyl;
G is selected from O, NH, and N—C$_{1-6}$alkyl;
K is absent or is selected from from C=O, C=S, and SO$_2$, preferably K is absent or is C=O;
L is absent or is selected from C=O, C=S, and SO$_2$, preferably L is absent or C=O;
M is absent or is C$_{1-8}$alkyl;
Q is absent or is selected from O, NH, and N—C$_{1-6}$alkyl, preferably Q is absent, O, or NH, most preferably Q is absent;
X is selected from O, S, NH, and N—C$_{1-6}$alkyl, preferably O;
each V is independently absent or is selected from O, S, NH, and N—C$_{1-6}$alkyl, preferably V is absent or O;
W is absent or is independently selected from O, S, NH, and N—C$_{1-6}$alkyl, preferably O;
Y is absent or is selected from O, NH, N—C$_{1-6}$alkyl, S, SO, SO$_2$, CHOR$^{10}$, and CHCO$_2$R$^{10}$;

each Z is independently selected from O, S, NH, and N—C$_{1-6}$alkyl, preferably O;
R$^1$, R$^2$, R$^3$, and R$^4$ are each independently selected from C$_{1-6}$alkyl, C$_{1-6}$hydroxyalkyl, C$_{1-6}$alkoxyalkyl, aryl, C$_{1-6}$aralkyl, and R$^{14}$DVKOC$_{1-3}$alkyl-, wherein at least one of R$^1$ and R$^3$ is R$^{14}$DVKOC$_{1-3}$alkyl-;
R$^5$ is N(R$^6$)LQR$^7$;
R$^6$ is selected from hydrogen, OH, and C$_{1-6}$alkyl, preferably C$_{1-6}$alkyl;
R$^7$ is a further chain of amino acids, hydrogen, a protecting group, aryl, or heteroaryl, any of which is optionally substituted with halogen, carbonyl, nitro, hydroxy, aryl, C$_{1-5}$alkyl; or R$^7$ is selected from C$_{1-6}$alkyl, C$_{1-6}$alkenyl, C$_{1-6}$alkynyl, C$_{1-6}$aralkyl, C$_{1-6}$heteroaralkyl, R$^8$ZA—C$_{1-8}$alkyl-, R$^{11}$Z—C$_{1-8}$alkyl-, (R$^8$O)(R$^9$O)P(=O)O—C$_{1-8}$alkyl-ZAZ—C$_{1-8}$alkyl-, (R$^8$O)(R$^9$O)P(=O)O—C$_{1-8}$alkyl-Z—C$_{1-8}$alkyl-, R$^8$ZA—C$_{1-8}$alkyl-ZAZ—C$_{1-8}$alkyl-, heterocyclylMZAZ—C$_{1-8}$alkyl-, (R$^8$O)(R$^9$O)P(=O)O—C$_{1-8}$alkyl-, (R$^{10}$)$_2$N—C$_{1-8}$alkyl-, (R$^{10}$)$_3$N$^+$—C$_{1-8}$alkyl-, heterocyclylM-, carbocyclylM-, R$^{11}$SO$_2$C$_{1-8}$alkyl-, and R$^{11}$SO$_2$NH; or
R$^6$ and R$^7$ together are C$_{1-6}$alkyl-Y—C$_{1-6}$alkyl, C$_{1-6}$alkyl-ZA—C$_{1-6}$alkyl, A—C$_{1-6}$alkyl-ZA—C$_{1-6}$alkyl, A—C$_{1-6}$alkyl-A, or C$_{1-6}$alkyl-A, preferably C$_{1-2}$alkyl-Y—C$_{1-2}$alkyl, C$_{1-2}$alkyl-ZA—C$_{1-2}$alkyl, A—C$_{1-2}$alkyl-ZA—C$_{1-2}$alkyl, A—C$_{1-3}$alkyl-A, or C$_{1-4}$alkyl-A, thereby forming a ring, preferably R$^6$ is hydrogen and R$^7$ is C$_{1-6}$alkyl;
R$^8$ and R$^9$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, preferably from hydrogen, metal cation, and C$_{1-6}$alkyl, or R$^8$ and R$^9$ together are C$_{1-6}$alkyl, thereby forming a ring;
each R$^{10}$ is independently selected from hydrogen and C$_{1-6}$alkyl, preferably C$_{1-6}$alkyl;
each R$^{11}$ is independently selected from hydrogen, OR$^{10}$, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl;
R$^{14}$ is selected from hydrogen, (R$^{15}$O)(R$^{16}$O)P(=O)W—, R$^{15}$GB—, heterocyclyl-, (R$^{17}$)$_2$N—, (R$^{17}$)$_3$N$^+$—, R$^{17}$SO$_2$GBG—, and R$^{15}$GBC$_{1-8}$alkyl- where the C$_{1-8}$alkyl moiety is optionally substituted with OH, C$_{1-8}$alkylW (optionally substituted with halogen, preferably fluorine), aryl, heteroaryl, carbocyclyl, heterocyclyl, and C$_{1-6}$aralkyl, preferably at least one occurrence of R$^{14}$ is other than hydrogen;
R$^{15}$ and R$^{16}$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, preferably from hydrogen, metal cation, and C$_{1-6}$alkyl, or R$^{15}$ and R$^{16}$ together are C$_{1-6}$alkyl, thereby forming a ring; and
each R$^{17}$ is independently selected from hydrogen, OR$^{10}$, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl;
provided that when R$_6$ is H, L is C=O, and Q is absent, R$^7$ is not hydrogen, C$_{1-6}$alkyl, or substituted or unsubstituted aryl or heteroaryl; and
D, G, V, K, and W are selected such that there are no O—O, N—O, S—N, or S—O bonds.

Suitable N-terminal protecting groups known in the art of peptide syntheses, include t-butoxy carbonyl (Boc), benzoyl (Bz), fluoren-9-ylmethoxycarbonyl (Fmoc), triphenylmethyl (trityl) and trichloroethoxycarbonyl (Troc) and the like. The use of various N-protecting groups, e.g., the benzyloxy carbonyl group or the t-butyloxycarbonyl group (Boc), various coupling reagents, e.g., dicyclohexylcarbodiimide (DCC), 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HOBT), and various cleavage conditions: for example, trifluoracetic acid (TFA), HCl in dioxane, hydrogenation on Pd-C in organic solvents (such as methanol or ethyl acetate), boron tris(trifluoroacetate), and cyanogen bromide, and reaction in solution with isolation and purification of intermediates are well-known in the art of peptide synthesis, and are equally applicable to the preparation of the subject compounds.

In certain embodiments, $R^1$, $R^2$, $R^3$, and $R^4$ are each independently selected from $C_{1-6}$alkyl, $C_{1-6}$hydroxyalkyl, $C_{1-6}$alkoxyalkyl, aryl, $C_{1-6}$aralkyl, and $R^{14}DVKOC_{1-3}$alkyl- wherein at least one of $R^1$ and $R^3$ is $R^{14}DVKOC_{1-3}$alkyl-. In preferred embodiments, one of $R^1$ and $R^3$ is $C_{1-6}$aralkyl and the other is $R^{144}DVKOC_{1-3}$alkyl-, and $R^2$ and $R^4$ are independently $C_{1-6}$alkyl. In the most preferred embodiment, one of $R^1$ and $R^3$ is 2-phenylethyl or phenylmethyl and the other is $R^{14}DVKOCH_2$- or $R^{14}DVKO(CH_3)CH$—, and both $R^2$ and $R^4$ are isobutyl.

In certain embodiments, each $R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl.

In certain embodiments, each $R^{17}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl.

In certain embodiments, L and Q are absent and $R^7$ is selected from hydrogen, a further chain of amino acids, $C_{1-6}$acyl, a protecting group, aryl, heteroaryl, $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^6$ is $C_{1-6}$alkyl and $R^7$ is selected from butyl, allyl, propargyl, phenylmethyl, 2-pyridyl, 3-pyridyl, and 4-pyridyl.

In other embodiments, L is $SO_2$, Q is absent, and $R^7$ is selected from $C_{1-6}$alkyl and aryl. In certain such embodiments, $R^7$ is selected from methyl and phenyl.

In certain embodiments, L is C=O and $R^7$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8ZA$—$C_{1-8}$alkyl-, $R^{11}Z$—$C_{1-8}$alkyl-, $(R^8O)(R^9O)P(=O)O$—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, $R^8ZA$—$C_{1-8}$alkyl-ZAZ—$C_{1-8}$alkyl-, heterocyclylMZAZ—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$—. In certain embodiments, L is C=O, Q is absent, and $R^7$ is H.

In certain embodiments, $R^6$ is $C_{1-6}$alkyl, $R^7$ is $C_{1-6}$alkyl, Q is absent, and L is C=O. In certain such embodiments, $R^7$ is ethyl, isopropyl, 2,2,2-trifluoroethyl, or 2-(methylsulfonyl)ethyl.

In other embodiments, L is C=O, Q is absent, and $R^7$ is $C_{1-6}$aralkyl. In certain such embodiments, $R^7$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^6$ is $C_{1-6}$alkyl, and $R^7$ is aryl. In certain such embodiments, $R^7$ is substituted or unsubstituted phenyl.

In certain embodiments, L is C=O, Q is absent or O, and $R^7$ is —$(CH_2)_n$carbocyclyl. In certain such embodiments, $R^7$ is cyclopropyl or cyclohexyl.

In certain embodiments, L and A are C=O, Q is absent, Z is O, and $R^7$ is selected from $R^8ZA$—$C_{1-8}$alkyl-, $R^{11}Z$—$C_{1-8}$alkyl-, $R^8ZA$—$C_{1-8}$alkyl-ZAZ—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, and heterocyclylMZAZ-$C_{1-8}$alkyl-. In certain such embodiments, $R^7$ is heterocyclylM-ZAZ-$C_{1-8}$alkyl- where heterocyclyl is substituted or unsubstituted oxodioxolenyl or $N(R^{12})(R^{13})$, wherein $R^{12}$ and $R^{13}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, and $R^7$ is selected from $(R^8O)(R^9O)P(=O)O$—$C_{1-8}$alkyl-, $(R^{10})_2NC_{1-8}$alkyl, $(R^{10})_3N^+(CH_2)_n$—, and heterocyclyl-M-. In certain such embodiments, $R^7$ is —$C_{1-8}$alkylN$(R^{10})_2$— or —$C_{1-8}$alkylN$^+(R^{10})_3$, where $R^{10}$ is $C_{1-6}$alkyl. In certain other such embodiments, $R^7$ is heterocyclylM-, where heterocyclyl is selected from morpholino, piperidino, piperazino, and pyrrolidino.

In certain embodiments, L is C=O, $R^6$ is $C_{1-6}$alkyl, Q is selected from O and NH and $R^7$ is selected from $C_{1-6}$alkyl, cycloalkyl-M, $C_{1-6}$araalkyl, and $C_{1-6}$heteroaraalkyl. In other embodiments, L is C=O, $R^6$ is $C_{1-6}$alkyl, Q is selected from O and NH, and $R^7$ is $C_{1-6}$alkyl, where $C_{1-6}$alkyl is selected from methyl, ethyl, and isopropyl. In further embodiments, L is C=O, $R^6$ is $C_{1-6}$alkyl, Q is selected from O and NH and $R^7$ is $C_{1-6}$aralkyl, where aralkyl is phenylmethyl. In other embodiments, L is C=O, $R^6$ is $C_{1-6}$alkyl, Q is selected from O and NH, and $R^7$ is $C_{1-6}$heteroaralkyl, where heteroaralkyl is (4-pyridyl)methyl.

In certain embodiments, L is absent or is C=O, and $R^6$ and $R^7$ together are $C_{1-6}$alkyl-Y—$C_{1-6}$alkyl, $C_{1-6}$alkyl-ZA—$C_{1-6}$alkyl, or $C_{1-6}$alkyl-A, thereby forming a ring. In certain preferred embodiments, L is C=O, Q and Y are absent, and $R^6$ and $R^7$ together are $C_{1-3}$alkyl-Y—$C_{1-3}$alkyl. In another preferred embodiment, L and Q are absent, and $R^6$ and $R^7$ together are $C_{1-3}$alkyl-Y—$C_{1-3}$alkyl. In another preferred embodiment, L is C=O, Q is absent, Y is selected from NH and N—$C_{1-6}$alkyl, and $R^6$ and $R^7$ together are $C_{1-3}$alkyl-Y—$C_{1-3}$alkyl. In another preferred embodiment, L is C=O, Y is absent, and $R^6$ and $R^7$ together are $C_{1-3}$alkyl-Y—$C_{1-3}$alkyl. In another preferred embodiment, L and A are C=O, and $R^6$ and $R^7$ together are $C_{1-2}$alkyl-ZA—$C_{1-2}$alkyl. In another preferred embodiment, L and A are C=O and $R^6$ and $R^7$ together are $C_{2-3}$alkyl-A.

In certain embodiments, $R^{14}$ is $(R^{15}O)(R^{16}O)P(=O)W$—. In certain such embodiments, D, V, K, and W are absent. In other such embodiments, V and K are absent, D is $C_{1-8}$alkyl, and W is O. In yet other such embodiments, D is $C_{1-8}$alkyl, K is C=O, and V and W are O.

In certain embodiments, $R^{14}$ is $R^{15}GB$—. In preferred embodiments, B is C=O, G is O, D is $C_{1-8}$alkyl, V is O, and K is C=O.

In certain embodiments, $R^{14}$ is heterocyclyl-. In preferred such embodiments, D is $C_{1-8}$alkyl. In certain such embodiments, V is O, K is C=O, and heterocyclyl is oxodioxolenyl. In other such embodiments, V is absent, K is absent or is C=O, and heterocyclyl is $N(R^{18})(R^{19})$, where $R^{18}$ and $R^{19}$ together are J-T-J, J-WB-J, or B-J-T-J, T is absent or is selected from O, $NR^{17}$, S, SO, $SO_2$, $CHOR^{17}$, $CHCO_2R^{15}$, C=O, $CF_2$, and CHF, and J is absent or is $C_{1-3}$alkyl.

In certain embodiments, $R^{14}$ is $(R^{17})_2N$— or $(R^{17})_3N^+$—, and preferably V is absent. In preferred such embodiments, D is $C_{1-8}$alkyl and K is absent or C=O. In certain embodiments where V is absent and $R^{14}$ is $(R^{17})_2N$—, D is absent K is absent or is C=O, preferably K is C=O.

In certain embodiments, $R^{14}$ is $R^{17}SO_2GBG$—. In preferred such embodiments, B is C=O, D, V, and K are absent, and G is NH or $NC_{1-6}$alkyl.

In certain embodiments, $R^{14}$ is $R^{15}GBC_{1-8}alkyl-$. In preferred embodiments, B is C=O, G is O, and the $C_{1-8}alkyl$ moiety is optionally substituted with OH, $C_{1-8}alkyl$ (optionally substituted with halogen, preferably fluorine), $C_{1-8}alkylW$, aryl, heteroaryl, carbocyclyl, heterocyclyl, and $C_{1-6}aralkyl$. In certain such embodiments, the $C_{1-8}alkyl$ moiety is an unsubstituted, mono-, or disubstituted $C_1alkyl$.

In certain embodiments, a compound of formula I has the following stereochemistry:

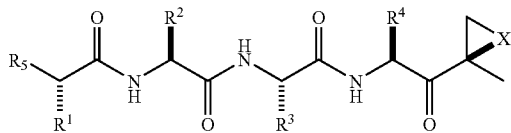

In preferred embodiments, the inhibitor has a structure of formula II or a pharmaceutically acceptable salt thereof, (II)

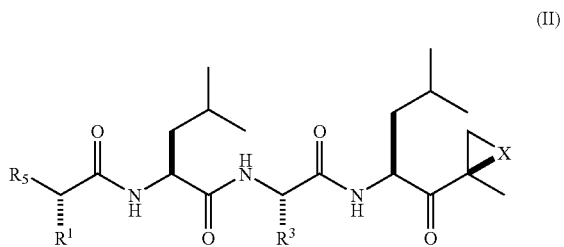

wherein
each A is independently selected from C=O, C=S, and $SO_2$, preferably C=O;
each B is independently selected from C=O, C=S, and $SO_2$, preferably C=O;
D is absent or is $C_{1-8}alkyl$;
G is selected from O, NH, and N—$C_{1-6}alkyl$;
K is absent or is selected from from C=O, C=S, and $SO_2$, preferably K is absent or is C=O;
L is absent or is selected from C=O, C=S, and $SO_2$, preferably L is absent or C=O;
M is absent or is $C_{1-8}alkyl$;
Q is absent or is selected from O, NH, and N—$C_{1-6}alkyl$, preferably Q is absent, O, or NH, most preferably Q is absent or O;
X is selected from O, S, NH, and N—$C_{1-6}alkyl$, preferably O;
each V is independently absent or is selected from O, S, NH, and N—$C_{1-6}alkyl$, preferably V is absent or O;
W is absent or is independently selected from O, S, NH, and N—$C_{1-6}alkyl$, preferably O;
Y is absent or is selected from O, NH, N—$C_{1-6}alkyl$, S, SO, $SO_2$, $CHOR^{10}$, and $CHCO_2R^{10}$;
each Z is independently selected from O, S, NH, and N—$C_{1-6}alkyl$, preferably O;
$R^1$ and $R^3$ are each independently selected from $C_{1-6}alkyl$, $C_{1-6}hydroxyalkyl$, $C_{1-6}alkoxyalkyl$, aryl, $C_{1-6}aralkyl$, and $R^{14}DVKOC_{1-3}alkyl-$, wherein at least one of $R^1$ and $R^3$ is $R^{14}DVKOC_{1-3}alkyl-$;
$R^5$ is $N(R^6)LQR^7$;
$R^6$ is selected from hydrogen, OH, and $C_{1-6}alkyl$, preferably $C_{1-6}alkyl$;
$R^7$ is a further chain of amino acids, hydrogen, a protecting group, aryl, or heteroaryl, any of which is optionally substituted with halogen, carbonyl, nitro, hydroxy, aryl, $C_{1-5}alkyl$; or $R^7$ is selected from $C_{1-6}alkyl$, $C_{1-6}alkenyl$, $C_{1-6}alkynyl$, $C_{1-6}aralkyl$, $C_{1-6}heteroaralkyl$, $R^8ZA—C_{1-8}alkyl-$, $R^{11}Z—C_{1-8}alkyl-$, $(R^8O)(R^9O)P(=O)O—C_{1-8}alkyl-ZAZ—C_{1-8}alkyl-$, $(R^8O)(R^9O)P(=O)O—C_{1-8}alkyl-Z—C_{1-8}alkyl-$, $R^8ZA—C_{1-8}alkyl-ZAZ—C_{1-8}alkyl-$, heterocyclylMZAZ-$C_{1-8}alkyl-$, $(R^8O)(R^9O)P(=O)O—C_{1-8}alkyl-$, $(R^{10})_2N—C_{1-8}alkyl-,)(R^{10})_3N^+—C_{1-8}alkyl-$, heterocyclylM-, carbocyclylM-, $R^{11}SO_2C_{1-8}alkyl-$, and $R^{11}SO_2NH$; or
$R^6$ and $R^7$ together are $C_{1-6}alkyl-Y—C_{1-6}alkyl$, $C_{1-6}alkyl-ZA—C_{1-6}alkyl$, $A—C_{1-6}alkyl-ZA—C_{1-6}alkyl$, $A—C_{1-6}alkyl-A$, or $C_{1-6}alkyl-A$, preferably $C_{1-2}alkyl-Y—C_{1-2}alkyl$, $C_{1-2}alkyl-ZA—C_{1-2}alkyl$, $A—C_{1-2}alkyl-ZA—C_{1-2}alkyl$, $A—C_{1-3}alkyl-A$, or $C_{1-4}alkyl-A$, thereby forming a ring;
$R^8$ and $R^9$ are independently selected from hydrogen, metal cation, $C_{1-6}alkyl$, $C_{1-6}alkenyl$, $C_{1-6}alkynyl$, aryl, heteroaryl, $C_{1-6}aralkyl$, and $C_{1-6}heteroaralkyl$, preferably from hydrogen, metal cation, and $C_{1-6}alkyl$, or $R^8$ and $R^9$ together are $C_{1-6}alkyl$, thereby forming a ring;
each $R^{10}$ is independently selected from hydrogen and $C_{1-6}alkyl$, preferably $C_{1-6}alkyl$; and
each $R^{11}$ is independently selected from hydrogen, $OR^{10}$, $C_{1-6}alkyl$, $C_{1-6}alkenyl$, $C_{1-6}alkynyl$, carbocyclyl, heterocyclyl, aryl, heteroaryl, $C_{1-6}aralkyl$, and $C_{1-6}heteroaralkyl$;
$R^{14}$ is selected from hydrogen, $(R^{15}O)(R^{16}O)P(=O)W—$, $R^{15}GB—$, heterocyclyl-, $(R^{17})_2N—$, $(R^{17})_3N^+—$, $R^{17}SO_2GBG—$, and $R^{15}GBC_{1-8}alkyl-$ where the $C_{1-8}alkyl$ moiety is optionally substituted with OH, $C_{1-8}alkylW$ (optionally substituted with halogen, preferably fluorine), aryl, heteroaryl, carbocyclyl, heterocyclyl, and $C_{1-6}aralkyl$, preferably at least one occurrence of $R^{14}$ is other than hydrogen;
$R^{15}$ and $R^{16}$ are independently selected from hydrogen, metal cation, $C_{1-6}alkyl$, $C_{1-6}alkenyl$, $C_{1-6}alkynyl$, aryl, heteroaryl, $C_{1-6}aralkyl$, and $C_{1-6}heteroaralkyl$, preferably from hydrogen, metal cation, and $C_{1-6}alkyl$, or $R^{15}$ and $R^{16}$ together are $C_{1-6}alkyl$, thereby forming a ring;
each $R^{17}$ is independently selected from hydrogen, $OR^{10}$, $C_{1-6}alkyl$, $C_{1-6}alkenyl$, $C_{1-6}alkynyl$, carbocyclyl, heterocyclyl, aryl, heteroaryl, $C_{1-6}aralkyl$, and $C_{1-6}heteroaralkyl$;
provided that when $R_6$ is H, L is C=O, and Q is absent, $R^7$ is not hydrogen, $C_{1-6}alkyl$, or substituted or unsubstituted aryl or heteroaryl; and
D, G, V, K, and W are selected such that there are no O—O, N—O, S—N, or S—O bonds.

In certain embodiments, $R^1$ and $R^3$ are each independently selected from $C_{1-6}alkyl$, $C_{1-6}hydroxyalkyl$, $C_{1-6}alkoxyalkyl$, aryl, $C_{1-6}aralkyl$, and $R^{14}DVKOC_{1-3}alkyl-$ wherein at least one of $R^1$ and $R^3$ is $R^{14}DVKOC_{1-3}alkyl-$. In preferred embodiments, one of $R^1$ and $R^3$ is $C_{1-6}aralkyl$ and the other is $R^{14}DVKOC_{1-3}alkyl-$. In the most preferred embodiment, one of $R^1$ and $R^3$ is 2-phenylethyl or phenylmethyl and the other is $R^{14}DVKOCH_2—$ or $R^{14}DVKO(CH_3)CH—$.

In certain embodiments, each $R^{11}$ is independently selected from hydrogen, $C_{1-6}alkyl$, $C_{1-6}alkenyl$, $C_{1-6}alkynyl$, carbocyclyl, heterocyclyl, aryl, heteroaryl, $C_{1-6}aralkyl$, and $C_{1-6}heteroaralkyl$.

In certain embodiments, each $R^{17}$ is independently selected from hydrogen, $C_{1-6}alkyl$, $C_{1-6}alkenyl$, $C_{1-6}alkynyl$, carbocyclyl, heterocyclyl, aryl, heteroaryl, $C_{1-6}aralkyl$, and $C_{1-6}heteroaralkyl$.

In certain embodiments, L and Q are absent and $R^7$ is selected from hydrogen, a further chain of amino acids, $C_{1-6}acyl$, a protecting group, aryl, heteroaryl, $C_{1-6}alkyl$, $C_{1-6}$alkenyl, $C_{1-6}$alkynyl, $C_{1-6}$aralkyl, and $C_{1-6}$heteroaralkyl. In certain such embodiments, $R^6$ is $C_{1-6}$alkyl and $R^7$ is selected from butyl, allyl, propargyl, phenylmethyl, 2-pyridyl, 3-pyridyl, and 4-pyridyl.

In other embodiments, L is $SO_2$, Q is absent, and $R^7$ is selected from $C_{1-6}$alkyl and aryl. In certain such embodiments, $R^7$ is selected from methyl and phenyl.

In certain embodiments, L is C=O and $R^7$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8$ZA—$C_{1-8}$alkyl-, $R^{11}$Z—$C_{1-8}$alkyl-, ($R^8$O)($R^9$O)P(=O)O—$C_{1-8}$alkyl-, ($R^8$O)($R^9$O)P(=O)O—$C_{1-8}$alkyl-ZAZ—$C_{1-8}$alkyl-, ($R^8$O)($R^9$O)P(=O)O—$C_{1-8}$alkyl-Z—$C_{1-8}$alkyl-, $R^8$ZA—$C_{1-8}$alkyl-ZAZ—$C_{1-8}$alkyl-, heterocyclylMZAZ-$C_{1-8}$alkyl-, ($R^{10}$)$_2$N—$C_{1-8}$alkyl-, ($R^{10}$)$_3$N$^+$—$C_{1-8}$alkyl-, heterocyclylM-, carbocyclylM-, $R^{11}$SO$_2$C$_{1-8}$alkyl-, and $R^{11}$SO$_2$NH—. In certain embodiments, L is C=O, Q is absent, and $R^7$ is H.

In certain embodiments, $R^6$ is $C_{1-6}$alkyl, $R^7$ is $C_{1-6}$alkyl, Q is absent, and L is C=O. In certain such embodiments, $R^7$ is ethyl, isopropyl, 2,2,2-trifluoroethyl, or 2-(methylsulfonyl)ethyl.

In other embodiments, L is C=O, Q is absent, and $R^7$ is $C_{1-66}$aralkyl. In certain such embodiments, $R^7$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^6$ is $C_{1-6}$alkyl, and $R^7$ is aryl. In certain such embodiments, $R^7$ is substituted or unsubstituted phenyl.

In certain embodiments, L is C=O, Q is absent or O, and $R^7$ is —(CH$_2$)$_n$carbocyclyl. In certain such embodiments, $R^7$ is cyclopropyl or cyclohexyl.

In certain embodiments, L and A are C=O, Q is absent, Z is O, and $R^7$ is selected from $R^8$ZA—$C_{1-8}$alkyl-, $R^{11}$Z—$C_{1-8}$alkyl-, $R^8$ZA—$C_{1-8}$alkyl-ZAZ—$C_{1-8}$alkyl-, ($R^8$O)($R^9$O)P(=O)O—$C_{1-8}$alkyl-ZAZ—$C_{1-8}$alkyl-, ($R^8$O)($R^9$O)P(=O)O—$C_{1-8}$alkyl-Z—$C_{1-8}$alkyl-, and heterocyclylMZAZ-$C_{1-8}$alkyl-. In certain such embodiments, $R^7$ is heterocyclylM-ZAZ-$C_{1-8}$alkyl- where heterocyclyl is substituted or unsubstituted oxodioxolenyl or N($R^{12}$)($R^{13}$), wherein $R^{12}$ and $R^{13}$ together are $C_{1-6}$alkyl-Y—$C_{1-6}$alkyl, preferably $C_{1-3}$alkyl-Y—$C_{1-3}$alkyl, thereby forming a ring.

In certain preferred embodiments, L is C=O, Q is absent, and $R^7$ is selected from ($R^8$O)($R^9$O)P(=O)O—$C_{1-8}$alkyl-, ($R^{10}$)$_2$NC$_{1-8}$alkyl, ($R^{10}$)$_3$N$^+$(CH$_2$)$_n$—, and heterocyclyl-M-. In certain such embodiments, $R^7$ is —$C_{1-8}$alkylN($R^{10}$)$_2$ or —$C_{1-8}$alkylN$^+$($R^{10}$)$_3$, where $R^{10}$ is $C_{1-6}$alkyl. In certain other such embodiments, $R^7$ is heterocyclylM-, where heterocyclyl is selected from morpholino, piperidino, piperazino, and pyrrolidino.

In certain embodiments, L is C=O, $R^6$ is $C_{1-6}$alklyl, Q is selected from O and NH and $R^7$ is selected from $C_{1-6}$alkyl, cycloalkyl-M, $C_{1-6}$araalkyl, and $C_{1-6}$heteroaraalkyl. In other embodiments, L is C=O, $R^6$ is $C_{1-6}$alkyl, Q is selected from O and NH, and $R^7$ is $C_{1-6}$alkyl, where $C_{1-6}$alkyl is selected from methyl, ethyl, and isopropyl. In further embodiments, L is C=O, $R^6$ is $C_{1-6}$alkyl, Q is selected from O and NH and $R^7$ is $C_{1-6}$aralkyl, where aralkyl is phenylmethyl. In other embodiments, L is C=O, $R^6$ is $C_{1-6}$alkyl, Q is selected from O and NH, and $R^7$ is $C_{1-6}$heteroaralkyl, where heteroaralkyl is (4-pyridyl)methyl.

In certain embodiments, L is absent or is C=O, and $R^6$ and $R^7$ together are $C_{1-6}$alkyl-Y—$C_{1-6}$alkyl, $C_{1-6}$alkyl-ZA—$C_{1-6}$alkyl, or $C_{1-6}$alkyl-A, thereby forming a ring. In certain preferred embodiments, L is C=O, Q is absent, and $R^6$ and $R^7$ together are $C_{1-3}$alkyl-Y—$C_{1-3}$alkyl. In another preferred embodiment, L and Q are absent, and $R^6$ and $R^7$ together are $C_{1-3}$alkyl-Y—$C_{1-3}$alkyl. In another preferred embodiment, L is C=O, Q is absent, Y is selected from NH and N—$C_{1-6}$alkyl, and $R^6$ and $R^7$ together are $C_{1-3}$alkyl-Y—$C_{1-3}$alkyl. In another preferred embodiment, L is C=O, Y is absent, and $R^6$ and $R^7$ together are $C_{1-3}$alkyl-Y—$C_{1-3}$alkyl. In another preferred embodiment, L and A are C=O, and $R^6$ and $R^7$ together are $C_{1-2}$alkyl-ZA—$C_{1-2}$alkyl. In another preferred embodiment, L and A are C=O and $R^6$ and $R^7$ together are $C_{2-3}$alkyl-A.

In certain embodiments, $R^{14}$ is ($R^{15}$O)($R^{16}$O)P(=O)W—. In certain such embodiments, D, V, K, and W are absent. In other such embodiments, V and K are absent, D is $C_{1-8}$alkyl, and W is O. In yet other such embodiments, D is $C_{1-8}$alkyl, K is C=O, and V and W are O.

In certain embodiments, $R^{14}$ is $R^{15}$GB—. In preferred embodiments, B is C=O, G is O, D is $C_{1-8}$alkyl, V is O, and K is C=O.

In certain embodiments, $R^{14}$ is heterocyclyl-. In preferred such embodiments, D is $C_{1-8}$alkyl. In certain such embodiments, V is O, K is C=O, and heterocyclyl is oxodioxolenyl. In other such embodiments, V is absent, K is absent or is C=O, and heterocyclyl is N($R^{18}$)($R^{19}$), where $R^{18}$ and $R^{19}$ together are J-T-J, J-WB-J, or B-J-T-J, T is absent or is selected from O, NR$^{17}$, S, SO, SO$_2$, CHOR$^{17}$, CHCO$_2$R$^{15}$, C=O, CF$_2$, and CHF, and J is absent or is $C_{1-3}$alkyl.

In certain embodiments, $R^{14}$ is ($R^{17}$)$_2$N— or ($R^{17}$)$_3$N$^+$—, and preferably V is absent. In preferred such embodiments, D is $C_{1-8}$alkyl and K is absent or C=O. In certain embodiments where V is absent and $R^{14}$ is ($R^{17}$)$_2$N—, D is absent K is absent or is C=O, preferably K is C=O.

In certain embodiments, $R^{14}$ is $R^{17}$SO$_2$GBG—. In preferred such embodiments, B is C=O, D, V, and K are absent, and G is NH or NC$_{1-6}$alkyl.

In certain embodiments, $R^{14}$ is $R^{15}$GBC$_{1-8}$alkyl-. In preferred such embodiments, B is C=O, G is O, and the $C_{1-8}$alkyl moiety is optionally substituted with OH, $C_{1-8}$alkyl (optionally substituted with halogen, preferably fluorine), $C_{1-8}$alkylW, aryl, heteroaryl, carbocyclyl, heterocyclyl, and $C_{1-6}$aralkyl. In certain such embodiments, the $C_{1-8}$alkyl moiety is an unsubstituted, mono-, or disubstituted $C_1$alkyl.

Another aspect of the invention relates to compounds having a structure of formula (III) or formula (IV) or a pharmaceutically acceptable salt thereof,

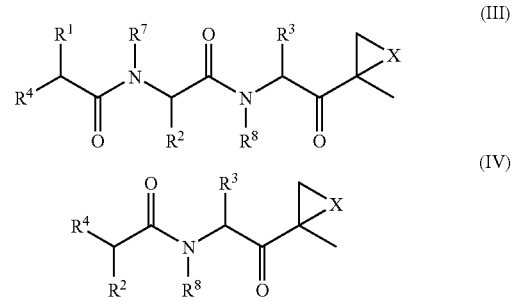

wherein
each Ar is independently an aromatic or heteroaromatic group optionally substituted with 1 to 4 substituents;
L is absent or is selected from C=O, C=S, and SO$_2$, preferably SO$_2$ or C=O;
X is selected from O, S, NH, and N—$C_{1-6}$alkyl, preferably O;
Y is absent or is selected from C=O and SO$_2$;
Z is absent or is $C_{1-6}$alkyl;

$R^1$, $R^2$, and $R^3$ are each independently selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-6}$alkyl ester $C_{1-5}$ alkyl ester, and aryl ester), thiol, or thioether substituents;

$R^4$ is $N(R^5)L-Z-R^6$;

$R^5$ is selected from hydrogen, OH, $C_{1-6}$aralkyl-Y—, and $C_{1-6}$alkyl-Y—, preferably hydrogen;

$R^6$ is selected from hydrogen, $OR^7$, $C_{1-6}$alkenyl, Ar—Y—, carbocyclyl, and heterocyclyl; and $R^7$ and $R^8$ are independently selected from hydrogen, $C_{1-6}$alkyl, and $C_{1-6}$aralkyl, preferably hydrogen.

In certain embodiments, L is selected from C=O, C=S, and $SO_2$, preferably $SO_2$ or C=O.

In certain embodiments, $R^5$ is selected from hydrogen, OH, $C_{1-6}$aralkyl, and $C_{1-6}$alkyl, preferably hydrogen.

In certain embodiments, $R^6$ is selected from hydrogen, $C_{1-6}$alkenyl, Ar—Y—, carbocyclyl, and heterocyclyl.

In certain embodiments, X is O and $R^1$, $R^2$, and $R^3$ are each independently selected from $C_{1-6}$alkyl, $C_{1-6}$hydroxyalkyl, and $C_{1-6}$aralkyl. In preferred such embodiments, $R^1$ and $R^3$ are independently $C_{1-6}$alkyl and $R^2$ is $C_{1-6}$aralkyl. In more preferred such embodiments, $R^1$ and $R^3$ are both isobutyl and $R^2$ is phenylmethyl.

In certain embodiments, $R^5$ is hydrogen, L is C=O or $SO_2$, $R^6$ is Ar—Y—, and each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar—Q—, where Q is selected from a direct bond, —O—, and $C_{1-6}$alkyl. In certain other such embodiments where Z is $C_{1-6}$alkyl, Z may be substituted, preferably with Ar, e.g., phenyl.

In certain embodiments, $R^5$ is hydrogen, Z is absent, L is C=O or $SO_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments, Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or $SO_2$, Z is absent, and $R^6$ is $C_{1-6}$alkenyl, where $C_{1-6}$alkenyl is a substituted vinyl group where the substituent is preferably an aryl or heteroaryl group, more preferably a phenyl group optionally substituted with one to four substituents.

In certain embodiments, $R^7$ and $R^8$ are independently selected from hydrogen and $C_{1-6}$alkyl. In certain preferred such embodiments, $R^7$ and $R^8$ are independently selected from hydrogen and methyl. In more preferred such embodiments, $R^7$ and $R^8$ are both hydrogen.

In certain embodiments, a compound of formula (III) or formula (IV) has the following stereochemistry

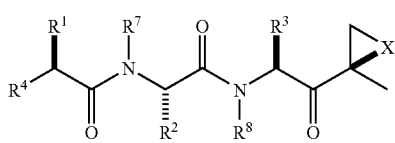
(III)

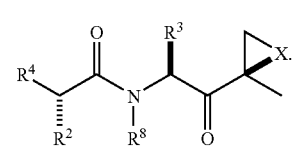
(IV)

In preferred embodiments, the inhibitor has a structure of formula (V) or formula (VI) or a pharmaceutically acceptable salt thereof,

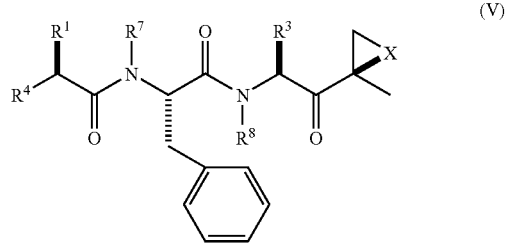
(V)

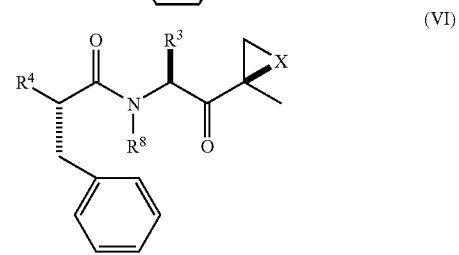
(VI)

wherein each Ar is independently an aromatic or heteroaromatic group optionally substituted with 1-4 substituents;

L is absent or is selected from C=O, C=S, and $SO_2$, preferably $SO_2$ or C=O;

X is selected from O, S, NH, and N—$C_{1-6}$alkyl, preferably O;

Y is absent or is selected from C=O and $SO_2$;

Z is absent or is $C_{1-6}$alkyl;

$R^1$ and $R^3$ are each independently selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-5}$ alkyl ester and aryl ester), thiol, or thioether substituents;

$R^4$ is $N(R^5)L-Z-R^6$;

$R^5$ is selected from hydrogen, OH, $C_{1-6}$aralkyl-Y—, and $C_{1-6}$alkyl-Y—, preferably hydrogen;

$R^6$ is selected from hydrogen, $OR^7$, $C_{1-6}$alkenyl, Ar—Y—, carbocyclyl, and heterocyclyl; and $R^7$ and $R^8$ are independently selected from hydrogen, $C_{1-6}$alkyl, and $C_{1-6}$aralkyl, preferably hydrogen.

In certain embodiments, L is selected from C=O, C=S, and $SO_2$, preferably $SO_2$ or C=O.

In certain embodiments, $R^5$ is selected from hydrogen, OH, $C_{1-6}$aralkyl, and $C_{1-6}$alkyl, preferably hydrogen.

In certain embodiments, $R^6$ is selected from hydrogen, $C_{1-6}$alkenyl, Ar—Y—, carbocyclyl, and heterocyclyl.

In certain embodiments, X is O and $R^1$ and $R^3$ are each independently selected from $C_{1-6}$alkyl, $C_{1-6}$hydroxyalkyl, and $C_{1-6}$aralkyl. In preferred such embodiments, $R^1$ and $R^3$ are independently $C_{1-6}$alkyl. In more preferred such embodiments, $R^1$ and $R^3$ are isobutyl.

In certain embodiments, $R^5$ is hydrogen, L is C=O or $SO_2$, and $R^6$ is Ar—Y—, each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar—Q—, where Q is selected from a direct bond, —O—, and $C_{1-6}$alkyl. In certain other such embodiments where Z is $C_{1-6}$alkyl, Z may be substituted, e.g., preferably with Ar, more preferably with phenyl.

In certain embodiments, $R^5$ is hydrogen, Z is absent, L is C=O or $SO_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or $SO_2$, Z is absent, and $R^6$ is $C_{1-6}$alkenyl, where $C_{1-6}$alkenyl is a substituted vinyl group where the substituent is preferably an aryl or heteroaryl group, more preferably the substituent is a phenyl group optionally substituted with one to four substituents.

In certain embodiments, $R^7$ and $R^8$ are independently selected from hydrogen and $C_{1-6}$alkyl. In certain preferred such embodiments, $R^7$ and $R^8$ are independently selected from hydrogen and methyl. In more preferred such embodiments, $R^7$ and $R^8$ are both hydrogen.

In certain embodiments, —L—Z—$R^6$ is selected from

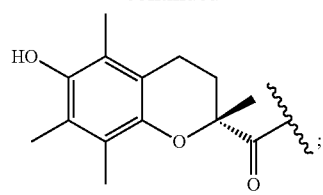

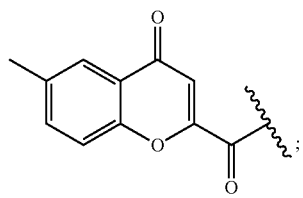

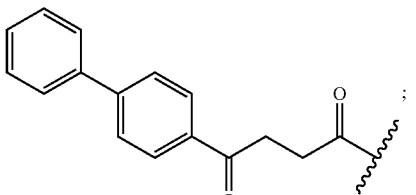

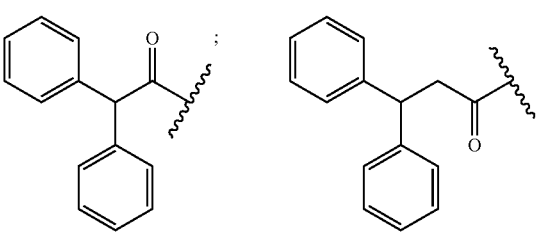

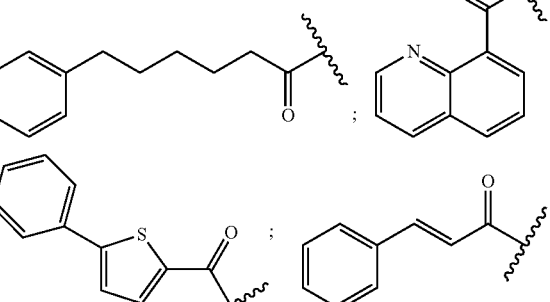

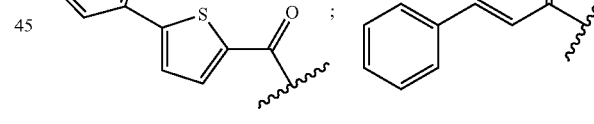

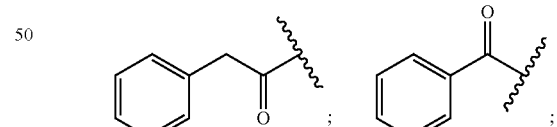

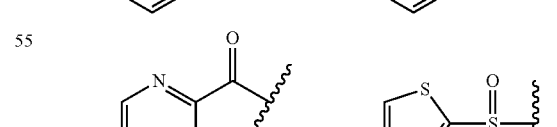

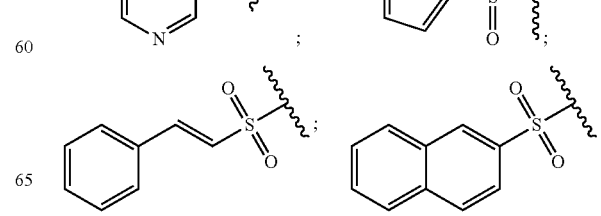

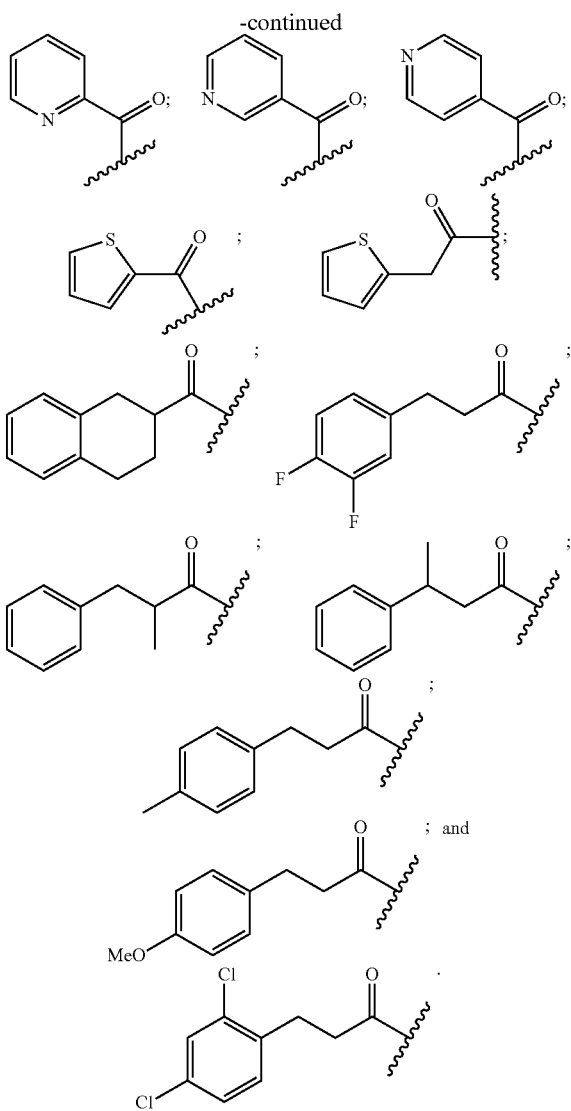

One aspect of the invention relates to a medical device including composition disclosed herein that include an inhibitor having a structure of any one of formulae I to VI. In one embodiment, the composition is incorporated within a medical device. In certain embodiments, the medical device is a gel comprising a polymer matrix or ceramic matrix and an inhibitor. Said polymer can be either naturally occurring or synthetic. In another embodiment, said gel serves as a drug depot, an adhesive, a suture, a barrier or a sealant.

Another aspect of the invention relates to a medical device comprising a substrate having a surface onto which an inhibitor having a structure of any one of formulae I to VI is disposed. In one embodiment, the inhibitor is directly disposed on a medical device. In another embodiment, a coating is so disposed, the coating comprising a polymer matrix or ceramic matrix with an inhibitor having a structure of any one of formulae I to VI dispersed or dissolved therein.

In one embodiment, the medical device is a coronary, vascular, peripheral, or biliary stent. More particularly, the stent of the present invention is an expandable stent. When coated with a matrix containing an inhibitor having a structure any one of formulae I to VI, the matrix is flexible to accommodate compressed and expanded states of such an expandable stent.

In another embodiment of this invention, the stent has at least a portion which is insertable or implantable into the body of a patient, wherein the portion has a surface which is adapted for exposure to body tissue and wherein at least a part of the surface is coated with an inhibitor having a structure of any one of formulae I to VI, or a coating comprising a matrix having an inhibitor having a structure of any one of formulae I to VI is dispersed or dissolved therein. An example of a suitable stent is disclosed in U.S. Pat. No. 4,733,665, which is incorporated herein by reference in its entirety.

In another embodiment, the medical device of the present invention is a surgical implement such as a vascular implant, an intraluminal device, surgical sealant or a vascular support. More particularly, the medical device of the present invention is a catheter, an implantable vascular access port, a central venous catheter, an arterial catheter, a vascular graft, an intraaortic balloon pump, a suture, a ventricular assist pump, a drug-eluting barrier, an adhesive, a vascular wrap, an extra/perivascular support, a blood filter, or a filter adapted for deployment in a blood vessel, coated with an inhibitor having a structure of any one of formulae I to VI either directly or by a matrix containing an inhibitor having a structure of any one of formulae I to VI.

In certain embodiments, the intraluminal medical device is coated with an inhibitor having a structure of any one of formulae I to VI or a coating comprising biologically tolerated matrix and an inhibitor having a structure of any one of formulae I to VI dispersed in the polymer, said device having an interior surface and an exterior surface, having the coating applied to at least a part of the interior surface, the exterior surface, or both.

In certain embodiments, the medical device may be useful to prevent restenosis after angioplasty. The medical device may also be useful for the treatment of various diseases and conditions by providing localized administration of an inhibitor having a structure of any one of formulae I to VI. Such diseases and conditions include restenosis, inflammation, rheumatoid arthritis, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection and proliferation. Examples of diseases and conditions that are subject to a treatment including the drug coated medical devices of the present invention include atherosclerosis, acute coronary syndrome, Alzheimer's disease, cancer, fever, muscle disuse (atrophy), denervation, vascular occlusions, stroke, HIV infection, nerve injury, renal failure associated with acidosis, and hepatic failure. See, e.g., Goldberg, U.S. Pat. No. 5,340,736.

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

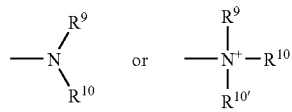

wherein $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, the amino group is basic, meaning the protonated form has a $pK_a \geq 7.00$.

The terms "amide" and "amido" are art-recognized as an amino-substituted carbonyl and includes a moiety that can be represented by the general formula:

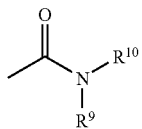

wherein $R^9$, $R^{10}$ are as defined above. Preferred embodiments of the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

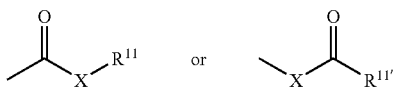

wherein X is a bond or represents an oxygen or a sulfur, and $R^{11}$ represents a hydrogen, an alkyl, an alkenyl, —$(CH_2)_m$—$R^8$ or a pharmaceutically acceptable salt, $R^{11'}$ represents a hydrogen, an alkyl, an alkenyl or —$(CH_2)_m$—$R^8$, where m and $R^8$ are as defined above. Where X is an oxygen and $R^{11}$ or $R^{11'}$ is not hydrogen, the formula represents an "ester". Where X is an oxygen, and $R^{11}$ is a hydrogen, the formula represents a "carboxylic acid".

As used herein, "enzyme" can be any partially or wholly proteinaceous molecule which carries out a chemical reaction in a catalytic manner. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially-generated mutant enzymes, enzymes with side chain or backbone modifications, enzymes having leader sequences, and enzymes complexed with non-proteinaceous material, such as proteoglycans, proteoliposomes. Enzymes can be made by any means, including natural expression, promoted expression, cloning, various solution-based and solid-based peptide syntheses, and similar methods known to those of skill in the art.

The term "$C_{1-6}$heteroaralkyl", as used herein, refers to a $C_{1-6}$alkyl group substituted with a heteroaryl group.

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "$C_{1-6}$hydroxyalkyl" refers to a $C_{1-6}$alkyl group substituted with a hydroxy group.

As used herein, the term "inhibitor" is meant to describe a compound that blocks or reduces an activity of an enzyme (for example, inhibition of proteolytic cleavage of standard fluorogenic peptide substrates such as suc-LLVY-AMC, Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

As used herein, the term "peptide" includes not only standard amide linkage with standard α-substituents, but commonly utilized peptidomimetics, other modified linkages, non-naturally occurring side chains, and side chain modifications, as detailed below.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "thioether" refers to an alkyl group, as defined above, having a sulfur moiety attached thereto. In preferred embodiments, the "thioether" is represented by —S-alkyl. Representative thioether groups include methylthio, ethylthio, and the like.

As used herein, the term "treating" or "treatment" includes reversing, reducing, or arresting the symptoms, clinical signs, and underlying pathology of a condition in manner to improve or stabilize a subject's condition.

Selectivity for 20S proteasome

The enzyme inhibitors disclosed herein are useful in part because they inhibit the action of the 20S proteasome. Additionally, unlike other 20S proteasome inhibitors, the compounds disclosed herein are highly selective toward the 20S proteasome, with respect to other protease enzymes. That is, the instant compounds show selectivities for the 20S proteasome over other proteases such as cathepsins, calpains, papain, chymotrypsin, trypsin, tripeptidyl pepsidase II. The selectivities of the enzyme inhibitors for 20S proteasome are such that at concentrations below about 50 µM, the enzyme inhibitors show inhibition of the catalytic activity of the 20S proteasome, while not showing inhibition of the catalytic activity of other proteases such as cathepsins, calpains, papain, chymotrypsin, trypsin, tripeptidyl pepsidase II. In preferred embodiments, the enzyme inhibitors show inhibition of the catalytic activity of the 20S proteasome at concentrations below about 10 µM, while not showing inhibition of the catalytic activity of other proteases at these concentrations. In even more preferred embodiments, the enzyme inhibitors show inhibition of the catalytic activity of the 20S proteasome at concentrations below about 1 µM, while not showing inhibition of the catalytic activity of other proteases at these concentrations. Enzyme kinetic assays are disclosed in U.S. application Ser. No. 09/569748, Example 2 and Stein et al., *Biochem.* (1996), 35, 3899-3908.

Selectivity for Chymotrypsin-Like Activity

Particular embodiments of the enzyme inhibiting compounds described herein are further useful because they can efficiently and selectively inhibit the chymotrypsin-like activity of the 20S proteasome, as compared to the trypsin-like, and PGPH activities. The chymotrypsin-like activity of 20S proteasome is characterized by cleavage of peptides in the immediate vicinity of large hydrophobic residues. In particular, the chymotrypsin-like activity of Ntn hydrolases can be determined by cleavage of a standard substrate. Examples of such substrates are known in the art. For example, a leucylvalinyltyrosine derivative can be used. Enzyme kinetic assays are disclosed in U.S. application Ser. No. 09/569748, Example 2 and Stein et al., *Biochem*. (1996), 35, 3899-3908.

Uses of Enzyme Inhibitors

The biological consequences of proteasome inhibition are numerous. At the cellular level, the accumulation of poly-ubiquitinated proteins, cell morphological changes, and apoptosis have been reported upon treatment of cells with various proteasome inhibitors. Proteasome inhibition has also been suggested as a possible antitumor therapeutic strategy. The fact that epoxomicin was initially identified in a screen for antitumor compounds validates the proteasome as an antitumor chemotherapeutic target. Accordingly, these compounds are useful for treating cancer. Proteasome inhibition has also been associated with inhibition of NF-κB activation and stabilization of p53 levels. Thus, compounds of the invention may also be used to inhibit NF-κB activation, and stabilize p53 levels in cell culture. Since NF-κB is a key regulator of inflammation, it is an attractive target for anti-inflammatory therapeutic intervention. Thus, compounds of the invention may be useful for the treatment of conditions associated with chronic inflammation, including, but not limited to COPD, psoriasis, bronchitis, emphysema, and cystic fibrosis.

The disclosed compounds can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins, TGF-β, and transcription factor NF-κB.

Another embodiment of the invention is the use of the compounds disclosed herein for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser (SEQ ID NO.: 1), which is identical to the β-subunit of human macropain (Kojima, S. et al., Fed. Eur. Biochem. Soc., (1992) 304:57-60). The APP-processing enzyme cleaves at the Gln15-Lys16 bond; in the presence of calcium ion, the enzyme also cleaves at the Met1-Asp1 bond, and the Asp1-Ala2 bonds to release the extracellular domain of β-AP.

One embodiment, therefore, is a method of treating Alzheimer's disease, including administering to a subject an effective amount of a compound (e.g., pharmaceutical composition) disclosed herein. Such treatment includes reducing the rate of β-AP processing, reducing the rate of β-AP plaque formation, reducing the rate of β-AP generation, and reducing the clinical signs of Alzheimer's disease.

Other embodiments of the invention relate to cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Inhibitors of the invention are useful for treating conditions such as cancer, chronic infectious diseases, fever, muscle disuse (atrophy) and denervation, nerve injury, fasting, renal failure associated with acidosis, diabetes, and hepatic failure. See, e.g., Goldberg, U.S. Pat. No. 5,340,736. Embodiments of the invention therefore encompass methods for: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a subject) with an effective amount of a compound (e.g., pharmaceutical composition) disclosed herein.

Fibrosis is the excessive and persistant formation of scar tissue resulting from the hyperproliferitive growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activate transcription of target genes upon TGF-β stimulation is regulated by proteasome activity (Xu et al., 2000). However, accelerated degradation of the TGF-β signaling components has been observed in cancers and other hyperproliferative conditions. Thus, certain embodiments of the invention relate to a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstial lung diseases and extrinsic lung disorders). The treatment of burn victims is often hampered by fibrosis, thus, an additional embodiment of the invention is the topical or systemic administration of the inhibitors to treat burns. Wound closure following surgery is often associated with disfiguring scars, which may be prevented by inhibition of fibrosis. Thus, in certain embodiments, the invention relates to a method for the prevention or reduction of scarring.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., *Cell* (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Some embodiments of the invention include methods of affecting the level of expression of IL-2, MHC-I, IL-6, TNFα, IFN-β or any of the other previously-mentioned proteins, each method including administering to a subject an effective amount of a compound disclosed herein. Complexes including p50 are rapid mediators of acute inflammatory and immune responses (Thanos, D. and Maniatis, T., *Cell* (1995) 80:529-532).

NF-κB also participates in the expression of the cell adhesion genes that encode E-selectin, P-selectin, ICAM, and VCAM-1 (Collins, T., *Lab. Invest.* (1993) 68:499-508). One embodiment of the invention is a method for inhibiting cell adhesion (e.g., cell adhesion mediated by E-selectin, P-selectin, ICAM, or VCAM-1), including contacting a cell with (or administering to a subject) an effective amount of a compound (or a pharmaceutical composition) disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB (Koong et al., 1994). It has been demonstrated that the severity of injury resulting in hypoxia can be reduced with the administration of a proteasome inhibitor (Gao et al., 2000; Bao et al., 2001; Pye et al., 2003). Therefore, certain embodiments of the invention relate to a method of treating an ischemic condition or reperfusion injury comprising administering to a subject in need of such treatment an effective amount of a compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., *Science*, (1995) 267:960). Two embodiments of the invention are a method for inhibiting or reducing HIV infection in a subject, and a method for decreasing the level of viral gene expression, each method including administering to the subject an effective amount of a compound disclosed herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., *J. Immun.* (2003) 171: 1515-1525). Therefore, in certain embodiments, compounds of the invention may be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a compound described herein. A compound of the invention may be used to treat immune-related conditions such as allergy, asthma, organ/tissue rejection (graft-versus-host disease), and auto-immune diseases, including, but not limited to, lupus, rheumatoid arthritis, psoriasis, multiple sclerosis, and inflammatory bowel diseases (such as ulcerative colitis and Crohn's disease). Thus, a further embodiment is a method for suppressing the immune system of a subject (e.g., inhibiting transplant rejection, allergies, auto-immune diseases, and asthma), including administering to the subject an effective amount of a compound described herein.

Another further embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. *Cell* (1994) 78:773-785; and Traenckner, et al., *EMBO J.* (1994) 13:5433-5441). One embodiment of the invention is a method for inhibiting IκB-α degradation, including contacting the cell with a compound described herein. A further embodiment is a method for reducing the cellular content of NF-κB in a cell, muscle, organ, or subject, including contacting the cell, muscle, organ, or subject with a compound described herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Other embodiments of the invention are methods for affecting cyclin-dependent eukaryotic cell cycles, including exposing a cell (in vitro or in vivo) to a compound disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with p34.sup.cdc2 protein kinase or related kinases. The proteolysis targeting signal is localized to amino acids 42-RAALGNISEN-50 (destruction box). There is evidence that cyclin is converted to a form vulnerable to a ubiquitin ligase or that a cyclin-specific ligase is activated during mitosis (Ciechanover, A., Cell, (1994) 79:13-21). Inhibition of the proteasome inhibits cyclin degradation, and therefore inhibits cell proliferation, for example, in cyclin-related cancers (Kumatori et al., Proc. Natl. Acad. Sci. USA (1990) 87:7071-7075). One embodiment of the invention is a method for treating a proliferative disease in a subject (e.g., cancer, psoriasis, or restenosis), including administering to the subject an effective amount of a compound disclosed herein. The invention also encompasses a method for treating cyclin-related inflammation in a subject, including adminstering to a subject a therapeutically effective amount of a compound described herein.

Additional embodiments are methods for affecting the proteasome-dependent regulation of oncoproteins and methods of treating or inhibiting cancer growth, each method including exposing a cell (in vivo, e.g., in a subject, or in vitro) to a compound disclosed herein. HPV-16 and HPV-18-derived E6 proteins stimulate ATP-and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject an effective amount of a compound disclosed herein.

In another embodiment, the disclosed compounds are useful for the treatment of a parasitic infection, such as infections caused by protozoan parasites. The proteasome of these parasites is considered to be involved primarily in cell differentiation and replication activities (Paugam et al., Trends Parasitol. 2003, 19(2): 55-59). Furthermore, entamoeba species have been shown to lose encystation capacity when exposed to proteasome inhibitors (Gonzales, et al., Arch. Med. Res. 1997, 28, Spec No: 139-140). In certain such embodiments, the disclosed compounds are useful for the treatment of parasitic infections in humans caused by a protozoan parasite selected from Plasmodium sps. (including P. falciparum, P. vivax, P. malariae, and P. ovale, which cause malaria), Trypanosoma sps. (including T. cruzi, which causes Chagas' disease, and T. brucei which causes African sleeping sickness), Leishmania sps. (including L. amazonensis, L. donovani, L. infantum, L. mexicana, etc.), Pneumocystis carinii (a protozoan known to cause pneumonia in AIDS and other immunosuppressed patients), Toxoplasma gondii, Entamoeba histolytica, Entamoeba invadens, and Giardia lamblia. In certain embodiments, the disclosed compounds are useful for the treatment of parasitic infections in animals and livestock caused by a protozoan parasite selected from Plasmodium hermani, Cryptosporidium sps., Echinococcus granulosus, Eimeria tenella, Sarcocystis neurona, and Neurospora crassa. Other compounds useful as proteasome inhibitors in the treatment of parasitic diseases are described in WO 98/10779, which is incorporated herein in its entirety.

In certain embodiments, the disclosed compounds inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., J. Clin. Invest. (2003) 111: 1771-1782), therefore suggesting that the ubiquitin-proteasome machinery regulates osteoblast differentiation and bone formation. Therefore, the disclosed compounds may be useful in the treatment and/or prevention of diseases associated with bone loss, such as osteroporosis.

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., Trans Genet (1992) 8:55-61 describes evidence that bone morphogenetic proteins (BMPs), are differentially expressed in hair follicles during development. Harris, S. E., et al., J Bone Miner Res (1994) 9:855-863 describes the effects of TGFβ on expression of BMP-2 and other substances in bone cells. BMP-2 expression in mature follicles also occurs during maturation and after the period of cell proliferation (Hardy, et al. (1992, supra). Thus, compounds of the invention may also be useful for hair follicle growth stimulation.

Finally, the disclosed compounds are also useful as diagnostic agents (e.g., in diagnostic kits or for use in clinical laboratories) for screening for proteins (e.g., enzymes, transcription factors) processed by Ntn hydrolases, including the proteasome. The disclosed compounds are also useful as research reagents for specifically binding the X/MB1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a compound disclosed herein; exposing the compound-exposed organism, cell preparation, or cell extract to a signal, and monitoring the process or output. The high selectivity of the compounds disclosed herein permits rapid and accurate elimination or implication of the Ntn (for example, the 20S proteasome) in a given cellular, developmental, or physiological process.

Administration

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Another aspect of the invention provides a conjoint therapy wherein one or more other therapeutic agents are administered with the proteasome inhibitor. Such conjoint treatment may be achieved by way of the simultaneous, sequential, or separate dosing of the individual components of the treatment.

In certain embodiments, a compound of the invention is conjointly administered with one or more other proteasome inhibitor(s).

In certain embodiments, a compound of the invention is conjointly administered with a chemotherapeutic. Suitable chemotherapeutics may include, natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); and platinum coordination complexes (cisplatin, carboplatin), procarbazine, hydroxyurea, mitotane, aminoglutethimide; hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a compound of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a compound of the invention is conjointly administered with an immunotherapeutic agent. Suitable immunotherapeutic agents may include, but are not limited to, cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

Exemplification

Scheme 1: Synthesis of Example 1

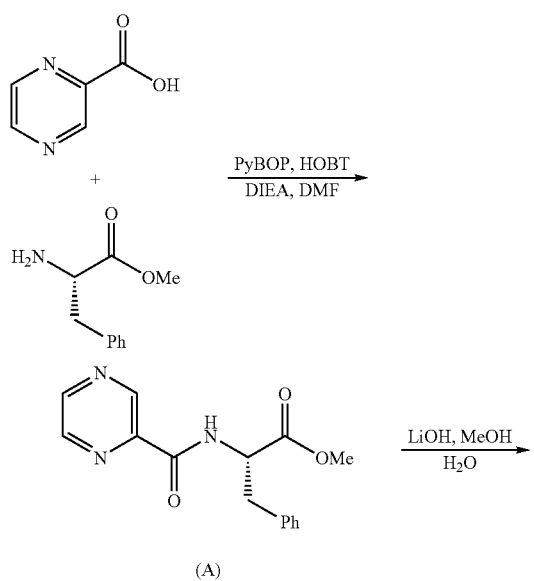

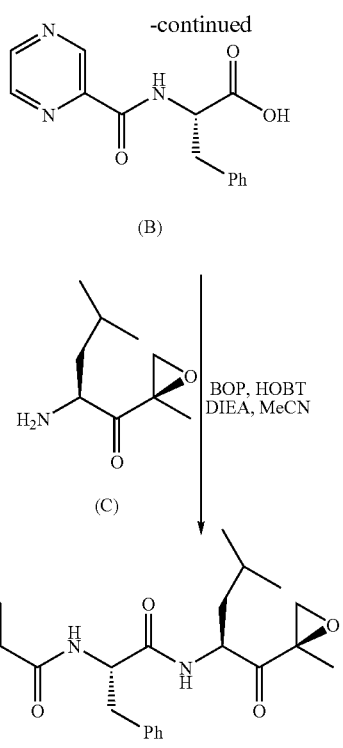

Synthesis of (A)

To a solution of phenylalanine methyl ester hydrochloride (2.31 mmol, 0.5 g) in 25 mL of DMF was added pyrazinecarboxylic acid (2.31 mmol, 0.28 g), DIEA (9.24 mmol, 1.19 g, 1.61 mL), and HOBT (3.70 mmol, 0.50 g) and the solution cooled to 0° C. To the cooled solution was added PyBOP (3.70 mmol, 1.93 g) in several portions and the mixture removed from the icebath and allowed to warm to room temperature while stirring under an atmosphere of argon for 6 hours. The mixture was diluted with brine (50 mL) and extracted with EtOAc (5×15 mL). The organic layers were combined, washed with $H_2O$ (2×15 mL) and brine (2×15 mL), and dried over $MgSO_4$. The $MgSO_4$ was removed by filtration and the volatiles removed under reduced pressure. The crude material was purified by flash chromatography to give (A) (0.64 g).

Synthesis of (B)

To a slurry of (A) (1.03 mmol, 0.298 g) in 15 mL of MeOH cooled to 0° C. was added LiOH (10.31 mmol, 0.247 g) dissolved in 5 mL $H_2O$. After 4 hours at 0° C., the reaction was quenched with 20 mL sat. $NH_4Cl$ and the pH of the reaction mixture adjusted to 2 with 1N HCl. The volatiles were removed under reduced pressure and the solids collected by filtration to give (B) (0.200 g).

Synthesis of Compound 1

To a stirred solution of (C) [see: Bioorg. Med. Chem. Letter 1999, 9, 2283-88] (0.08 mmol) in MeCN (2 mL) was added (B) (0.08 mmol, 0.021 g), DIEA (0.320 mmol, 0.055 mL), and HOBT (0.128 mmol, 0.017 g). The mixture was cooled to 0° C. in an ice bath and BOP (0.128 mmol, 0.057 g) was added in several portions. The mixture was stirred at 5° C. under an atmosphere of argon overnight. The reaction was then diluted with $H_2O$ (15 mL) and extracted with EtOAc (3×5 mL). The organic layers were combined, washed with water (2×5 mL), sat. $NaHCO_3$ (2×5 mL), and brine (2×5 mL), and dried over anhydrous $MgSO_4$. The $MgSO_4$ was removed by filtration and the volatiles removed under reduced pressure. The crude material was purified by flash chromatography to afford 1 (0.017 g).

Scheme 2: Synthesis of Example 2
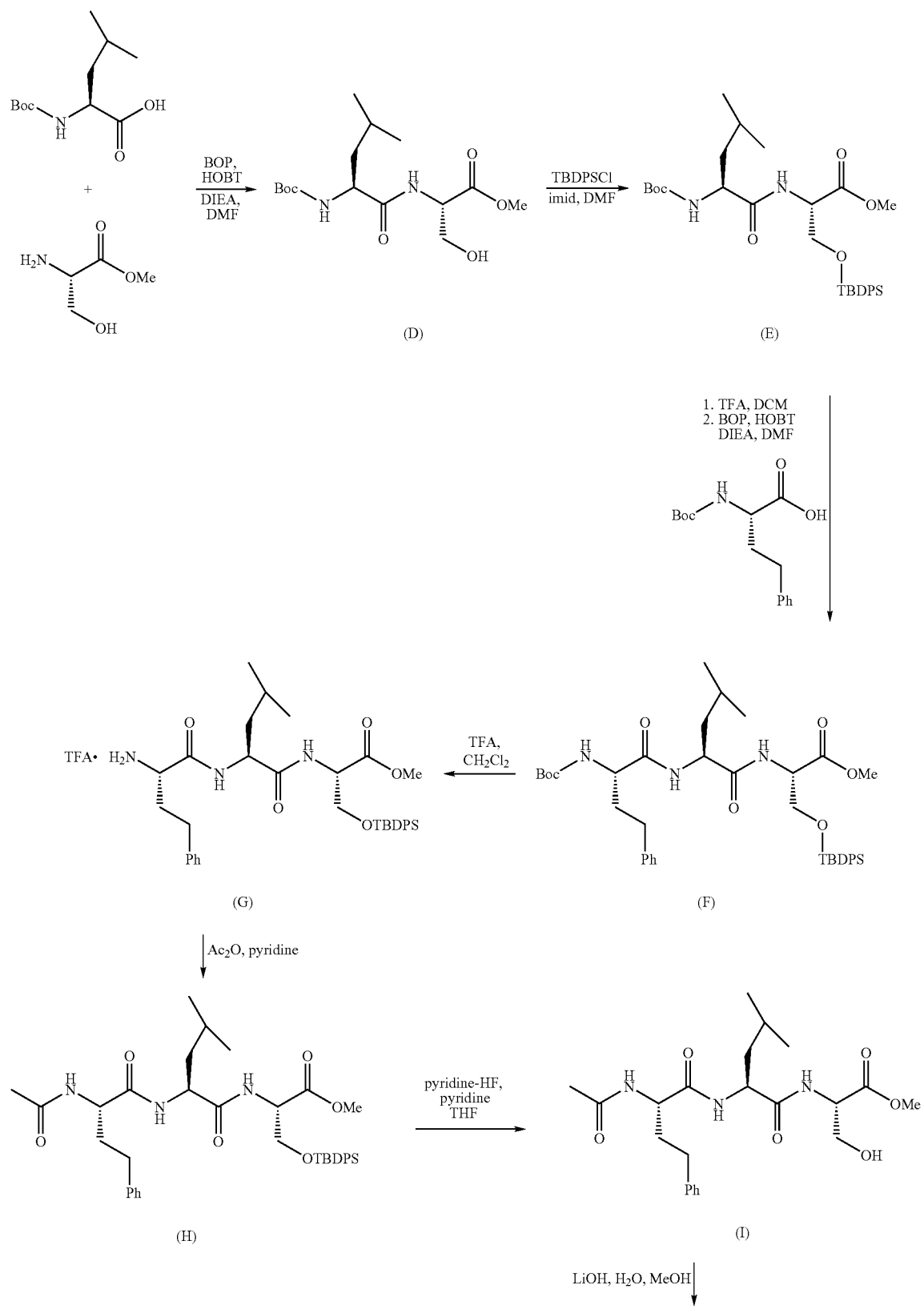

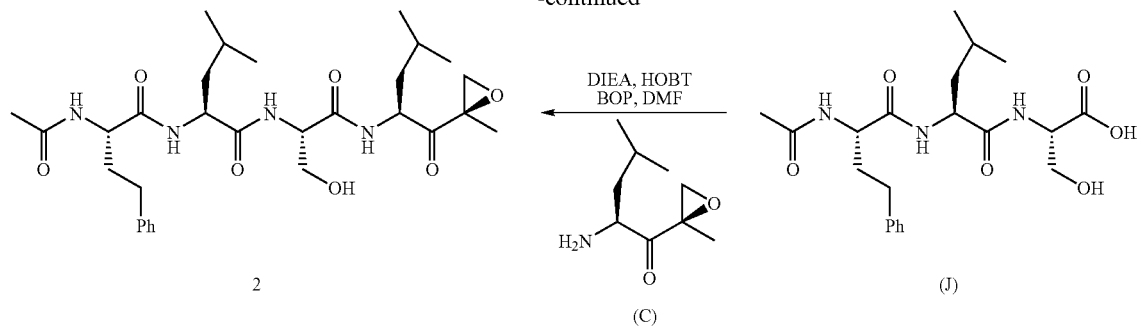

Synthesis of (D)

To a solution of NBOC leucine (40.0 mmol, 9.25 g) and serine methyl ester (40.0 mmol, 6.22 g) in 400 mL of DMF was added HOBT (64.0 mmol, 8.65 g) and DIEA (160.0 mmol, 20.68 g, 28 mL). The mixture was cooled to 0° C. in an ice-water bath and BOP (64.0 mmol, 28.30 g) was added in several portions over five minutes. The reaction was placed under an atmosphere of argon and stirred overnight. The reaction was diluted with brine (1000 mL) and extracted with EtOAc (6×200 mL). The organic layers were combined and washed with water (10×100 mL) and brine (3×200 mL), and dried over $MgSO_4$. The $MgSO_4$ was removed by filtration and the volatiles removed under reduced pressure to give (D) (13.65 g).

Synthesis of (E)

To a solution of imidizole (99.3 mmol, 6.76 g) in DMF (330 mL) was added TBDPSCl (49.64 mmol, 13.65 g) and the mixture stirred for 15 minutes under an argon atmosphere. Compound (D) (33.10 mmol, 11.0 g) was added and the mixture stirred overnight. The mixture was diluted with brine (750 mL) and extracted with EtOAc (6×200 mL). The organic layers were combined, washed with $H_2O$ (3×300 mL) and brine (2×200 mL), and dried over $MgSO_4$. The $MgSO_4$ was removed by filtration and the volatiles removed under reduced pressure. The crude material was purified by flash chromatography affording (E) (13.78 g).

Synthesis of (F)

To a 50 mL, 0° C. cooled solution of 80% TFA/DCM was added (E) (12.26 mmol, 7.0 g). The solution was stirred and allowed to warm to room temperature over 2 hr. The volatiles were removed under reduced pressure. To the oil was added BocNHhPhe (12.26 mmol, 3.42 g), 125 mL of DMF, HOBT (19.62 mmol, 2.65 g) and DIEA (49.04 mmol, 6.34 g, 8.5 mL). The mixture was cooled to 0° C. in an ice bath and BOP (19.62 mmol, 8.67 g) was added in several portions over five minutes. The reaction was placed under argon and allowed to warm to room temperature overnight. The reaction was diluted with 100 mL of DCM and poured into 600 mL $H_2O$. The organic layers were separated and washed with $H_2O$ (1×100 mL), sat. $NaHCO_3$ (1×100 mL), and brine (1×100 mL) and dried over $MgSO_4$. The $MgSO_4$ was removed by filtration and the volatiles removed under reduced pressure to give (F) (8.14 g).

Synthesis of (G)

To a solution of (F) (1.6 mmol, 1.0 g) in DCM (10 mL) at 0° C., in an ice bath, was slowly added a solution of 20% TFA/DCM (20 mL). The solution was allowed to slowly warm to room temperature and stir overnight. The volatiles were removed under vacuum and the residue diluted with DCM and evaporated (3×). The resulting oil was placed under high vacuum for 2 hrs to yield (G).

Synthesis of (H)

To a solution of Intermediate (G) (1.6 mmol) in pyridine (10 mL) at 0° C., in an ice bath, was slowly added acetic anhydride (10 mL). The resulting solution was allowed to warm to room temperature and stir overnight. The volatiles were removed under vacuum and the residue was diluted with DCM and evaporated. The resulting solid was dissolved in hot EtOH (20 mL) and slowly poured in to ice (200 mL). The solids were collected by filtration and allowed to air dry, yielding (H) (0.735 g, 1.3 mmol).

Synthesis of (I)

To a solution of pyridinium hydrofluoride (109 mmol, 2.2 g) in THF (10 mL) and pyridine (5.7 mL), was slowly added (H) (0.36 mmol, 0.20 g,). The resulting solution was allowed to stir for 2.5 hrs then quenched by the slow addition of sat. $NaHCO_3$ (10 mL). The mixture was extracted with EtOAc (3×10 mL) and the organic layers combined, washed with $H_2O$ (3×10 mL) and brine (10 mL), and dried over $MgSO_4$. The $MgSO_4$ was removed by filtration and the volatiles removed under reduced pressure to give (I) (0.22 mmol, 0.095 g).

Synthesis of (J)

To a heterogenous solution of (I) (0.12 mmol, 0.050 g) in MeOH (1.5 mL) and $H_2O$ (0.5 mL) at 0° C. was added a solution of LiOH (1.0 mmol, 0.024 g) in $H_2O$ (0.25 mL) dropwise. The resulting solution was allowed to slowly warm to room temperature and stir overnight. The reaction mixture was diluted with sat. $NH_4Cl$ (10 mL) and poured into ice (10 mL) and the pH of the solution adjusted to 2 with 1N HCl. The resulting solution was extracted with EtOAc (3×15 mL) and the organic layers combined, washed with $H_2O$ (1×10 mL) and brine (1×10 mL), and dried over $MgSO_4$. The $MgSO_4$ was removed by filtration and the volatiles removed under reduced pressure to give a semi-solid. The semi-solid was placed under high vacuum for 2 hrs to yield (J) (0.023 g, 0.05 mmol).

Synthesis of Compound 2

To a stirred solution of (C) [see: Bioorg. Med. Chem. Letter 1999, 9, 2283-88] (15 mg, 0.19 mmol) in DMF (2 mL) was added (J) (0.05 mmol, 0.02 g), DIEA (0.02 mmol, 0.033 mL), and HOBT (0.02 mmol, 0.010 g). The mixture was cooled to 0° C. in an ice bath and BOP (0.07 mmol, 0.035 g) was added in several portions. The mixture was stirred at 5° C. under an atmosphere of argon overnight. The reaction was diluted with brine (15 mL) and extracted with EtOAc. The organic layer was washed with water, sat. $NaHCO_3$, and brine and dried over anhydrous $MgSO_4$. The $MgSO_4$ was removed by filtration and the volatiles removed under reduced pressure. The crude material was purified by flash chromatography using 20 to 40% EtOAc/hexanes as the eluent, to afford 2 (3.6 mg). $IC_{50}$ 20S CT-L<50 nM, $IC_{50}$ Cell-based CT-L<500 nM.

Scheme 3: Synthesis of Example 3

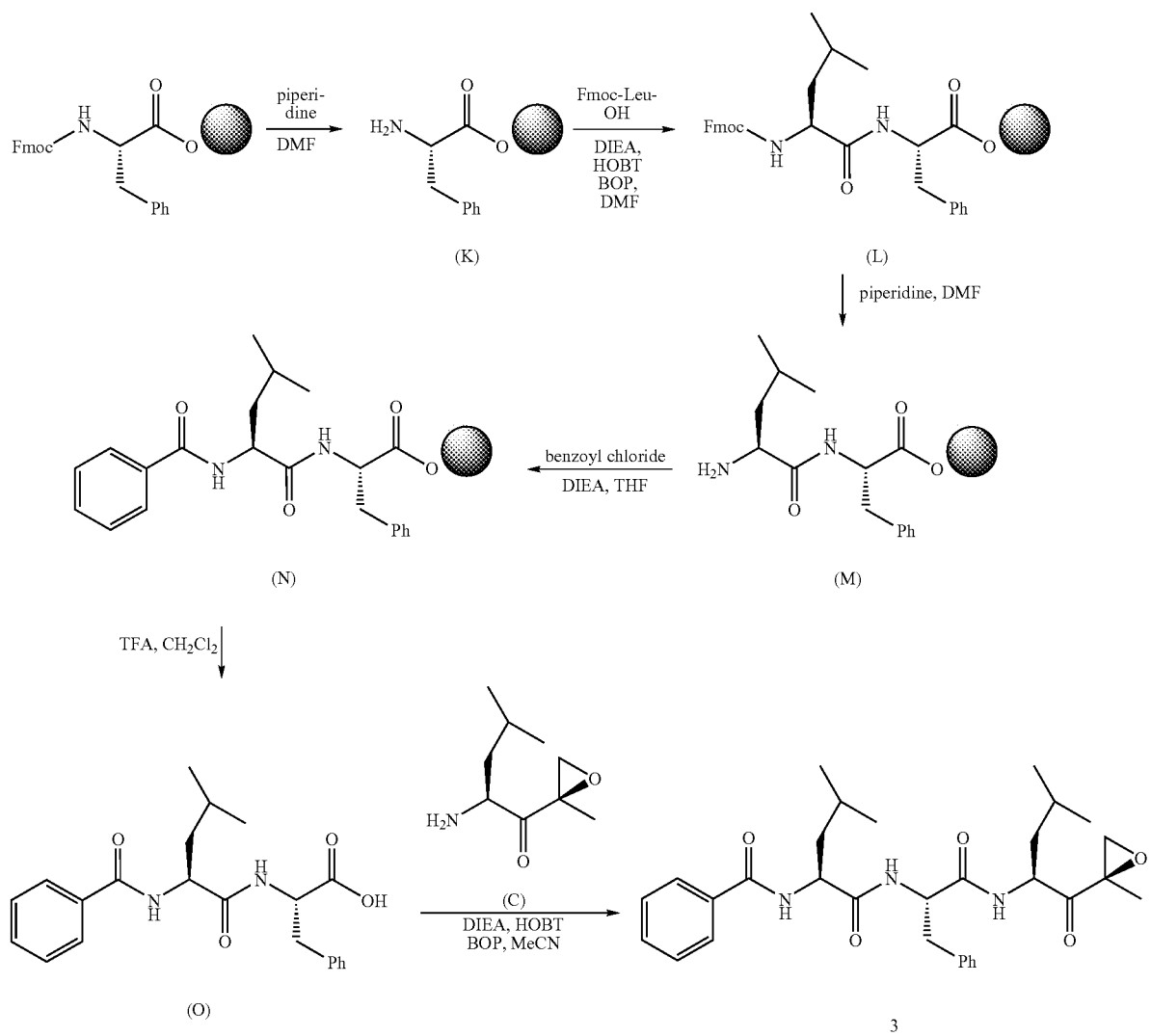

Synthesis of (K)

To Fmoc-Phe-Wang resin (4.0 mmol, 5.0 g) was added a mixture of 20% piperidine/DMF (50 mL). The heterogenous mixture was allowed to shake for 20 minutes and was filtered and the resin washed with DMF (100 mL), MeOH (100 mL), and DCM (100 mL) and allowed to air dry. The resin was subjected to the above reaction condition a second time, to yield (K).

Synthesis of (L)

To a mixture of (K) (4.0 mmol) and DMF (40 mL) was added, in order, Fmoc-Leu-OH (7.9 mmol, 2.82 g), DIEA (13.3 mmol, 2.23 mL), and HOBT (8.10 mmol, 1.24 g). To the above mixture was slowly added BOP (7.98 mmol, 3.53 g) and diluted in DMF (40 mL). The reaction mixture was allowed to shake overnight. The reaction mixture was filtered and the resin washed with DMF (150 mL), MeOH (150 mL), DCM (150 mL), and allowed to air dry, to yield (L).

Synthesis of (M)

To (L) (4.0 mmol) was added a mixture of 20% piperidine/DMF (50 mL). The heterogenous mixture was allowed to shake for 20 minutes. The solution was filtered and the resin washed with DMF (100 mL), MeOH (100 mL), and DCM (100 mL) and allowed to air dry. The resin was then subjected to the above reaction condition a second time to yield (M).

Synthesis of (N)

To (M) (0.10 mmol, 0.130 g) was added THF (2 mL), DIEA (0.40 mmol, 0.08 mL), and benzoyl chloride (0.34 mmol, 0.04 mL). The resulting mixture was allowed to shake for 30 minutes. The reaction was filtered and the resin washed with DMF (20 mL), water (20 mL), MeOH (20 mL), and DCM (20 mL) and allowed to air dry, to yield (N).

Synthesis of (O)

To (N) (0.10 mmol) was added 50% TFA/DCM (2 mL) and the mixture was allowed to shake for 20 minutes (the resin turned purple). The mixture was filtered and the resin washed with DCM (10 mL). The volatiles were removed under reduced pressure and the resulting oil was diluted with DCM (10 mL) and evaporated a total of three times to yield (O).

Synthesis of Compound 3

To a stirred solution of (C) [see: Bioorg. Med. Chem. Letter 1999, 9, 2283-88] (19 mg, 0.11 mmol) in MeCN (2 mL) was added (O) (0.1 mmol), DIEA (2.9 mmol, 0.5 mL), HOBT (0.2 mmol, 0.032 g), and BOP (0.23 mmol, 0.103 g). The mixture was stirred at room temperature overnight. The reaction was then diluted with brine (15 mL) and extracted with EtOAc. The organic layer was washed with water, sat. NaHCO$_3$, and brine and dried over anhydrous MgSO$_4$. The MgSO$_4$ was removed by filtration and the volatiles removed under reduced pressure. The crude material was purified by flash chromatography using 20 to 40% EtOAc/hexanes as the eluent, to afford 3 (13.8 mg). IC$_{50}$ 20S CT-L<50 nM, IC$_{50}$ Cell-based CT-L<50 nM.

Scheme 4: Synthesis of Example 4

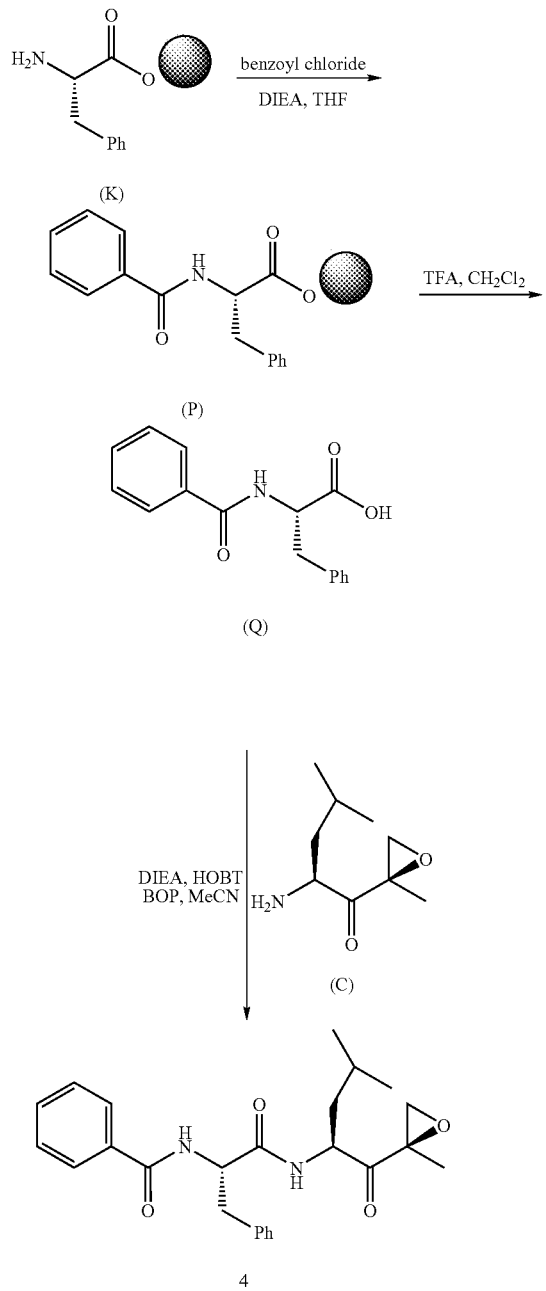

Synthesis of (P)

To Intermediate (K) (0.10 mmol, 0.130 g) was added THF (2 mL), DIEA (0.40 mmol, 0.08 mL), and benzoyl chloride (0.34 mmol, 0.04 mL). The resulting mixture was allowed to shake for 30 minutes. The reaction was filtered and the resin washed with DMF (20 mL), water (20mL), MeOH (20 mL), and DCM (20 mL) and allowed to air dry, to yield (P).

Synthesis of (Q)

To (P) was added 50% TFA/DCM (2 mL) and allowed to shake for 20 minutes (the resin turned purple). The reaction was filtered and the resin washed with DCM (10 mL). The volatiles were removed under reduced pressure and the resulting oil was diluted with DCM (10 mL) and evaporated a total of three times to yield (Q).

Synthesis of Compound 4

To a stirred solution of (C) [see: Bioorg. Med. Chem. Letter 1999, 9, 2283-88] (19 mg, 0.11 mmol) in MeCN (2 mL) was added (Q) (0.1 mmol), DIEA (2.9 mmol, 0.5 mL), HOBT (0.2 mmol, 0.032 g), and BOP (0.23 mmol, 0.103 g). The mixture was then stirred at room temperature overnight. The reaction was diluted with brine (15 mL) and extracted with EtOAc. The organic layer was washed with water, sat. NaHCO$_3$, and brine and dried over anhydrous MgSO$_4$. The MgSO$_4$ was removed by filtration and the volatiles removed under reduced pressure. The crude material was purified by flash chromatography using 20 to 40% EtOAc/hexanes as the eluent, to afford 4 (12.7 mg).

Scheme 5: Synthesis of Example 5

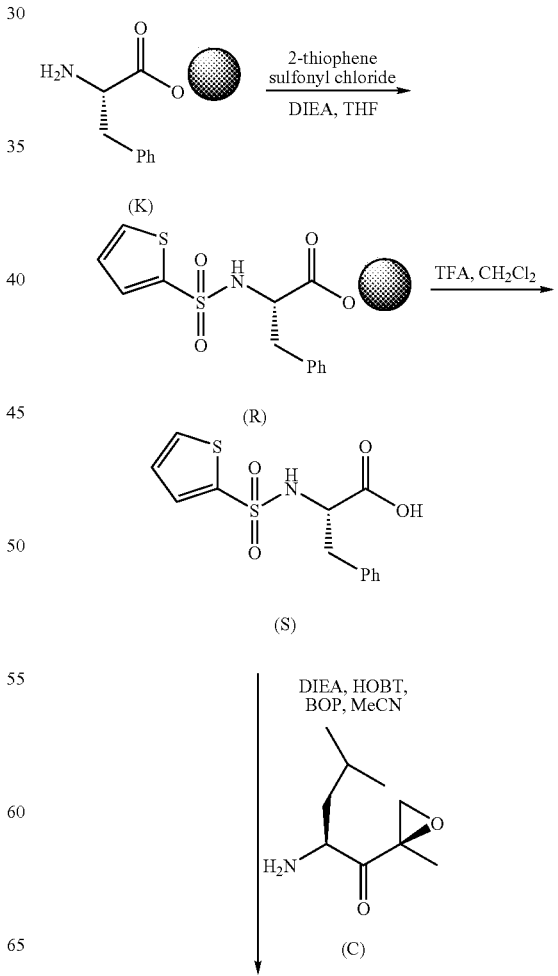

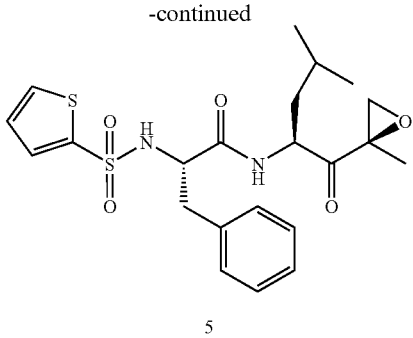

5

Synthesis of (R)

To (K) (0.10 mmol, 0.130 g) was added THF (2 mL), DIEA (0.40 mmol, 0.08 mL) and 2-thiophenesulfonyl chloride (0.34 mmol, 0.064 g). The resulting mixture was allowed to shake for 30 minutes. The reaction was then filtered and the resin washed with DMF (20 mL), water (20 mL), MeOH (20 mL), and DCM (20 mL) and allowed to air dry, to yield (R).

Synthesis of (S)

To (R) (0.10 mmol) was added 50% TFA/DCM (2 mL) and allowed to shake for 20 minutes (the resin turned purple). The reaction was then filtered and the resin washed with DCM (10 mL). The volatiles were removed under reduced pressure and the resulting oil was diluted with DCM (10 mL) and evaporated a total of three times to yield (S).

Synthesis of Compound 5

To a stirred solution of (C) [see: Bioorg. Med. Chem. Letter 1999, 9, 2283-88] (0.11 mmol, 0.019 g,) in MeCN (2 mL) was added (S) (0.1 mmol), DIEA (2.9 mmol, 0.5 mL), HOBT (0.2 mmol, 0.032 g), and BOP (0.23 mmol, 0.103 g) and the mixture was stirred at room temperature overnight. The reaction was then diluted with brine (15 mL) and extracted with EtOAc. The organic layer was washed with water, sat. NaHCO$_3$, and brine and dried over anhydrous MgSO$_4$. The MgSO$_4$ was removed by filtration and the volatiles removed under reduced pressure. The crude material was purified by flash chromatography using 20 to 40% EtOAc/hexanes as the eluent, to afford 5 (13.1 mg).

Scheme 6: Synthesis of Example 6

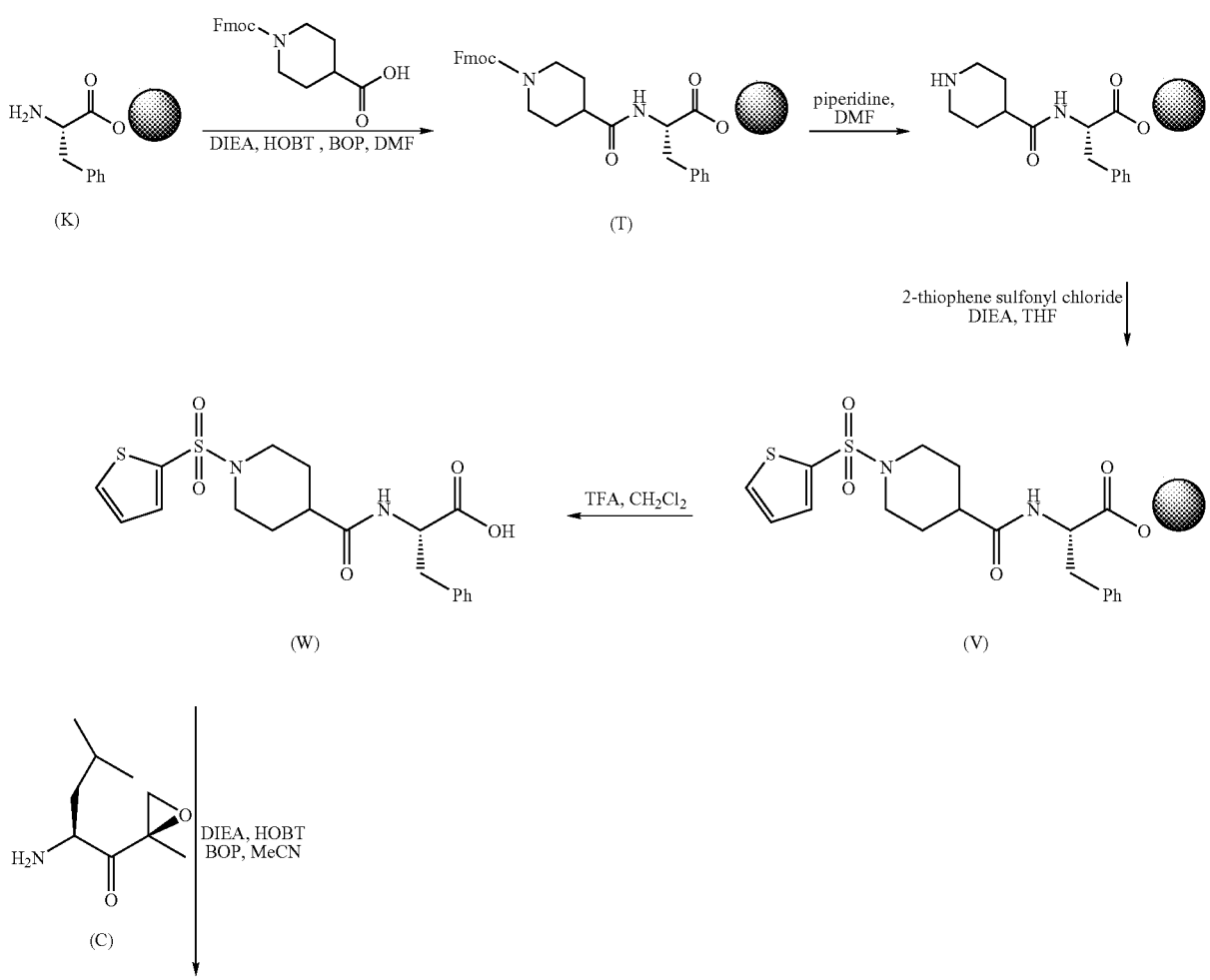

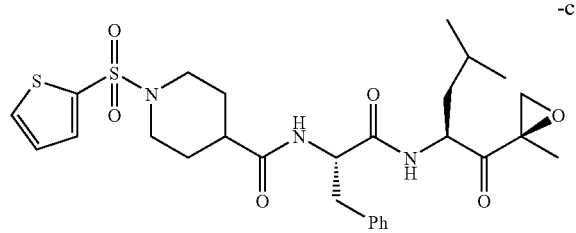

6

Synthesis of (T)

To (K) (0.8 mmol, 1.0 g) was added DMF (20 mL), Fmoc-isonipecotic acid (2.8 mmol, 0.320 g,), DIEA (4.8 mmol, 0.445 mL,), HOBT (0.9 mmol, 0.140 g), and BOP (1.0 mmol, 0.450 g) and the reaction mixture was allowed to shake overnight. The reaction mixture was filtered and the resin washed with DMF (150 mL), MeOH (150 mL), and DCM (150 mL), and allowed to air dry, to yield (T).

Synthesis of (U)

To (T) (0.8 mmol, 1.0 g) was added a mixture of 20% piperidine/DMF (30 mL) and the heterogenous mixture was allowed to shake for 20 minutes. The mixture was filtered and the resin washed with DMF (150 mL), MeOH (150 mL), and DCM (150 mL) and allowed to air dry. The resin was subjected to the above reaction condition a second time to yield (U).

Synthesis of (Y)

To (U) (0.10 mmol, 0.130 g) was added THF (2 mL), DIEA (0.40 mmol, 0.08 mL), and 2-thiophenesulfonyl chloride (0.34 mmol, 0.064 g) and the resulting mixture was allowed to shake for 30 minutes. The reaction was filtered and the resin washed with DMF (20 mL), water (20 mL), MeOH (20 mL), and DCM (20 mL) and allowed to air dry, to yield (V).

Synthesis of (W)

To (V) (0.10 mmol) was added 50% TFA/DCM (2 mL) and the mixture was allowed to shake for 20 minutes (the resin turned purple). The reaction was then filtered and the resin washed with DCM (10 mL). The volatiles were removed under reduced pressure and the resulting oil was diluted with DCM (10 mL) and evaporated a total of three times to yield (W).

Synthesis of Compound 6

To a stirred solution of (C) [see: Bioorg. Med. Chem. Letter 1999, 9, 2283-88] (19 mg, 0.11 mmol) in MeCN (2 mL) was added (W) (0.1 mmol), DIEA (2.9 mmol, 0.5 mL), HOBT (0.2 mmol, 0.032 g), and BOP (0.23 mmol, 0.103 g) and the mixture was stirred at room temperature overnight. The reaction was diluted with brine (15 mL) and extracted with EtOAc. The organic layer was washed with water, sat. NaHCO₃, and brine and dried over anhydrous MgSO₄. The MgSO₄ was removed by filtration and the volatiles removed under reduced pressure. The crude material was purified by flash chromatography using 20 to 40% EtOAc/hexanes as the eluent, to afford 6 (7.4 mg).

Scheme 7: Synthesis of Example 7

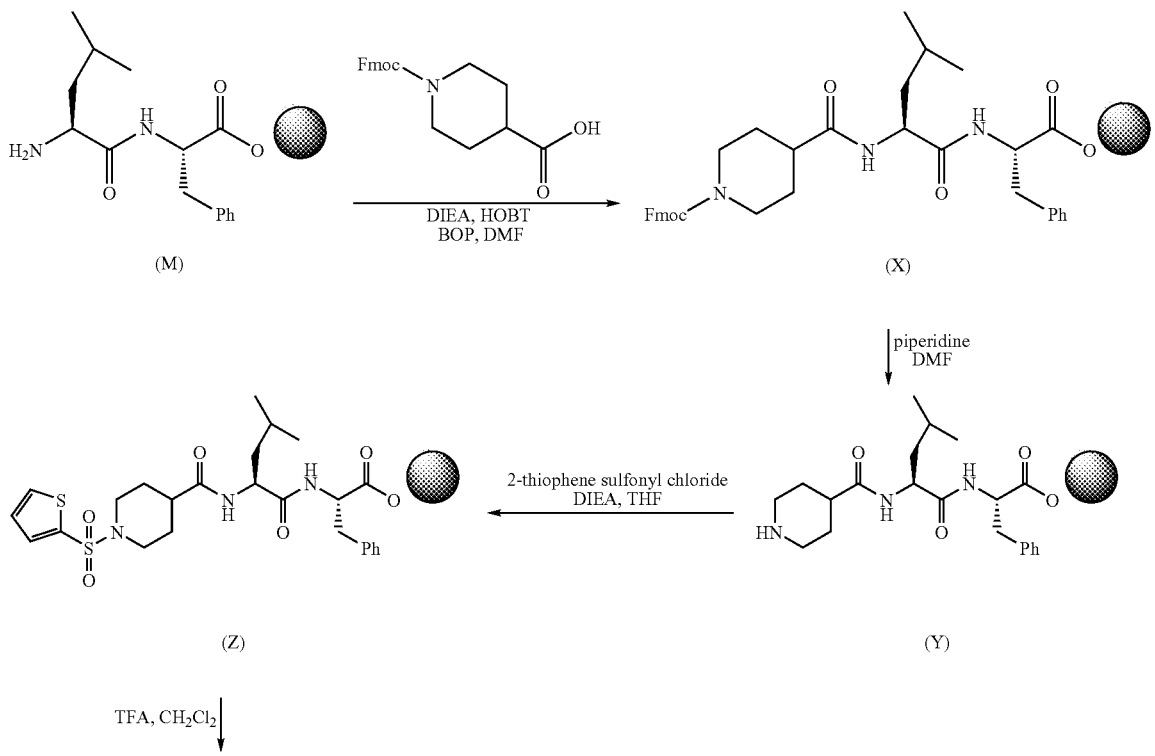

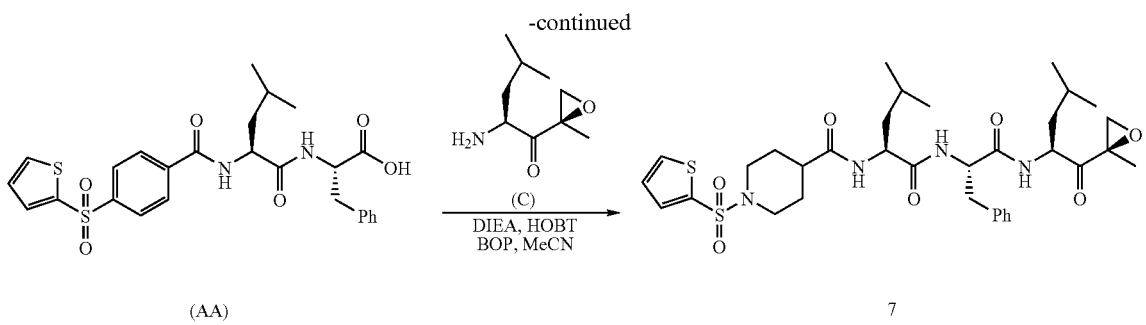

Synthesis of (X)

To (M) (0.8 mmol, 1.0 g,) was added DMF (20 mL), Fmoc-isonipecotic acid (2.8 mmol, 0.320 g), DIEA (4.8 mmol, 0.445 mL), HOBT (0.9 mmol, 0.140 g), and BOP (1.0 mmol, 0.450 g) and the reaction mixture was allowed to shake overnight. The reaction mixture was filtered and the resin washed with DMF (150 mL), MeOH (150 mL), and DCM (150 mL), and allowed to air dry, to yield (X).

Synthesis of (Y)

To (X) (0.8 mmol, 1.0 g) was added 20% piperidine/DMF (30 mL) and the resulting heterogenous mixture was allowed to shake for 20 minutes. The solution was filtered and the resin washed with DMF (150 mL), MeOH (150 mL), and DCM (150 mL) and allowed to air dry. The resin was subjected to the above reaction condition a second time to yield (Y).

Synthesis of (Z)

To (Y) (0.10 mmol, 0.130 g) was added THF (2 mL), DIEA (0.40 mmol, 0.08 mL), and 2-thiophenesulfonyl chloride (0.34 mmol, 0.064 g) and the resulting mixture was allowed to shake for 30 minutes. The reaction was filtered and the resin washed with DMF (20 mL), water (20 mL), MeOH (20 mL), and DCM (20 mL) and allowed to air dry, to yield (Z).

Synthesis of (AA)

To (Z) (0.10 mmol) was added 50% TFA/DCM (2 mL), and the mixture was allowed to shake for 20 minutes (the resin turned purple). The reaction was filtered and the resin washed with DCM (10 mL). The volatiles were removed under reduced pressure and the resulting oil was diluted with DCM (10 mL) and evaporated a total of three times to yield (AA).

Synthesis of Compound 7

To a stirred solution of (C) [see: Bioorg. Med. Chem. Letter 1999, 9, 2283-88] (0.11 mmol, 0.019 g) in MeCN (2 mL) was added (AA) (0.1 mmol), DIEA (2.9 mmol, 0.5 mL), HOBT (0.2 mmol, 0.032 g), and BOP (0.23 mmol, 0.103 g) and the mixture was stirred at room temperature overnight. The reaction was diluted with brine (15 mL) and extracted with EtOAc. The organic layer was washed with water, sat. NaHCO$_3$, and brine and dried over anhydrous MgSO$_4$. The MgSO$_4$ was removed by filtration and the volatiles removed under reduced pressure. The crude material was purified by flash chromatography using 20 to 40% EtOAc/hexanes as the eluent, to afford 7 (18.2 mg). IC$_{50}$ 20S CT-L<500 nM, IC$_{50}$ Cell-based CT-L<500 nM.

Scheme 8: Synthesis of Example 8

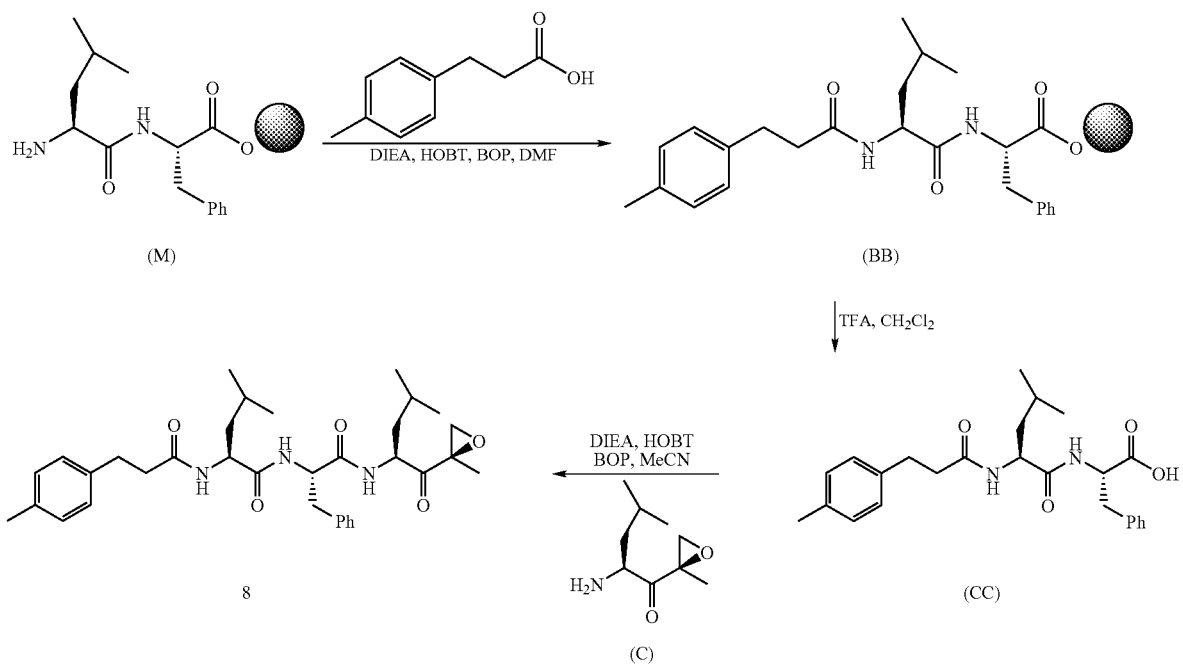

Synthesis of (BB)

To (M) (0.12 mmol, 0.100 g) was added DMF (2 mL), 3-(p-tolyl)propionic acid (0.09 mmol, 0.015 g), DIEA (0.17 mmol, 0.029 mL), HOBT (0.11 mmol, 0.016 g), and BOP (0.11 mmol, 0.051 g) and the reaction mixture was allowed to shake overnight. The reaction mixture was filtered and the resin washed with DMF (15 mL), MeOH (15 mL), and DCM (15 mL), and allowed to air dry, to yield (BB).

Synthesis of (CC)

To (BB) (0.12 mmol) was added 50% TFA/DCM (2 mL), and the mixture was allowed to shake for 20 minutes (the resin turned purple). The reaction was filtered and the resin washed with DCM (10 mL). The volatiles were removed under reduced pressure and the resulting oil was diluted with DCM (10 mL) and evaporated a total of three times to yield (CC).

Synthesis of Compound 8

To a stirred solution of (C) [see: Bioorg. Med. Chem. Letter 1999, 9, 2283-88] (0.11 mmol, 0.019 g) in MeCN (2 mL) was added (CC) (0.1 mmol), DIEA (2.9 mmol, 0.5 mL), HOBT (0.2 mmol, 0.032 g), and BOP (0.23 mmol, 0.103 g) and the mixture was stirred at room temperature overnight. The reaction was diluted with brine (15 mL) and extracted with EtOAc. The organic layer was washed with water, sat. NaHCO$_3$, brine and dried over anhydrous MgSO$_4$. The MgSO$_4$ was removed by filtration and the volatiles removed under reduced pressure. The crude material was purified by flash chromatography using 20 to 40% EtOAc/hexanes as the eluent, to afford 8 (3.9 mg). IC$_{50}$ 20S CT-L<50 nM, IC$_{50}$ Cell-based CT-L<50 nM.

Scheme 9: Synthesis of Example 9

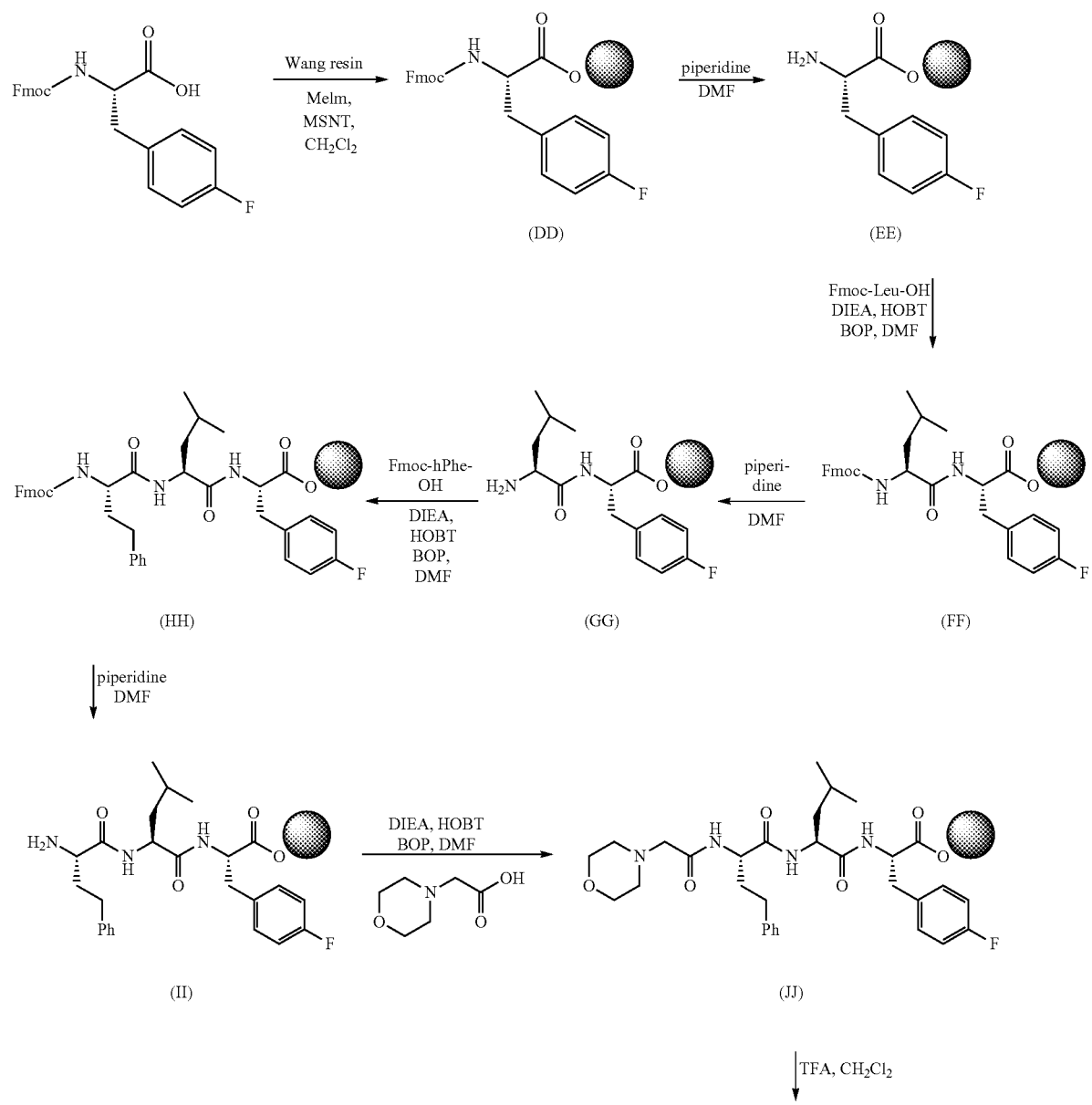

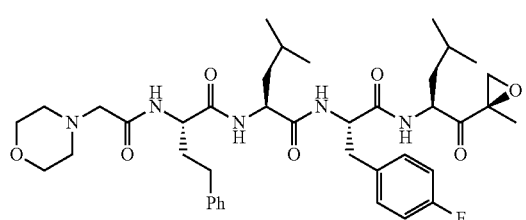
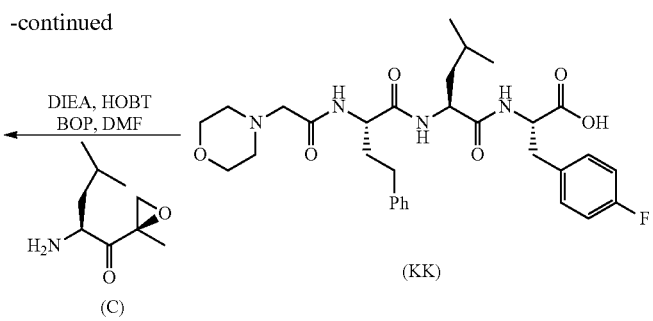

Synthesis of (DD)

To a solution of Fmoc-Phe (4-F)—OH (2.4 mmol, 1.0 g,) in DCM (20 mL) was added MeIm (6.7 mmol, 0.370 mL). When the solution was homogenous, MSNT (2.9 mmol, 0.870 g,) was added. Once the MSNT dissolved, the reaction mixture was added to Wang resin (0.8 mmol, 1.0 g) and the resulting solution was allowed to shake for 45 minutes. The resin was filtered and washed with DMF (50 mL), MeOH (50 mL), and DCM (50 mL). The resulting resin was allowed to air dry, to yield (DD).

Synthesis of (EE)

To (DD) (0.40 mmol, 0.5 g) was added 20% piperidine/DMF (10 mL) and the resulting heterogenous solution was allowed to shake for 20 minutes. The mixture was filtered and the resin washed with DMF (20 mL), MeOH (20 mL), and DCM (20 mL) and allowed to air dry. The resin was subjected to the above reaction condition a second time to yield (EE).

Synthesis of (FF)

To (EE) (0.40 mmol) was added DMF (20 mL), Fmoc-Leu-OH (0.40 mmol, 0.143 g), DIEA (1.6 mmol, 0.12 mL), HOBT (0.64 mmol, 0.062 mg), and BOP (0.64 mmol, 0.178 g) and the reaction mixture was allowed to shake overnight. The reaction mixture was filtered and the resin washed with DMF (40 mL), MeOH (40 mL), and DCM (40 mL), and allowed to air dry, to yield (FF).

Synthesis of (GG)

To (FF) (0.08 mmol, 0.10 g) was added 20% piperidine/DMF (2 mL) and the resulting heterogenous solution was allowed to shake for 20 minutes. The solution was filtered and the resin washed with DMF (10 mL), MeOH (10 mL), and DCM (10 mL) and allowed to air dry. The resin was subjected to the above reaction condition a second time to yield (GG).

Synthesis of (HH)

To (GG) (0.08 mmol) was added DMF (20 mL), Fmoc-hPhe-OH (0.40 mmol, 0.143 g), DIEA (1.6 mmol, 0.12 mL), HOBT (0.64 mmol, 0.062 mg), and BOP (0.64 mmol, 0.178 g) and the reaction mixture was allowed to shake overnight. The reaction mixture was filtered and the resin washed with DMF (40 mL), MeOH (40 mL), and DCM (40 mL), and allowed to air dry, to yield (HH).

Synthesis of (II)

To (HH) (0.08 mmol) was added 20% piperidine/DMF (2 mL) and the resulting heterogenous solution was allowed to shake for 20 minutes. The solution was filtered and the resin washed with DMF (10 mL), MeOH (10 mL), and DCM (10 mL) and allowed to air dry. The resin was subjected to the above reaction condition a second time, to yield (II).

Synthesis of (JJ)

To (II) (0.08 mmol) was added DMF (2 mL), 4-morpholinoacetic acid (0.10 mmol, 0.015 g), DIEA (0.17 mmol, 0.029 mL), HOBT (0.11 mmol, 0.016 g), and BOP (0.11 mmol, 0.051 g) and the reaction mixture was allowed to shake overnight. The reaction mixture was filtered and the resin washed with DMF (15 mL), MeOH (15 mL), and DCM (15 mL), and allowed to air dry, to yield (JJ).

Synthesis of (KK)

To (JJ) (0.08 mmol) was added 50% TFA/DCM (2 mL) and the mixture was allowed to shake for 20 minutes (the resin turned purple). The reaction was filtered and the resin washed with DCM (10 mL). The volatiles were removed under reduced pressure and the resulting oil was diluted with DCM (10 mL) and evaporated a total of three times to yield (KK).

Synthesis of Compound 9

To a stirred solution of (C) [see: Bioorg. Med. Chem. Letter 1999, 9, 2283-88] (0.11 mmol, 0.019 g) in MeCN (2 mL) was added (KK) (0.1 mmol), DIEA (2.9 mmol, 0.5 mL), HOBT (0.2 mmol, 0.032g), and BOP (0.23 mmol, 0.103 g) and the mixture was stirred at room temperature overnight. The reaction was diluted with brine (15 mL) and extracted with EtOAc. The organic layer was washed with water, sat. NaHCO$_3$, and brine and dried over anhydrous MgSO$_4$. The MgSO$_4$ was removed by filtration and the volatiles removed under reduced pressure. The crude material was purified by flash chromatography using 20 to 40% EtOAc/hexanes as the eluent, to afford 9 (7.7 mg). IC$_{50}$ 20S CT-L<50 nM, IC$_{50}$ Cell-based CT-L<50 nM.

Scheme 10: Synthesis of Example 10

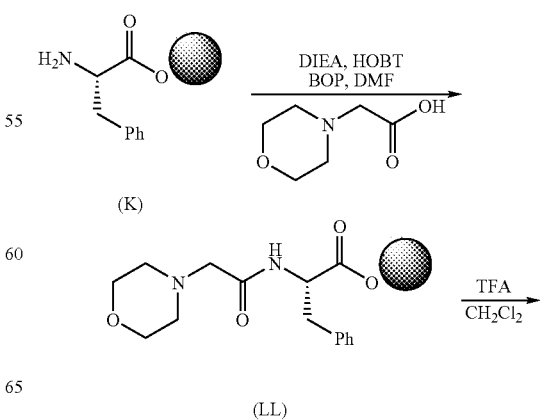

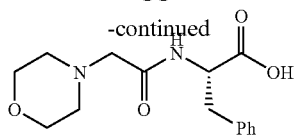

(MM)

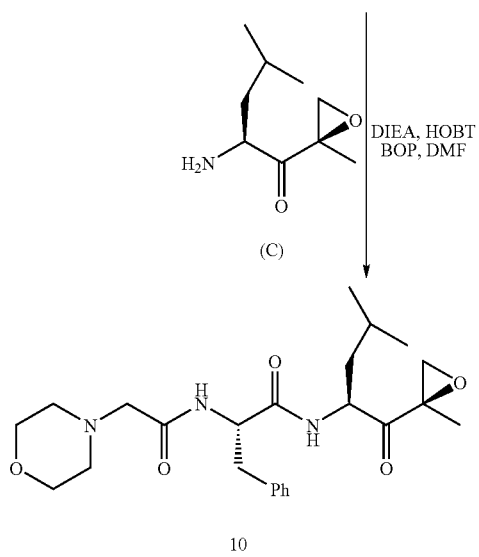

Synthesis of (LL)

To (K) (0.12 mmol, 0.100 g) was added DMF (2 mL), 4-morpholinoacetic acid (0.12 mmol, 0.018 g), DIEA (0.17 mmol, 0.029 mL), HOBT (0.11 mmol, 0.016 g), and BOP (0.11 mmol, 0.051 g) and the reaction mixture was allowed to shake overnight. The reaction mixture was filtered and the resin washed with DMF (15 mL), MeOH (15 mL), and DCM (15 mL), and allowed to air dry, to yield (LL).

Synthesis of (MM)

To (LL) (0.12 mmol) was added was 50% TFA/DCM (2 mL) and the mixture was allowed to shake for 20 minutes (the resin turned purple). The reaction was filtered and the resin washed with DCM (10 mL). The volatiles were removed under reduced pressure and the resulting oil was diluted with DCM (10 mL) and evaporated a total of three times to yield (MM).

Synthesis of Compound 10

To a stirred solution of (C) [see: Bioorg. Med. Chem. Letter 1999, 9, 2283-88] (0.11 mmol, 0.019 g) in MeCN (2 mL) was added (MM) (0.1 mmol), DIEA (2.9 mmol, 0.5 mL), HOBT (0.2 mmol, 0.032 g), and BOP (0.23 mmol, 0.103 g) and the mixture was stirred at room temperature overnight. The reaction was diluted with brine (15 mL) and extracted with EtOAc. The organic layer was washed with water, sat. NaHCO$_3$, and brine and dried over anhydrous MgSO$_4$. The MgSO$_4$ was removed by filtration and the volatiles removed under reduced pressure. The crude material was purified by flash chromatography using 20 to 40% EtOAc/hexanes as the eluent, to afford 10 (14 mg).

Scheme 11: Synthesis of Example 11

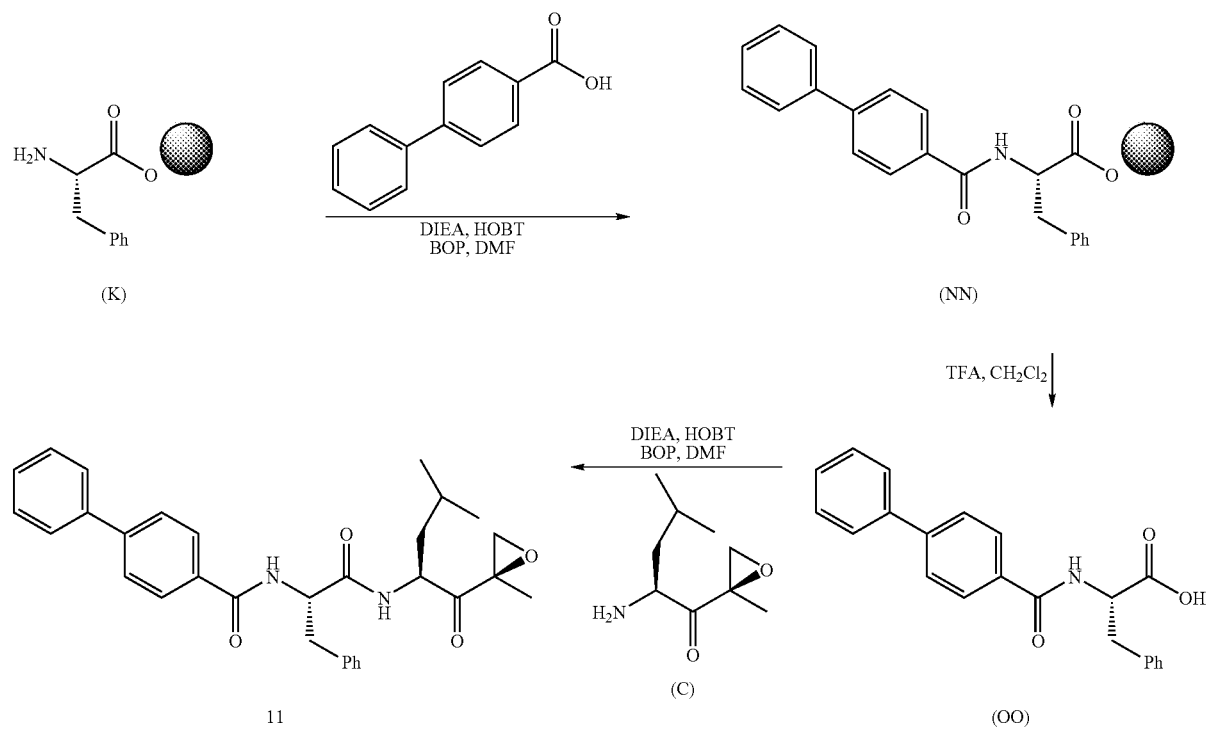

Synthesis of (NN)

To (K) (0.12 mmol, 0.100 g) was added DMF (2 mL), biphenyl-4-carboxylic acid (0.12 mmol, 0.025 g), DIEA (0.17 mmol, 0.029 mL), HOBT (0.11 mmol, 0.016 g), and BOP (0.11 mmol, 0.051 g) and the reaction mixture was allowed to shake overnight. The reaction mixture was filtered and the resin washed with DMF (15 mL), MeOH (15 mL), and DCM (15 mL), and allowed to air dry, to yield (NN).

Synthesis of (OO)

To (NN) (0.12 mmol) was added 50% TFA/DCM (2 mL) and allowed to shake for 20 minutes (the resin turned purple). The reaction was filtered and the resin washed with DCM (10 mL). The volatiles were removed under reduced pressure and the resulting oil was diluted with DCM (10 mL) and evaporated a total of three times to yield (OO).

Synthesis of Compound 11

To a stirred solution of (C) [see: Bioorg. Med. Chem. Letter 1999, 9, 2283-88] (0.11 mmol, 0.019 g) in MeCN (2 mL) was added (OO) (0.1 mmol), DIEA (2.9 mmol, 0.5 mL), HOBT (0.2 mmol, 0.032 g), and BOP (0.23 mmol, 0.103 g) and the mixture was stirred at room temperature overnight. The reaction was diluted with brine (15 mL) and extracted with EtOAc. The organic layer was washed with water, sat. $NaHCO_3$, brine and dried over anhydrous $MgSO_4$. The $MgSO_4$ was removed by filtration and the volatiles removed under reduced pressure. The crude material was purified by flash chromatography using 20 to 40% EtOAc/hexanes as the eluent, to afford 11 (7.4 mg).

Scheme 12: Synthesis of Examples 12, 13, and 14

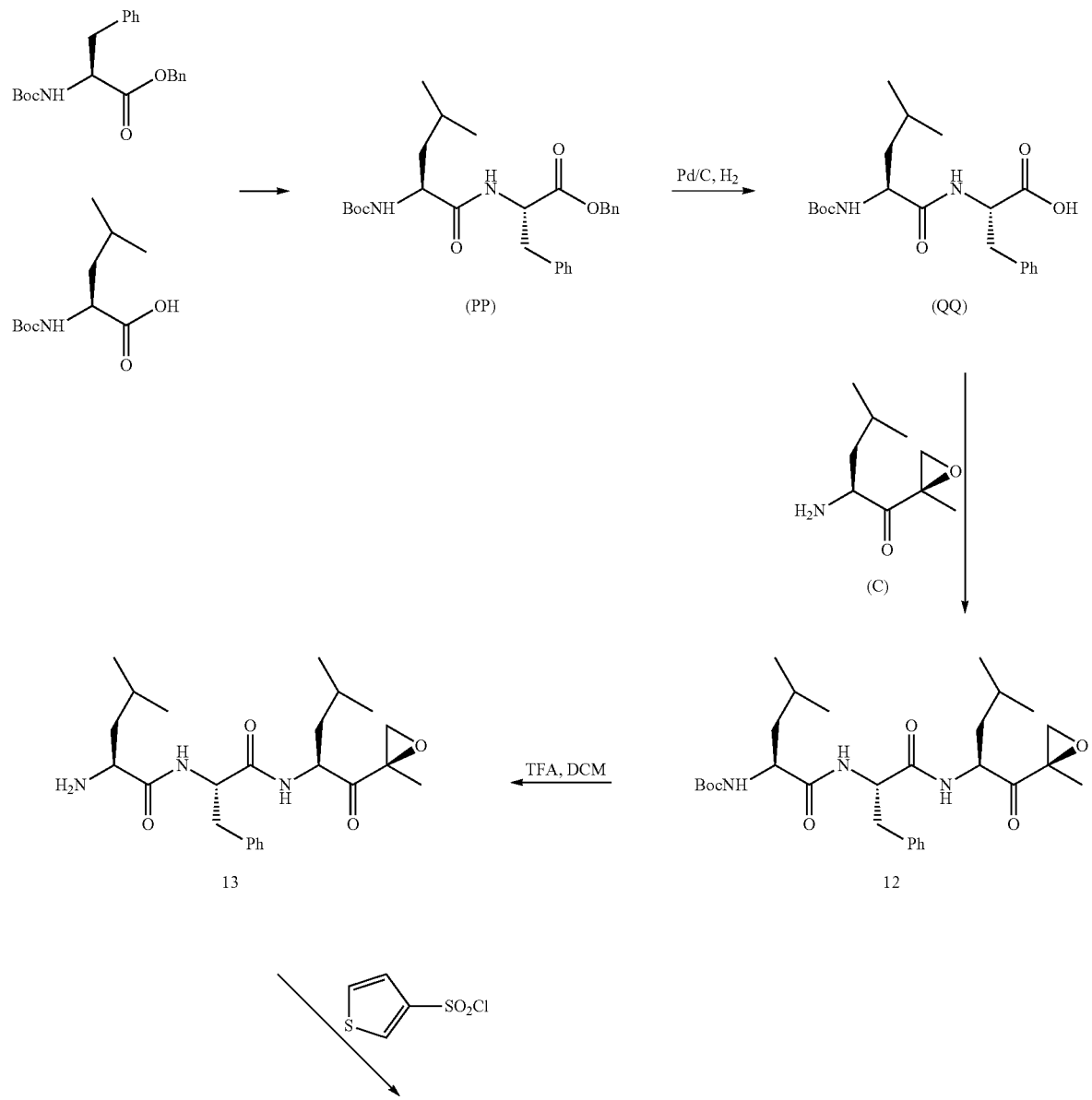

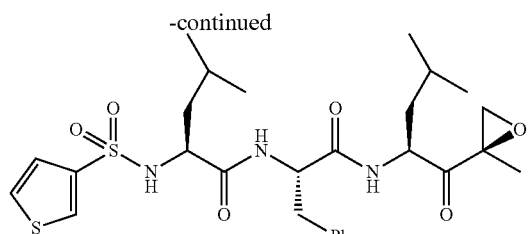

14

Synthesis of (PP)

To a solution of NBoc leucine (85.67 mmol, 19.81 g, 1.0 eq) and phenylalanine benzyl ester (85.67 mmol, 25.0 g, 1.0 eq.) in 900 mL of MeCN was added DIEA (342.68 mmol, 44.29 g, 60 mL, 4.0 eq.) and the mixture cooled to 0° C. in an ice bath. To the mixture was added HOBT (137.08 mmol, 18.52 g, 1.6 eq) followed by PyBOP (137.08 mmol, 71.33 g, 1.6 eq) which was added in several portions over five minutes. The reaction was placed under an atmosphere of argon and stirred overnight. The volatiles were removed under reduced pressure and the remaining material was taken up in 500 mL of EtOAc and washed with sat. NaHCO$_3$, H$_2$O, and brine and dried over MgSO$_4$. The MgSO$_4$ was removed by filtration and the volatiles removed under reduced pressure to give (PP) (37.3 g).

Synthesis of (QQ)

Compound (PP) (4.27 mmol, 2.0 g) was dissolved in MeOH/EtOAc (1:1, 40 mL) and Pd-C (5%, 800 mg) was added. The mixture was stirred at room temperature under 1 atmosphere of hydrogen for 2 hours, and then was filtered through Celite and concentrated to give (QQ).

Synthesis of Compound 12

To a stirred solution of (C) [see: Bioorg. Med. Chem. Letter 1999, 9, 2283-88] (6.0 mmol, 1.8 g, 1.4 eq) in DMF (50 ml) was added (QQ) (4.27 mmol, 2.0 g, 1 eq.), DIEA (0.02 mol, 3.5 mL, 4 eq.) and then HOBT (32 mmol, 4.3 g, 1.6 eq.). The mixture was cooled to 0° C. in an ice bath and PyBOP (32 mmol, 16.6 g, 1.6 eq.) was added in several portions. The mixture was stirred at 5° C. under an atmosphere of nitrogen overnight. The reaction was diluted with sat. NaCl and extracted with EtOAc. The organic layer was washed with water and brine and dried over anhydrous MgSO$_4$, filtered, and concentrated to an oil that was purified by flash chromatography to afford 12 (0.50 g).

Synthesis of Compound 13

Compound 12 (0.046 mmol, 24.5 mg) was mixed with TFA/DCM (80%) and was stirred at room temperature for one hour at which time the mixture was concentrated and placed under high vacuum for 2 hours giving 13.

Synthesis of Compound 14

To a DCM solution (10 mL) of 13 was added 3-thiophenesulfonyl chloride (0.055 mmol 0.012 g, 1.2 eq.) and TEA (0.184 mmol, 0.026 mL, 4.0 eq.). The mixture was stirred at room temperature for 2 hrs and then concentrated to dryness. The residue was taken up in EtOAc, washed with water and brine, and dried with anhydrous MgSO$_4$, filtered, and concentrated to an oil which was purified by prep-HPLC to afford 14 (1 mg). IC$_{50}$ 20S CT-L<50 nM, IC$_{50}$ Cell-based CT-L<50 nM.

Scheme 13: Synthesis of Example 15

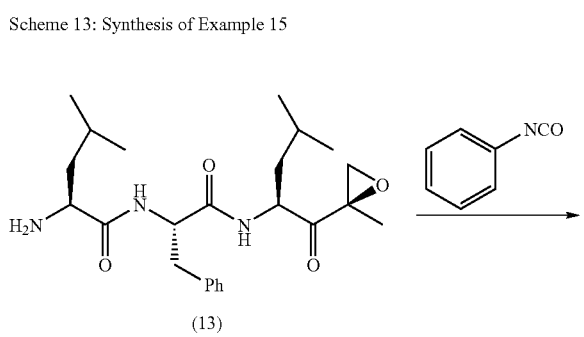

Synthesis of Compound 15

To a DCM solution (2 mL) of 13 (0.092 mmol) was added phenyl isocyanate (0.14 mmol, 0.015 mL, 1.5 eq.) and DIEA (0.276 mmol, 0.050 mL, 3 eq.) and the mixture was stirred at room temperature overnight. The crude mixture was then concentrated to dryness and the residue was taken up in EtOAc. The organic layer was washed with water and brine, and dried with anhydrous MgSO$_4$, filtered, and concentrated to an oil that was purified by prep-HPLC to afford 15 (2.8 mg).

Scheme 14: Synthesis of Example 16

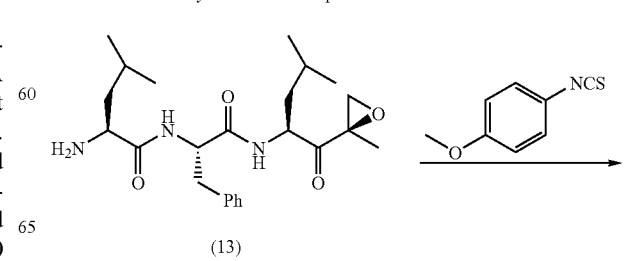

(13)

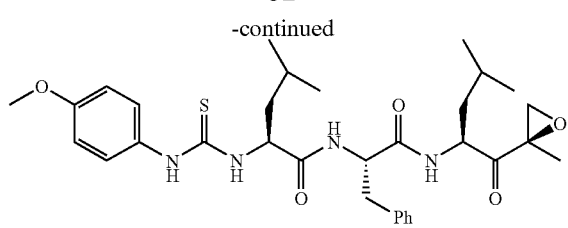

16

Synthesis of Compound 16

To a DCM solution (2 mL) of 13 (0.07 mmol) was added 4-methoxyphenyl isothiocyanate (0.1 mmol, 0.015 mL, 1.5 eq.) and DIEA (0.21 mmol, 0.040 mL, 3 eq.) and the mixture was stirred at room temperature overnight. The crude mixture was concentrated to dryness and the residue was taken up in EtOAc. The organic layer was washed with water and brine, dried with anhydrous MgSO$_4$, filtered, and concentrated to an oil that was purified by flash chromatography to afford 16 (2 mg). IC$_{50}$ 20S CT-L<50 nM, IC$_{50}$ Cell-based CT-L<50 nM.

Scheme 15: Synthesis of Example 17

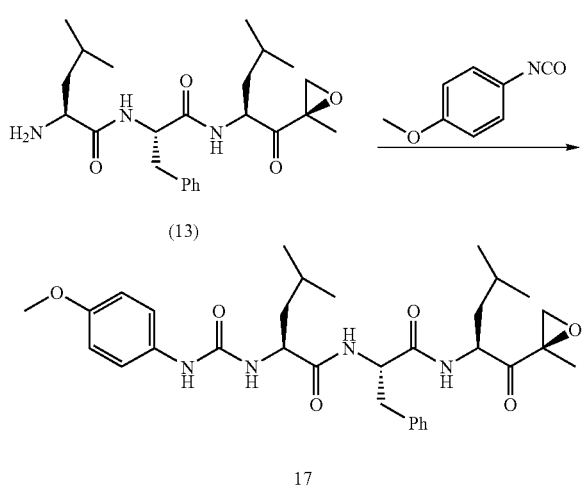

Scheme 17: Synthesis of Example 19

Synthesis of Compound 17

To a DCM solution (2 mL) of 13 (0.092 mmol) was added 4-methoxyphenyl isocyanate (0.14 mmol, 0.018 mL, 1.5 eq.) and DIEA (0.276 mmol, 0.050 mL, 3 eq.) and the mixture was stirred at room temperature overnight. The crude mixture was concentrated to dryness and the residue was taken up in EtOAc. The organic layer was washed with water and brine, dried with anhydrous MgSO$_4$, filtered, and concentrated to an oil that was purified by flash chromatography to afford 17 (2.5 mg). IC$_{50}$ 20S CT-L<50 nM, IC$_{50}$ Cell-based CT-L<50 nM.

Scheme 16: Synthesis of Example 18

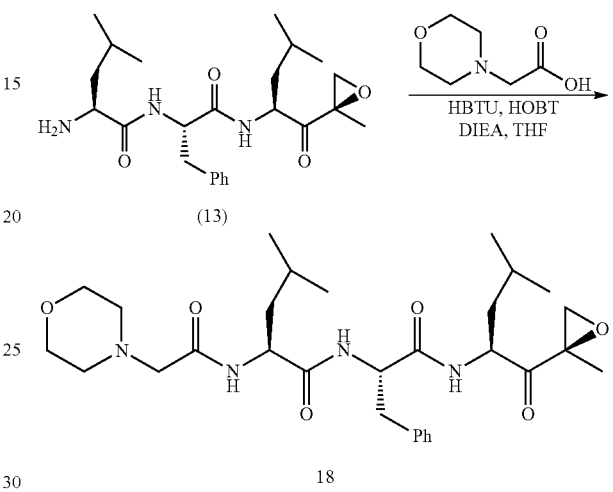

18

Synthesis of Compound 18

To a THF solution (15 mL) of 13 (1.4 mmol) at 0° C. was added 4-morpholinoacetic acid (1.79 mmol, 0.260 g), HOBT (1.92 mmol, 0.260 g), HBTU (1.72 mmol, 0.656 g), and DIEA (11.45 mmol, 2.0 mL) and the mixture was stirred and allowed to warm to room temperature overnight. The reaction was diluted with sat. NaHCO$_3$ (15 mL) and the layers were separated. The aqueous layer was extracted with EtOAc (3×5 mL) the organic layers combined, washed with H$_2$O (1×15 mL) and brine (1×15 mL), and dried over MgSO$_4$. The MgSO$_4$ was removed by filtration and the volatiles removed under reduced pressure. The crude material was purified by flash chromatography to afford 18 (0.423 g). IC$_{50}$ 20S CT-L<50 nM, IC$_{50}$ Cell-based CT-L<50 nM.

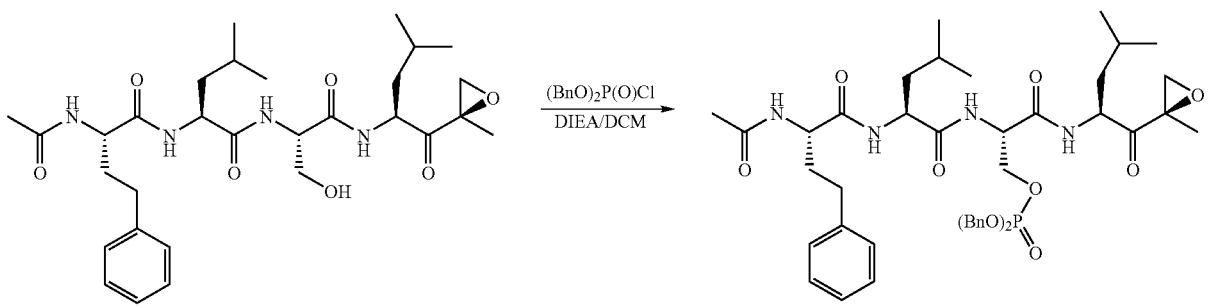

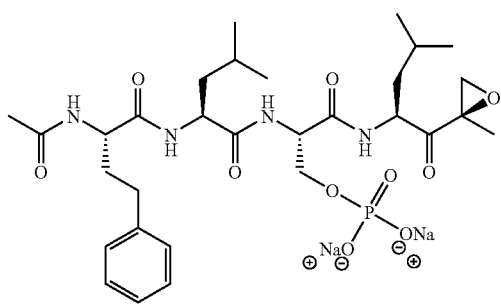

19

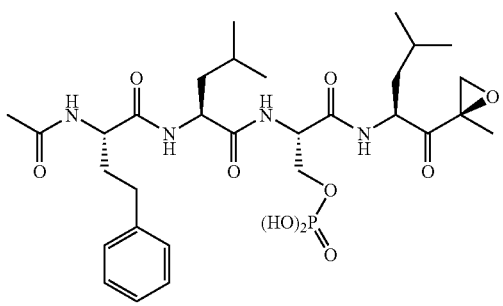

(SS)

Synthesis of (RR)

To a solution of 2 (1 mmol) and DIEA (1.5 mmol) in dry CH$_2$Cl$_2$ (100 mL) at 0° C. is added a solution of dibenzylphosphoryl chloride (1 mmol) in dichloromethane (10 mL) dropwise. The reaction mixture is stirred at room temperature until complete, washed with cold 1N HCl and then brine, dried over MgSO$_4$, filtered, and evaporated to yield (RR).

Synthesis of (SS)

A solution of (RR) (1 mmol) and wet 20% Pd(OH)$_2$/C (100 mg; Pearlman's catalyst) in EtOAc (10 mL) is subjected to hydrogenation at atmospheric pressure and ambient temperature until complete. The reaction mixture is filtered through Celite, and evaporated to afford the desired compound (SS). This material so isolated can be utilized as is for either the next step or for testing in any assay.

Synthesis of Compound 19

Compound (SS) (1 mmol) is diluted with MeOH (5 mL) and treated with a standardized solution of 1.00 N NaOH (2.00 mmol) in H$_2$O (2 mL). The solution is allowed to stir for 2 hours and lyophilized to afford 19.

Scheme 18: Synthesis of Example 20

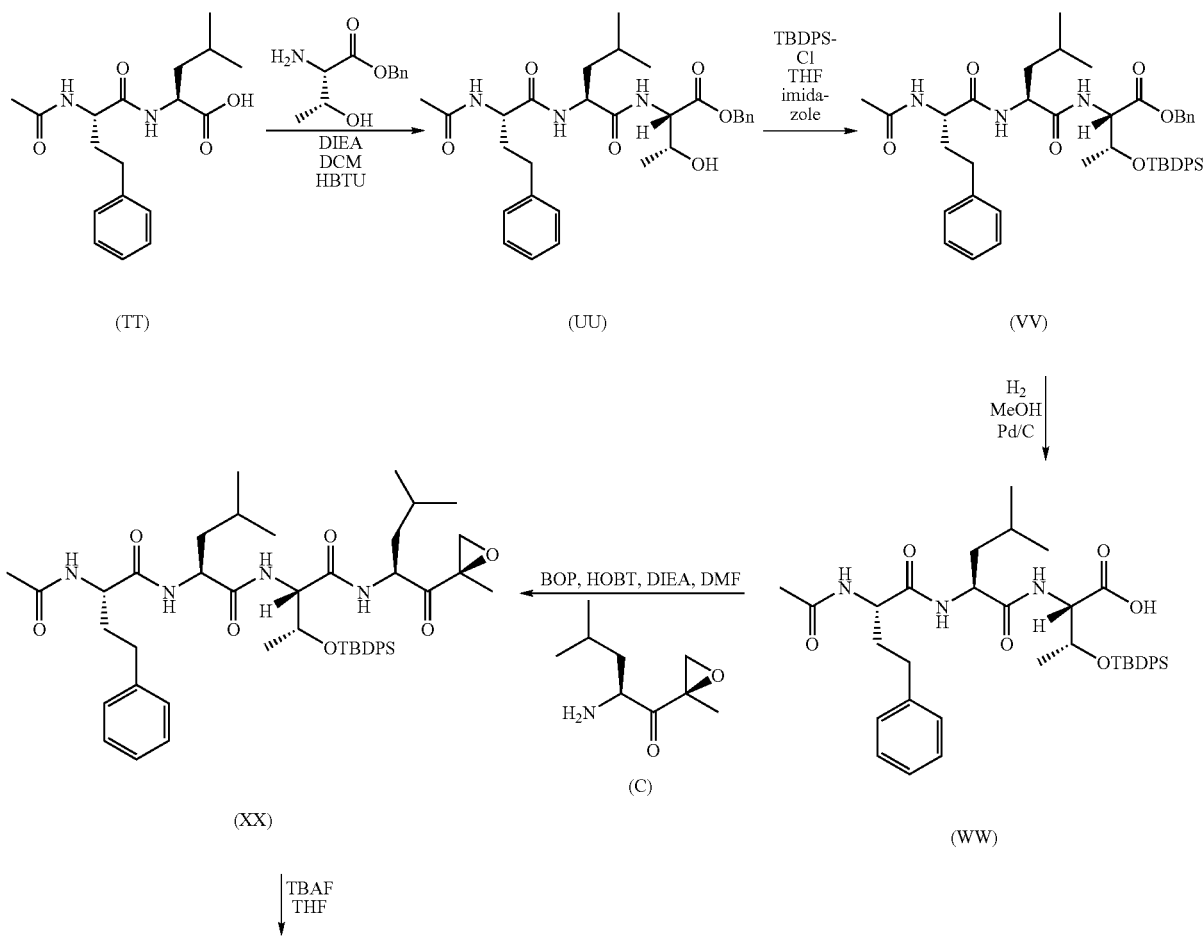

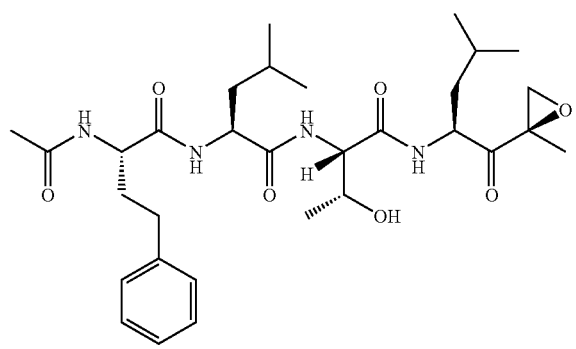

20

Synthesis of (UU)

To a solution of (TT) (1 mmol) [obtained via standard methods of solution phase peptide synthesis], threonine benzyl ester (1 mmol) and DIEA (2.5 mmol) in dry $CH_2Cl_2$ (100 mL) is added HBTU (2.5 mmol). The reaction mixture is stirred at room temperature until complete, washed with 1N HCl and water, dried over $MgSO_4$, filtered, and evaporated to yield (UU).

Synthesis of (VV)

To compound (UU) (1 mmol) in dry $CH_2Cl_2$ (100 mL) is added TBDPSCl (1 mmol) and imidazole (1.2 mmol). The reaction mixture is stirred at room temperature until complete, washed with 1N HCl and water, dried over $MgSO_4$, filtered, and evaporated to yield (VV).

Synthesis of (WW)

A solution of (VV) (1 mmol) and 10% Pd/C (100 mg) in MeOH (10 mL) is subjected to hydrogenation at atmospheric pressure and ambient temperature until complete. The reaction mixture is filtered through Celite, and evaporated to afford (WW).

Synthesis of (XX)

To a solution of (WW) (1 mmol) and E (1 mmol) [see: Bioorg. Med. Chem. Letter 1999, 9, 2283-88] in DMF (10 mL) is added HOBT (1.60 mmol) and DIEA (4 mmol). The mixture is cooled to 0° C. and BOP (1.60 mmol) is added over several minutes. The resulting solution is warmed to room temperature and stirred over night. The reaction mixture is diluted with brine and extracted with EtOAc. The combined organic is extracted with $H_2O$ and brine, dried over $MgSO_4$, and evaporated to yield (XX).

Synthesis of Compound 20

To a solution of (XX) (1 mmol) in THF (100 mL) at rt is added slowly TBAF (1 mmol) and the resulting mixture is stirred until complete. Evaporation and chromatography of the resultant residue affords 20.

Scheme 19: Synthesis of Example 21

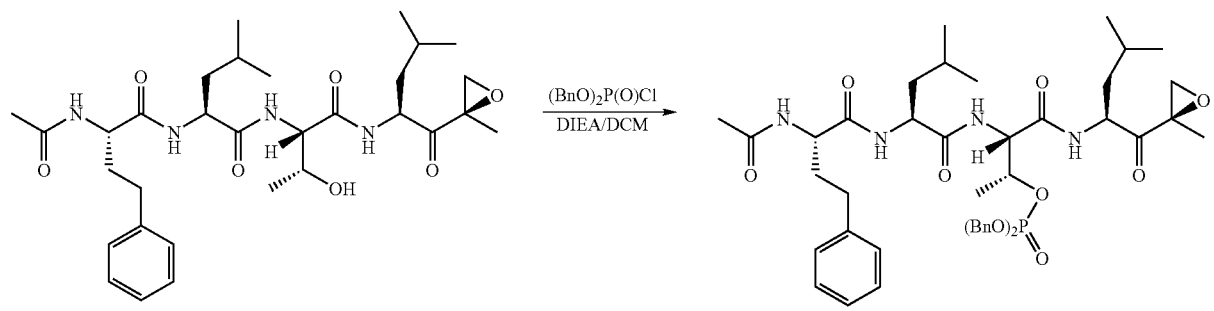

20      (CCC)

$H_2$, $Pd(OH)_2$/C
EtOAc

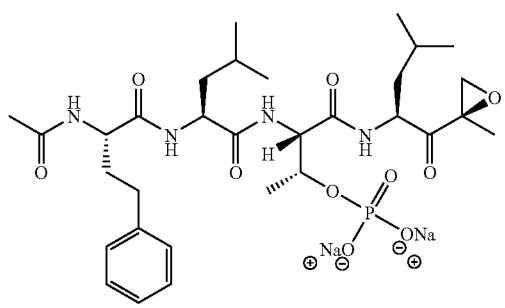

21

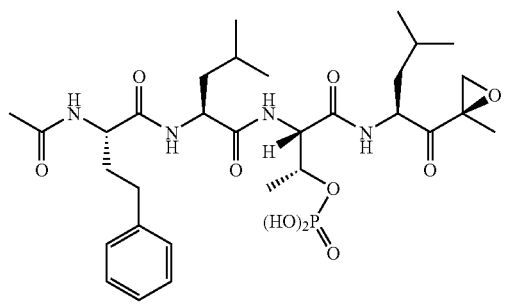

(DDD)

Synthesis of (CCC)

The target compound is prepared by essentially following the procedure for the conversion of 2 to (RR) except 20 is used in place of 2.

Synthesis of (DDD)

The target compound is prepared by essentially following the procedure for the conversion of (RR) to (SS) except (CCC) is used in place of (RR).

Synthesis of Compound 21

The target compound is prepared by essentially following the procedure for the conversion of (SS) to 19 except (DDD) is used in place of (SS).

Scheme 20: Synthesis of Example 22

Synthesis of (EEE)

[See: J. Med. Chem. 1999, 42(16), 3094-3100.] To a solution of dibenzyl chloromethyl phosphate (1 mmol) [U.S. Pat. No. 6,204,257] in anhydrous acetonitrile under argon is added compound 2 (1 mmol) and 1,2,2,6,6-pentamethylpiperidine (1.2 mmol) followed by stirring at 70° C. until complete. The solvent is then removed in vacuo to afford (EEE).

Synthesis of (FFF)

The target compound is prepared by essentially following the procedure for the conversion of (RR) to (SS) except (EEE) is used in place of (RR).

Synthesis of Compound 22

The target compound is prepared by essentially following the procedure for the conversion of (SS) to 19 except (FFF) is used in place of (SS).

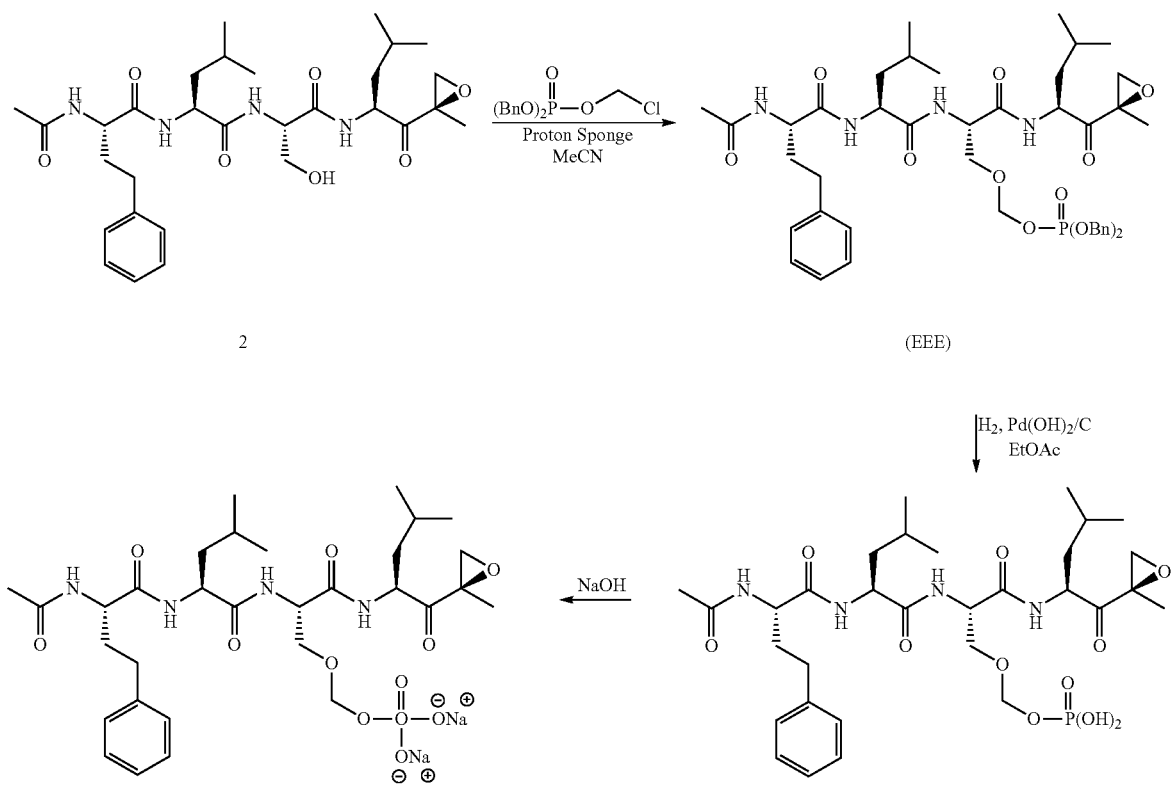

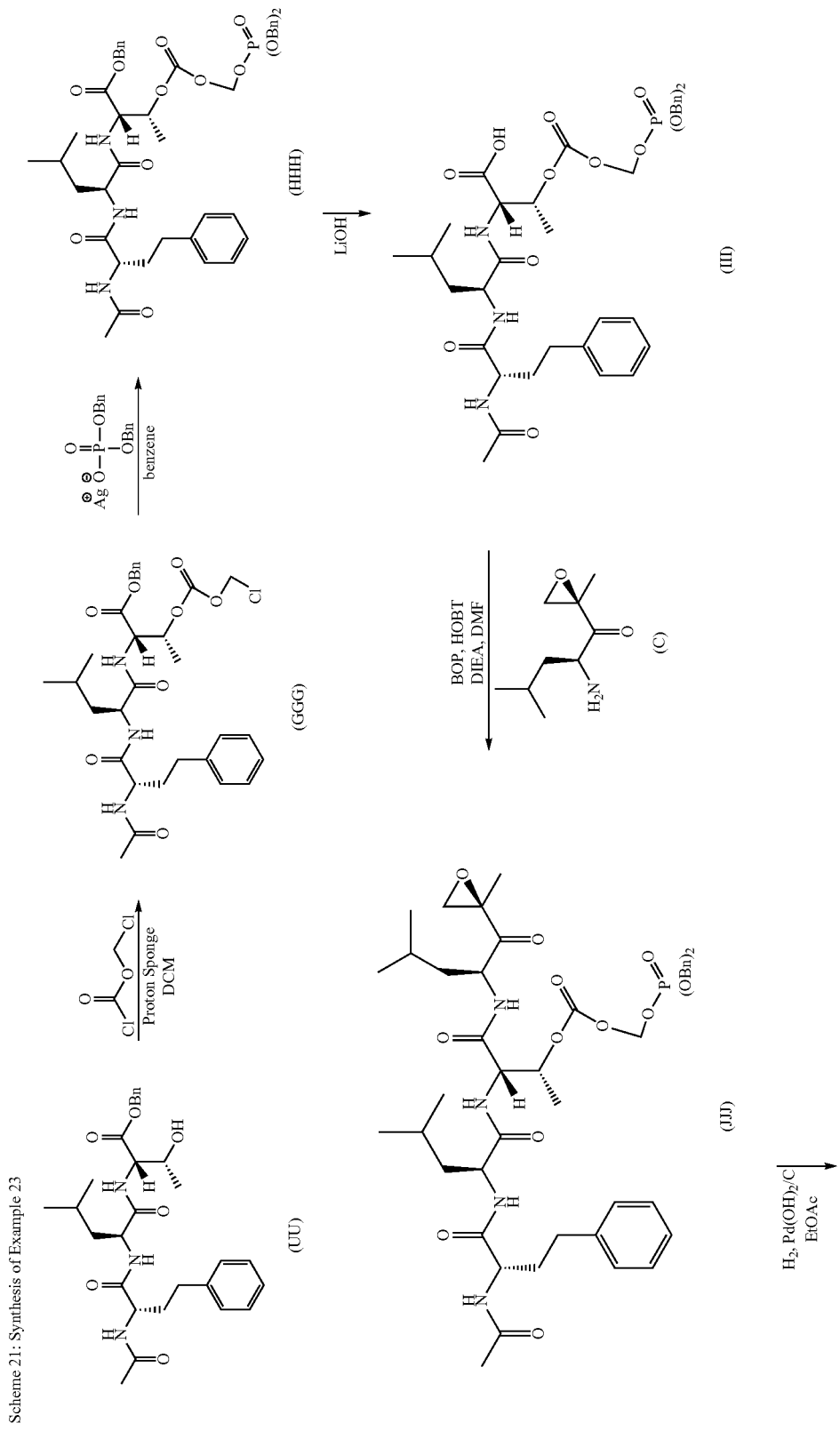
Scheme 21: Synthesis of Example 23

-continued
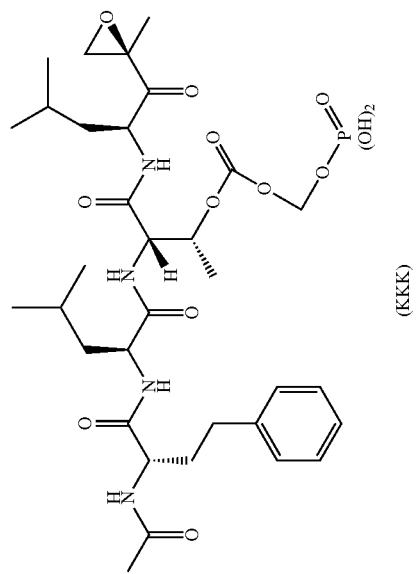
(KKK)
$\xrightarrow{\text{NaOH}}$
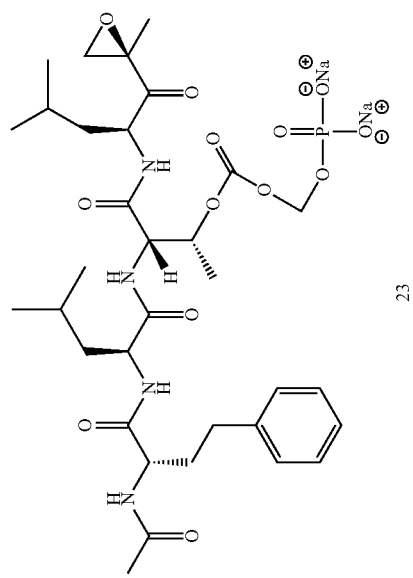
23

Synthesis of (GGG)

(see Pharmaceutical Research 1993, 10(9), 1350-55.) To a solution of (UU) (1 mmol) and Proton Sponge (1 mmol) in dry $CH_2Cl_2$ (10 mL) at 0° C., is added a solution of chloromethyl chloroformate (1 mmol) in dichloromethane (10 mL) dropwise. The reaction mixture is stiffed at room temperature overnight, washed with 1N HCl and water, dried over $MgSO_4$, filtered, and evaporated to yield (GGG).

Synthesis of (HHH)

A solution of (GGG) (1 mmol) and silver dibenzylphosphate (1.5 mmol) in dry benzene (10 mL) is refluxed overnight. The reaction mixture is cooled, filtered, washed with a saturated $Na_2CO_3$ solution, dried over $MgSO_4$ and evaporated to yield (HHH).

Synthesis of (III)

To a solution of (HHH) (1 mmol) in 3:1 $MeOH/H_2O$ (20 mL) at 0° C. is added a solution of LiOH (5 mmol) in $H_2O$ (2.5 mL) dropwise. The reaction is covered with argon and stored at 5° C. overnight. The reaction is quenched at 0° C. by the addition of saturated $NH_4Cl$ (50 mL) and diluted with cold water (150 mL). The pH is adjusted to 2 at 0° C. with cold 6N HCl, and the resulting solids are collected by vacuum filtration to yield (III).

Synthesis of (JJJ)

The target compound is prepared by essentially following the procedure for the conversion of (WW) to (XX) except (III) is used in place of (WW).

Synthesis of (KKK)

The target compound is prepared by essentially following the procedure for the conversion of (RR) to (SS) except (JJJ) is used in place of (RR).

Synthesis of Compound 23

The target compound is prepared by essentially following the procedure for the conversion of (SS) to 19 except (KKK) is used in place of (SS).

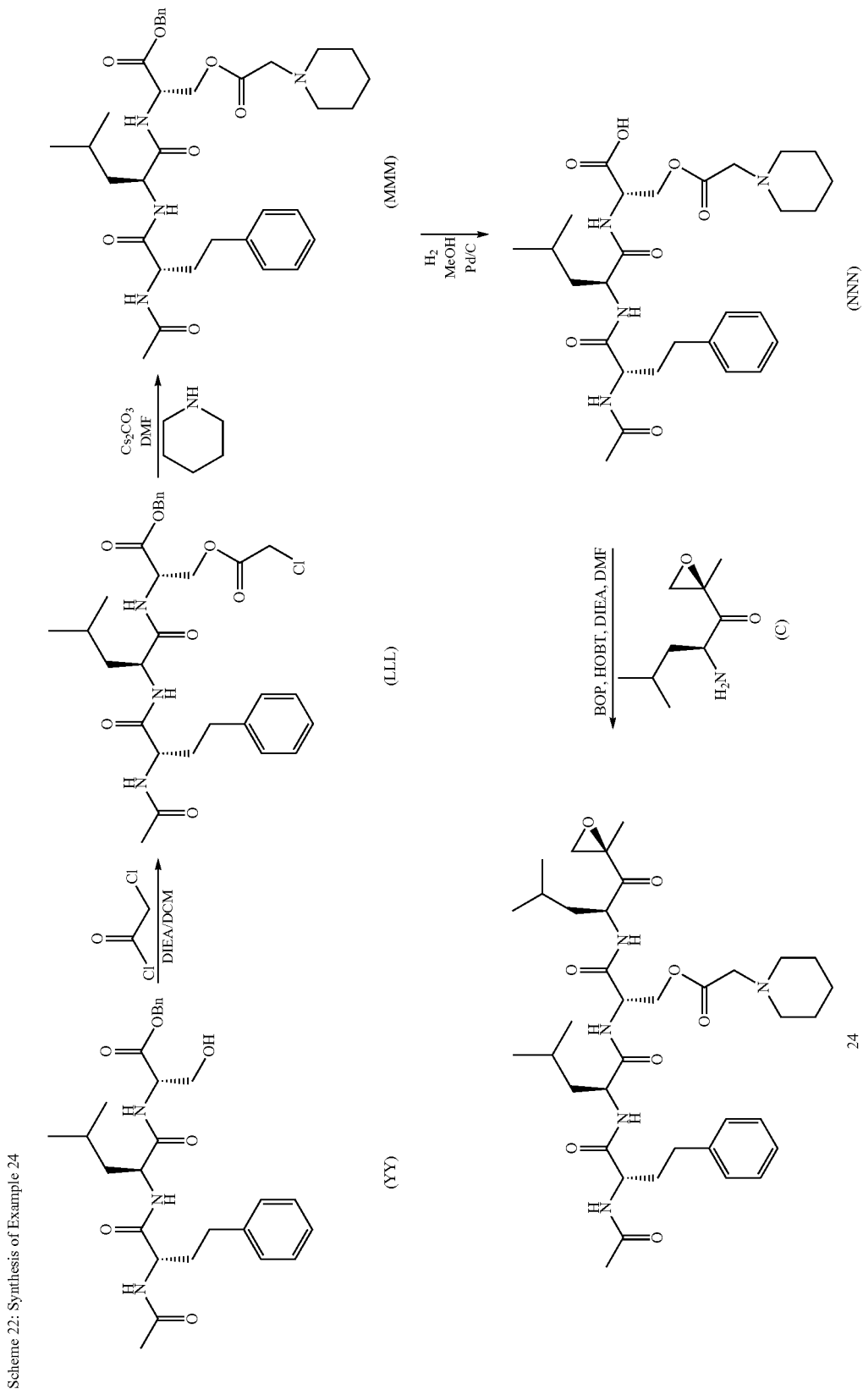
Scheme 22: Synthesis of Example 24

Synthesis of (LLL)

The target compound (LLL) is obtained by essentially following the procedure for the conversion of 2 to (RR) substituting compound (YY) [obtained via standard methods of solution phase peptide synthesis] for compound 2 and chloroacetyl chloride for dibenzylphosphoryl chloride.

Synthesis of (MMM)

To a solution of (LLL) (1 mmol) in DMF (10 mL) at rt under argon is added $Cs_2CO_3$ (1 mmol) followed by piperidine (1 mmol). Stirring is continued until the reaction is complete. The mixture is then poured into brine and washed with EtOAc. The EtOAc is dried over $MgSO_4$, filtered, and evaporated under reduced pressure to yield compound (MMM).

Synthesis of (NNN)

The target compound is prepared by essentially following the procedure for the conversion of (VV) to (WW) except (MMM) is used in place of (VV).

Synthesis of Compound 24

The target compound is prepared by essentially following the procedure for the conversion of (WW) to (XX) except (NNN) is used in place of (WW).

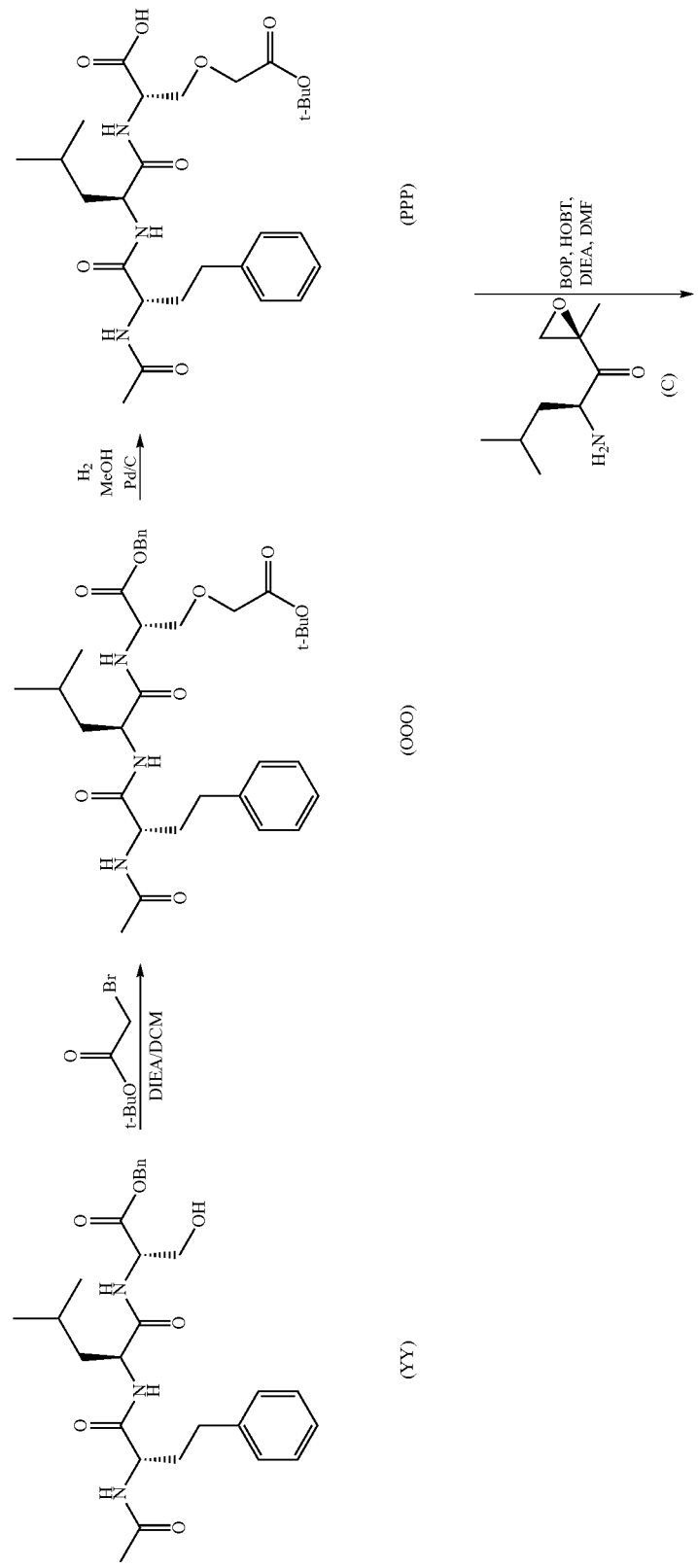
Scheme 23: Synthesis of Example 25

-continued
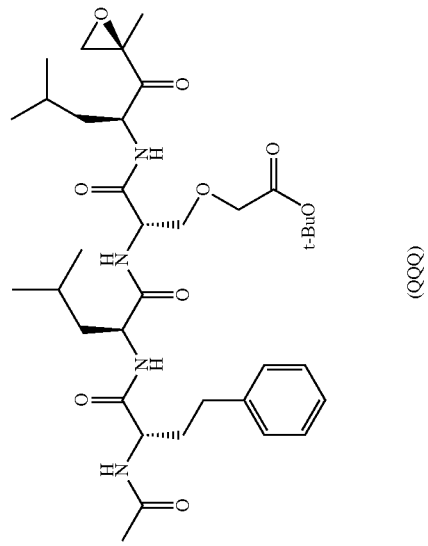
(QQQ)
↓ TFA (neat)
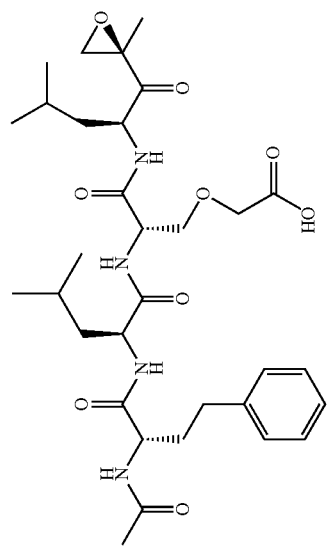
25

Synthesis of (OOO)

The target compound is prepared by essentially following the procedure for the conversion of 2 to (RR) except (YY) is used in place of 2 and tert-butyl bromoacetate is used in place of dibenzyl phosphoryl chloride.

Synthesis of (PPP)

The target compound is prepared by essentially following the procedure for the conversion of (VV) to (WW) except (OOO) is used in place of (VV).

Synthesis of (QQQ)

The target compound is prepared by essentially following the procedure for the conversion of (WW) to (XX) except (PPP) is used in place of (WW).

Synthesis of Compound 25

Treatment of (QQQ) (1 mmol) with neat TFA (10 mL) at 0° C. followed by evaporation of the TFA under reduced pressure see: Bioorg. Med. Chem. Letter 1999, 9, 2283-88] affords 25.

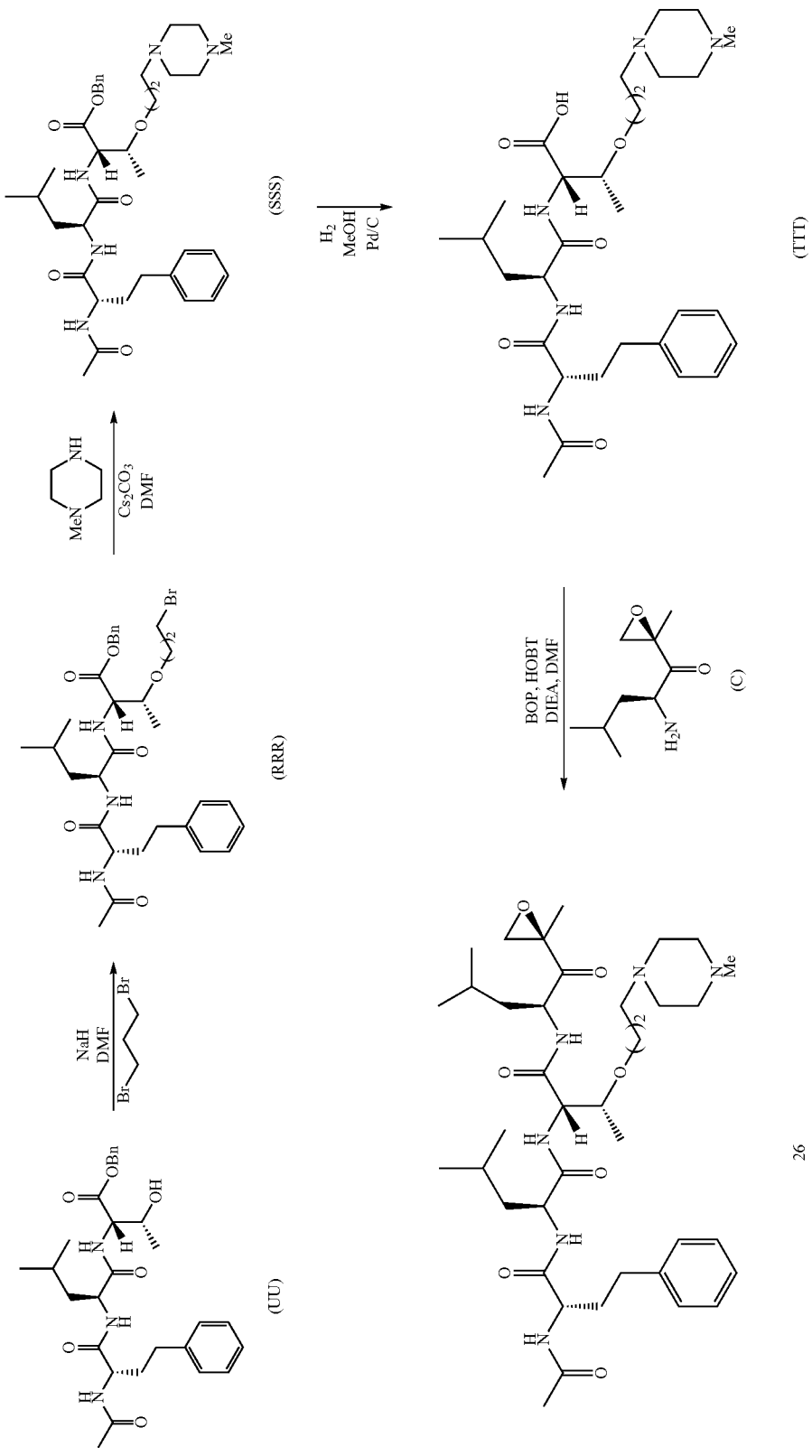
Scheme 24: Synthesis of Example 26

Synthesis of (RRR)

To a solution of (UU) (1 mmol) in anhydrous DMF (10 mL) at rt is carefully added NaH (1 mmol). After stirring for 0.5 hr, the mixture is treated with 1,3-dibromopropane (1.2 mmol) and the reaction is stirred until complete. The solution is then carefully quenched via the addition of saturated NH$_4$Cl (1 mL) followed by pouring the mixture into cold brine (10 mL). The resulting mixture is washed with CH$_2$Cl$_2$, dried over MgSO$_4$, filtered, and the solvent is evaporated under reduced pressure to afford (RRR).

Synthesis of (SSS)

To a solution of (RRR) (1 mmol) in anhydrous DMF (10 mL) at rt under argon is added Cs$_2$CO$_3$ (1 mmol) followed by N-methylpiperazine (1 mmol). Stirring is maintained until the reaction is complete. The mixture is then poured into brine and washed with EtOAc. The EtOAc is dried over MgSO$_4$, filtered, and evaporated under reduced pressure to yield compound (SSS).

Synthesis of (TTT)

The target compound is prepared by essentially following the procedure for the conversion of (VV) to (WW) except (SSS) is used in place of (VV).

Synthesis of Compound 26

The target compound is prepared by essentially following the procedure for the conversion of (WW) to (XX) except (TTT) is used in place of (WW).

Scheme 25: Synthesis of Example 27

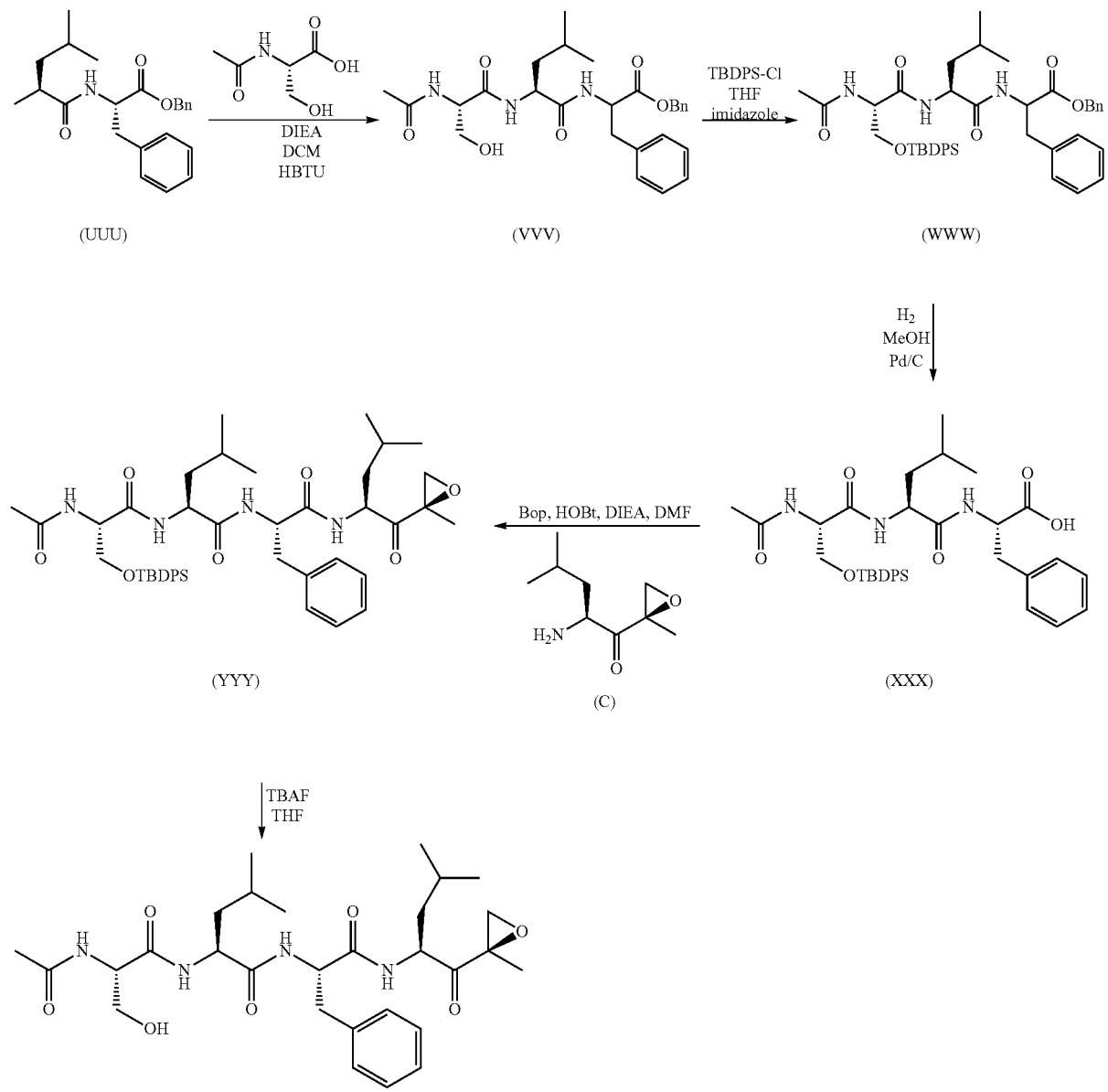

Synthesis of (VVV)

The target compound is prepared by essentially following the procedure for the conversion of (TT) to (UU) except N-acetyl serine is used in place of (TT) and (UUU) [obtained via standard methods of solution phase peptide synthesis] is used in place of serine benzyl ester.

Synthesis of (WWW)

The target compound is prepared by essentially following the procedure for the conversion of (UU) to (VV) except (VVV) is used in place of (UU).

Synthesis of (XXX)

The target compound is prepared by essentially following the procedure for the conversion of (VV) to (WW) except (WWW) is used in place of (VV).

Synthesis of (YYY)

The target compound is prepared by essentially following the procedure for the conversion of (WW) to (XX) except (XXX) is used in place of (WW).

Synthesis of Compound 27

The target compound is prepared by essentially following the procedure for the conversion of (XX) to 20 except (YYY) is used in place of (XX).

Synthesis of (ZZZ)

The target compound is prepared by essentially following the procedure for the conversion of 2 to (RR) except 27 is used in place of 2.

Synthesis of (AAAA)

The target compound is prepared by essentially following the procedure for the conversion of (RR) to (SS) except (ZZZ) is used in place of (RR).

Synthesis of Compound 28

The target compound is prepared by essentially following the procedure for the conversion of (SS) to 19 except (AAAA) is used in place of (SS).

Scheme 26: Synthesis of Example 28

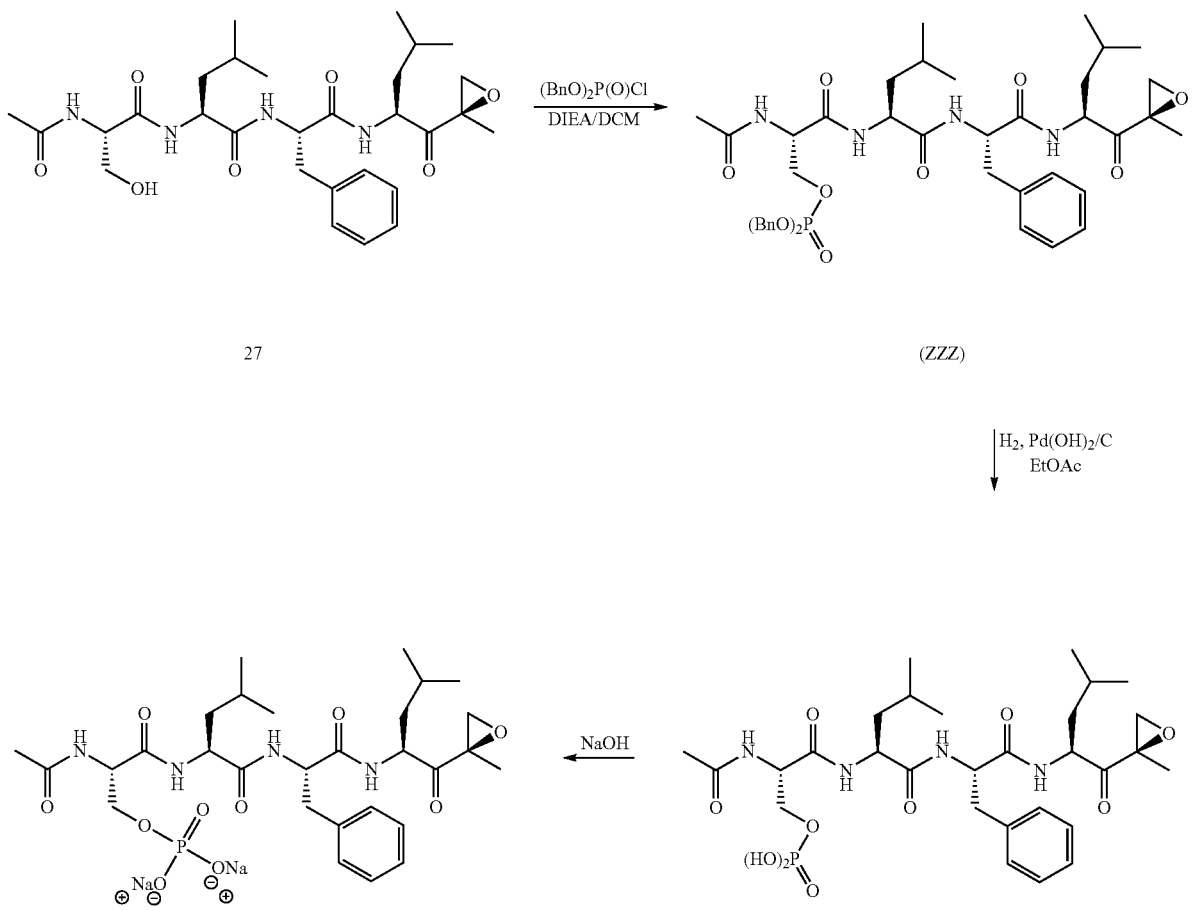

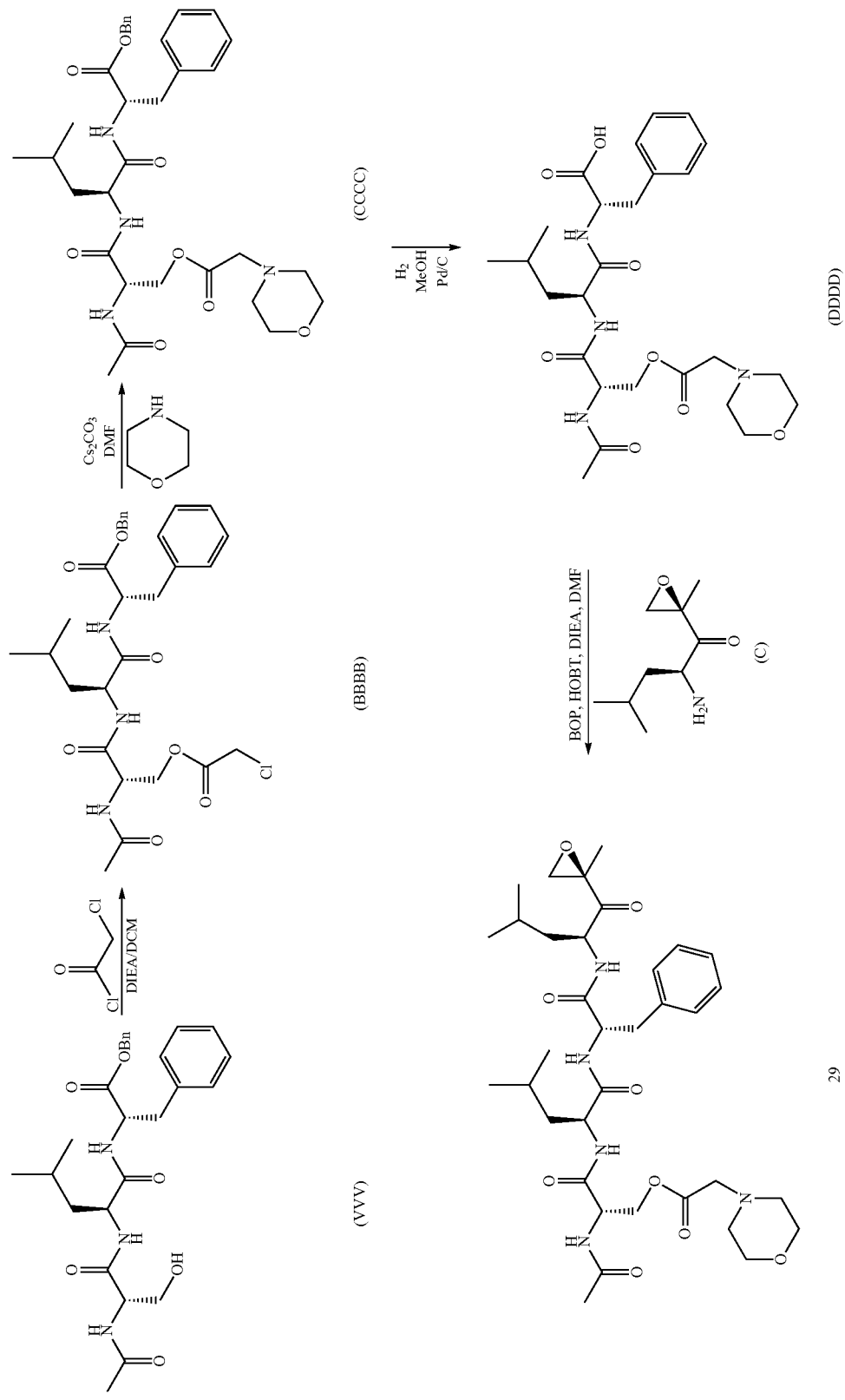
Scheme 27: Synthesis of Example 29

Synthesis of (BBBB)

The target compound is prepared by essentially following the procedure for the conversion of (YY) to (LLL) except (VVV) is used in place of (SS).

Synthesis of (CCCC)

The target compound is prepared by essentially following the procedure for the conversion of (LLL) to (MMM) except (BBBB) is used in place of (LLL) and morpholine is used in place of piperidine.

Synthesis of (DDDD)

The target compound is prepared by essentially following the procedure for the conversion of (MMM) to (NNN) except (CCCC) is used in place of (MMM).

Synthesis of Compound 29

Compound (WW) is prepared by essentially following the procedure for the conversion of (WW) to (XX) except (DDDD) is used in place of (WW).

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A compound having a structure of formula (III) or a pharmaceutically acceptable salt thereof

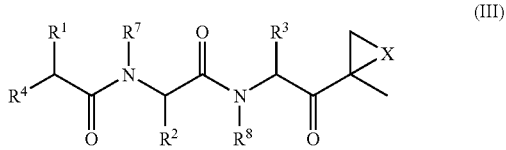

(III)

wherein each Ar is independently an aromatic or heteroaromatic group optionally substituted with 1-4 substituents;

L is selected from C=O, C=S, and SO$_2$;

X is selected from O, S, NH, and N—C$_{1-6}$alkyl;

Y is absent or is selected from C=O and SO$_2$;

Z is absent or is C$_{1-6}$alkyl;

R$^1$, R$^2$, and R$^3$ are each independently selected from C$_{1-6}$alkyl, C$_{1-6}$hydroxyalkyl, C$_{1-6}$alkoxyalkyl, aryl, and C$_{1-6}$aralkyl, any of which is optionally substituted with one or more of amide, amine, carboxylic acid (or a salt thereof), ester, thiol, or thioether substituents;

R$^4$ is N(R$^5$)L—Z—R$^6$;

R$^5$ is selected from hydrogen, OH, C$_{1-6}$aralkyl-Y-, and C$_{1-6}$alkyl-Y-;

R$^6$ is selected from OR$^7$, C$_{2-6}$alkenyl, Ar—Y—, carbocyclyl, and heterocyclyl; and R$^7$ and R$^8$ are independently selected from hydrogen and C$_{1-6}$alkyl.

2. The compound of claim 1, or a pharmaceutically acceptable salt thereof, wherein X is O; R$^1$, R$^2$, and R$^3$ are independently selected from C$_{1-6}$alkyl and C$_{1-6}$aralkyl.

3. The compound of claim 2, or a pharmaceutically acceptable salt thereof, wherein R$^1$ and R$^3$ are both C$_{1-6}$alkyl; R$^2$ is C$_{1-6}$aralkyl; and R$^7$ and R$^8$ are independently selected from hydrogen and methyl.

4. The compound of claim 3, or a pharmaceutically acceptable salt thereof, wherein R$^1$ and R$^3$ are both isobutyl, R$^2$ is phenylmethyl, and R$^7$ and R$^8$ are both hydrogen.

5. The compound of claim 4, or a pharmaceutically acceptable salt thereof, wherein R$^5$ is hydrogen, L is C=O or SO$_2$, and R$^6$ is Ar—Y—.

6. The compound of claim 5, or a pharmaceutically acceptable salt thereof, wherein each Ar is independently selected from phenyl, indolyl, benzofuranyl, naphthyl, quinolinyl, quinolonyl, thienyl, pyridyl, and pyrazyl.

7. The compound of claim 6, or a pharmaceutically acceptable salt thereof, wherein Ar is substituted with Ar—Q—, wherein Q is selected from a direct bond, —O—, and C$_{1-6}$alkyl.

8. The compound of claim 5, or a pharmaceutically acceptable salt thereof, wherein Z is C$_{1-6}$alkyl.

9. The compound of claim 8, or a pharmaceutically acceptable salt thereof, wherein Z is substituted with Ar.

10. The compound of claim 9, or a pharmaceutically acceptable salt thereof, wherein Ar is phenyl.

11. The compound of claim 4, or a pharmaceutically acceptable salt thereof, wherein R$^5$ is hydrogen, L is C=O or SO$_2$, Z is absent, and R$^6$ is selected from Ar—Y and heterocyclyl.

12. The compound of claim 11, or a pharmaceutically acceptable salt thereof, wherein R$^6$ is selected from chromonyl, chromanyl, morpholino, and piperidinyl.

13. The compound of claim 11, or a pharmaceutically acceptable salt thereof, wherein R$^6$ is Ar—Y and Ar is selected from phenyl, indolyl, benzofuranyl, naphthyl, quinolinyl, quinolonyl, thienyl, pyridyl, and pyrazyl.

14. The compound of claim 4, or a pharmaceutically acceptable salt thereof, wherein $R^5$ is hydrogen, L is C=O or $SO_2$, Z is absent, and $R^6$ is $C_{2-6}$alkenyl.

15. The compound of claim 14, or a pharmaceutically acceptable salt thereof, wherein $C_{1-6}$alkenyl is a substituted vinyl group.

16. The compound of claim 15, or a pharmaceutically acceptable salt thereof, wherein the substituent is an aryl or heteroaryl group.

17. The compound of claim 16, or a pharmaceutically acceptable salt thereof, wherein the substituent is a phenyl group optionally substituted with 1 to 4 substituents.

18. A pharmaceutical composition comprising a compound of claim 1, or a pharmaceutically acceptable salt thereof and a pharmaceutically acceptable carrier.

19. A method of inhibiting an N-terminal nucleophile hydrolase, wherein said inhibitor inhibits a chymotrypsin-like activity of said 20S proteasome when said inhibitor is present at concentrations below about 5 μM, and does not inhibit trypsin-like activity or PGPH activity of said 20S proteasome when said inhibitor is present at concentrations below about 5 μM, comprising contacting the N-terminal nucleophile hydrolase with a compound of claim 1 or a pharmaceutically acceptable salt thereof or a composition of claim 18.

20. A method for the treatment of inflammation, comprising administering to a patient a therapeutically effective amount of a compound of claim 1, or a pharmaceutically acceptable salt thereof, or a composition of claim 18.

* * * * *

UNITED STATES PATENT AND TRADEMARK OFFICE
CERTIFICATE OF CORRECTION

| | | |
|---|---|---|
| PATENT NO. | : 8,088,741 B2 | Page 1 of 1 |
| APPLICATION NO. | : 11/596028 | |
| DATED | : January 3, 2012 | |
| INVENTOR(S) | : Mark S. Smyth | |

It is certified that error appears in the above-identified patent and that said Letters Patent is hereby corrected as shown below:

Title Page, Column 2, Line 6 (Abstract), please delete "chymotrypsinlike" and insert --chymotrypsin-like--, therefor.

Column 95, Line 17, (Claim 18), please delete "thereof" and insert --thereof,--, therefor.

Signed and Sealed this
First Day of May, 2012

David J. Kappos
*Director of the United States Patent and Trademark Office*